(12) United States Patent
Jiang et al.

(10) Patent No.: US 12,391,687 B2
(45) Date of Patent: Aug. 19, 2025

(54) FIVE-AND-SIX-MEMBERED HETEROCYCLIC COMPOUND AND USE THEREOF AS PROTEIN RECEPTOR KINASE INHIBITOR

(71) Applicant: SHANGHAI ENNOVABIO PHARMACEUTICALS CO., LTD., Shanghai (CN)

(72) Inventors: Lei Jiang, Shanghai (CN); Zhiyong Feng, Shanghai (CN); Xian Jin, Shanghai (CN); Zhi Qiao, Shanghai (CN); Jianyong Shou, Shanghai (CN); Ke Shang, Shanghai (CN); Danyi Wu, Shanghai (CN); Lingling Xu, Shanghai (CN); Yuan Xu, Shanghai (CN); Shuyun Zhang, Shanghai (CN); Yi Zhang, Shanghai (CN); Yuxing Zhang, Shanghai (CN)

(73) Assignee: SHANGHAI ENNOVABIO PHARMACEUTICALS CO., LTD., Shanghai (CN)

( * ) Notice: Subject to any disclaimer, the term of this patent is extended or adjusted under 35 U.S.C. 154(b) by 1134 days.

(21) Appl. No.: 17/439,012

(22) PCT Filed: Nov. 13, 2019

(86) PCT No.: PCT/CN2019/118198
§ 371 (c)(1),
(2) Date: Sep. 14, 2021

(87) PCT Pub. No.: WO2020/098720
PCT Pub. Date: May 22, 2020

(65) Prior Publication Data
US 2022/0144827 A1    May 12, 2022

(30) Foreign Application Priority Data
Nov. 13, 2018   (CN) .................. 201811346840.8

(51) Int. Cl.
C07D 471/04    (2006.01)

(52) U.S. Cl.
CPC .................. *C07D 471/04* (2013.01)

(58) Field of Classification Search
None
See application file for complete search history.

(56) References Cited

U.S. PATENT DOCUMENTS

2022/0017512 A1 *   1/2022   Jiang ................... C07D 519/00

FOREIGN PATENT DOCUMENTS

EP           1749829 A1 *   2/2007   ........... C07D 471/04

OTHER PUBLICATIONS

Brown, N. (2012). Bioisosteres in Medicinal Chemistry. John Wiley & Sons, p. 61 (Year: 2012).*

* cited by examiner

*Primary Examiner* — Jeffrey S Lundgren
*Assistant Examiner* — Anthony Joseph Seitz
(74) *Attorney, Agent, or Firm* — Mintz Levin Cohn Ferris Glovsky and Popeo, P.C.

(57) ABSTRACT

A class of five-membered fused with six-membered heterocyclic compounds represented by formula I and a pharmaceutical composition, preparation, and an application thereof are disclosed. These compounds have TRK kinase inhibitory activity and can treat diseases related to TRK dysfunction.

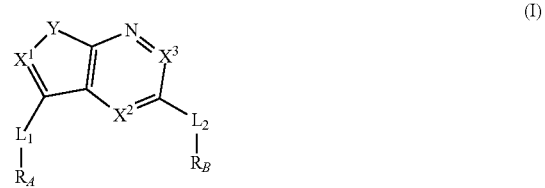

8 Claims, No Drawings

FIVE-AND-SIX-MEMBERED HETEROCYCLIC COMPOUND AND USE THEREOF AS PROTEIN RECEPTOR KINASE INHIBITOR

RELATED APPLICATION

This application is a U.S. National Stage Application under 35 U.S.C. § 371 of International Patent Application No.: PCT/CN2019/118198, filed Nov. 13, 2019, which claims priority to Chinese Patent Application No.: 201811346840.8, filed Nov. 13, 2018.

FIELD OF THE INVENTION

The present invention relates to pharmaceutical compounds, and in particular, a class of TRK kinase inhibitors and the preparation and use thereof.

BACKGROUND OF THE INVENTION

Tropomyosin-receptor kinase (TRK) is a type of nerve growth factor receptor which belongs to the receptor tyrosine kinase family, and mainly includes three highly homologous members TRKA, TRKB and TRKC, which are respectively encoded by NTRK1, NTRK2, and NTRK3. These receptor tyrosine kinases are mainly expressed in nerve tissues and play an important role in the development and physiological functions of nerve system through the activation of NTs (neurotrophins). As a tyrosine kinase receptor, each TRK will bind to its respective ligand and to activate the downstream signaling pathway. NGF (nerve growth factor) specifically binds to and activates TRKA; TRKB ligand includes BDGF (brain-derived growth factor) and NT-4/5 (neurotrophin-4/5); and NT-3 specifically binds to and activates TRKC. Each of the three TRK receptors contains an extracellular ligand binding domain, transmembrane domain and intracellular kinase domain.

Ligand binding to the corresponding receptors triggers receptor dimerization and activation of the intrinsic cytoplasmic kinase domain and receptor autophosphorylation. The activated receptors initiate diverse signaling pathways such as Ras/MAPK, PLCγ/PKC and PI3K/AKT pathways, and further regulate a series of physiological processes such as proliferation, differentiation, and survival of neuronal cells (Bergman, et al. 1999). The TRK signal pathway is usually precisely regulated, and its abnormal activation thereof closely relates to tumorgenesis (Amatu, et al. 2016). The results show that there are many mechanisms which cause abnormal activation of TRK pathways, including gene fusion, excessive expression of proteins, and single nucleotide mutations. Such abnormal activation closely relates to the pathogenesis of tumors, especially NTRK gene fusion, which has been proven to play an important role in the development of various cancers regardless of tissue sources and types of tumors. With the rapid development of NGS techniques and precision medicine, more and more NTRK fusion genes have been found, such as ETV6-NTRK3, MPRIP-NTRK1, and CD74-NTRK1. Moreover, tumors bearing the NTRK fusion have significant response rate to TRK inhibitors (Drilon, et al. 2018). Therefore, more and more TRK inhibitors have been reported in, such as those in WO2010048314, WO201146336, WO2017004342. At the same time, drug resistance may occur in some treated patients during the clinical trials, and it has been proven that such drug resistance was caused by mutations in the enzymatic domains, such as NTRK1 G595R or G667C mutation, NTRK3 G623R or G696A mutation. The development of new generation of TRK kinase inhibitors is expected to solve these problems.

In summary, there is an urgent need to develop new generation of TRK kinase inhibitors.

SUMMARY OF THE INVENTION

The object of the present invention is to provide a type of novel TRK kinase inhibitors.

In the first aspect of the invention, a compound of formula I is provided:

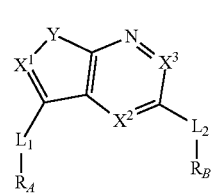

wherein,
$X^1$, $X^2$ and $X^3$ are each independently CR or N;
Y is $NR_1$, wherein the $R_1$ is selected from the group consisting of H, or C1-C6 alkyl which is unsubstituted or substituted with C1-C4 alkyoxy;
R is selected from the group consisting of H, D, —OH, —NH$_2$, halogen and CN; $L_1$ is selected from the group consisting of a substituted or unsubstituted 5-10 membered heterocycloalkylene group comprising 1-3 heteroatoms selected from N, S or O, or a substituted or unsubstituted —$(X^3)_y$—, wherein each $X^3$ is independently selected from the group consisting of: a substituted or unsubstituted $C_1$-$C_8$ alkylene group, —O—, —C(=O)—, —CONH—, —NHCO—, —S—, —S(=O)—, —S(=O)$_2$— and —NH—;
$L_2$ is selected from the group consisting of a substituted or unsubstituted —$(X^4)_z$—, wherein each of the $X^4$ is independently selected from the group consisting of a substituted or unsubstituted $C_1$-$C_8$ alkylene, —O—, —C(=O)—, —S—, —S(=O)—, —S(=O)$_2$—, —NH—, —CONH—, —NHCO—, —NHCONH—, —NHS(=O)—, —NHS(=O)$_2$—;
y is selected from 1 or 2; Z is selected from 0, 1 or 2;
$R_A$ is selected from the group consisting of H, substituted or unsubstituted $C_6$-$C_{10}$ aryl, substituted or unsubstituted 5-10 membered heteroaryl comprising 1-3 heteroatoms selected from N, S or O;
$R_B$ is selected from the group consisting of H, NH$_2$, OH, —COOH, substituted or unsubstituted $C_1$-$C_8$ alkyl, substituted or unsubstituted $C_3$-$C_{10}$ cycloalkyl, substituted or unsubstituted $C_1$-$C_8$ alkoxyl, substituted or unsubstituted $C_6$-$C_{10}$ aryl, substituted or unsubstituted $C_1$-$C_6$ amino, substituted or unsubstituted 5-10 membered heteroaryl comprising 1-3 hetero atoms selected from N, S or O, substituted or unsubstituted 5-12 membered heterocyclic group comprising 1-3 hetero atoms selected from N, S or O (including a monocyclic, bicyclic, spiro or bridged ring);
unless otherwise specified, the "substituted" means that a group is substituted by one or more (e.g., 2, 3, 4, etc.) substituents selected from the group consisting of a halogen, C1-C6 alkyoxy, halogenated C1-C6 alkyl, halogenated C1-C6 alkyoxyl, halogenated C3-C8 cycloalkyl, benzyloxy, methyl sulfuryl, —S(=O)₂NH₂, oxo (=O), —CN, hydroxy, —NH₂, carboxyl, C1-C6 amido(—C(=O)—N(Rc)₂ and —NH—C(=O)(Rc), Rc is H or C1-C5 alkyl), C1-C6 alkyl-(C1-C6 amido),

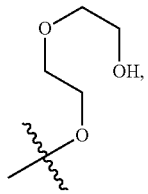 [SMILES: *OCCOCCO]

or a substituted or unsubstituted group selected from the group consisting of C1-C6 alkyl, C3-C8 cycloalkyl, C1-C6 amido, C1-C6 amide, C6-C10 aryl, 5-10 membered heteroaryl comprising 1-3 heteroatoms selected from N, S or O, 3-12 membered heterocyclic group comprising 1-3 heteroatoms selected from N, S or O (including a monocyclic, bicyclic, spiro or bridged ring), —(CH₂)—C₆-C₁₀ aryl, —(CH₂)-(5-10 membered heteroaryl comprising 1-3 heteroatoms selected from N, S or O), wherein the substituent is selected from the group consisting of a halogen, C1-C6 alkoxyl, halogenated C1-C6 alkyl, halogenated C1-C6 alkoxyl, halogenated C3-C8 cycloalkyl, methyl sulfuryl, —S(=O)₂NH₂, oxo (=O), —CN, hydroxyl, —NH₂, carboxyl, C1-C6 amido (—C(=O)—N(Rc)₂ or —NH—C(=O)(Rc), Rc is H or C1-C5 alkyl), C1-C6 alkyl-(C1-C6 amido),

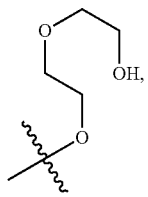 [SMILES: *OCCOCCO]

C1-C6 alkyl, C3-C8 cycloalkyl, C1-C6 amine group, C6-C10 aryl, 5-10 membered heteroaryl comprising 1-3 heteroatoms selected from N, S or O, 3-12 membered heterocyclic group comprising 1-3 heteroatoms selected from N, S or O (including a monocyclic, bicyclic, spiro or bridged ring), —(CH₂)—C6-C10 aryl, —(CH₂)-(5-10 membered heteroaryl comprising 1-3 heteroatoms selected from N, S, or O);

⸹ is the connection site of the group;

with the proviso that compounds of formula I are chemical stable structures.

In another preferred example, the compound of formula I is of the following structure:

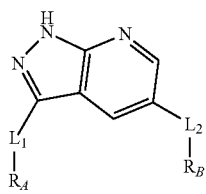

In another preferred embodiment, $L_1$ is a substituted or unsubstituted 5-10 membered heterocyclylene comprising 1-3 heteroatoms selected from N, S and O; preferably, $L_1$ is a substituted or unsubstituted 5-7 membered heterocyclylene comprising 1 or 2 N atoms.

In another preferred example, $R_A$ and $R_B$ are connected to form a group selected from the group consisting of substituted or unsubstituted C1-C8 alkylene, substituted or unsubstituted C1-C8 alkylene-O—, substituted or unsubstituted C1-C8 alkylene-O—, substituted C1-C8 alkylene-(5-10 membered heteroaryl comprising 1-3 heteroatoms selected from N, S and O), substituted or unsubstituted C1-C8 alkylene-O-(5-10 membered heteroaryl comprising 1-3 heteroatoms selected from N, S and O), substituted or unsubstituted C1-C8 alkylene-(5-10 membered heterocyclic group comprising 1-3 selected from N, S and O), substituted or unsubstituted C1-C8 alkylene-O-(5-10 membered heterocyclic group comprising 1-3 heteroatoms selected from N, S and O).

In another preferred example, the $L_1$ is selected from the group consisting of:

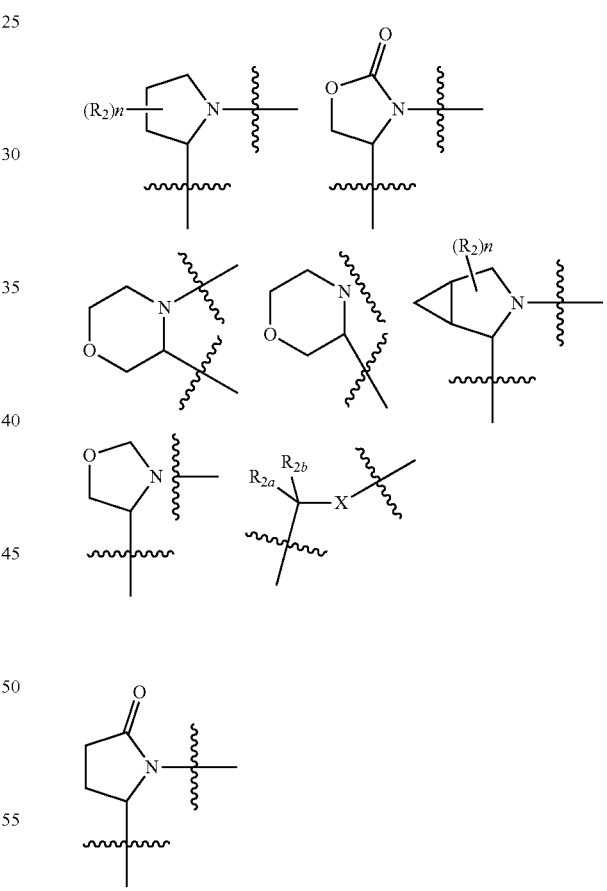

n is selected from the group consisting of 0, 1, 2 and 3;

$R_2$, $R_{2a}$ and $R_{2b}$ are each independently selected from the group consisting of H, OH, halogen, substituted or unsubstituted $C_1$-$C_8$ alkyl;

X is selected from the group consisting of NH, O, —CONH—, —NHCO—, S, —S(=O)₂—, —NHS (=O)—, —NHS(=O)₂—;

$R_A$ is

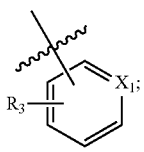

wherein the ⇝ is the connection site of $R_A$ and $L_1$;
$L_2$ is

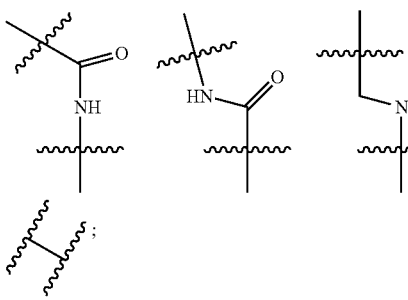

$R_B$ is

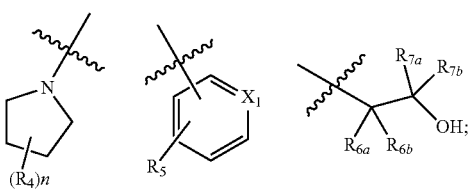

wherein the ⇝ is the connection site of $R_B$ and $L_2$;
$R_3$ is selected from the group consisting of H, halogen, C1-C6 alkoxyl, halogenated C1-C6 alkyl, halogenated C1-C6 alkoxyl;
$R_4$ and $R_5$ are each independently selected from the group consisting of H, OH, halogen, C1-C6 alkyl-OH, $C_1$-$C_6$ alkoxyl, $C_1$-$C_6$ alkyl amine group, $C_1$-$C_6$ alkyl amido, —($C_1$-$C_6$ alkyl)-NH—($C_1$-$C_6$ alkyl), —($C_1$-$C_6$ alkyl amido)-($C_1$-$C_6$ alkyl);
$R_{6a}$, $R_{6b}$, $R_{7a}$, $R_{7b}$ are each independently selected from the group consisting of H, OH, halogen; or $R_{6a}$, $R_{6b}$, $R_{7a}$, $R_{7b}$ together with carbon atoms to which they are connected form a 5-12 membered heterocyclic group comprising 1-3 heteroatoms selected from N, S or O.

In another preferred embodiment, the compound has the structure shown in the following formula II:

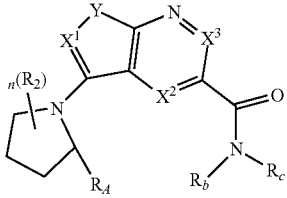

II wherein the Rb and Rc are selected from the group consisting of H, substituted or unsubstituted $C_1$-$C_8$ alkyl, substituted or unsubstituted $C_3$-$C_8$ cycloalkyl, said Rb and Rc and adjacent N atoms together form a substituted or unsubstituted 5-12 membered heterocyclic group (including monocyclic, bicyclic, spiro or bridged ring);

In another preferred embodiment, the compound has the structure shown in the following formula III:

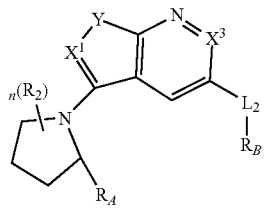

III

In another preferred embodiment, the compound has the structure shown in the following formula:

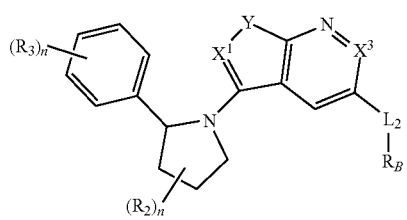

In another preferred embodiment, the compound has the structure shown in the following formula:

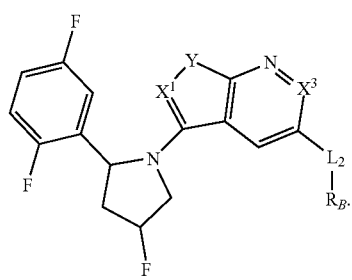

In another preferred embodiment, the compound has the structure shown in the following formula:

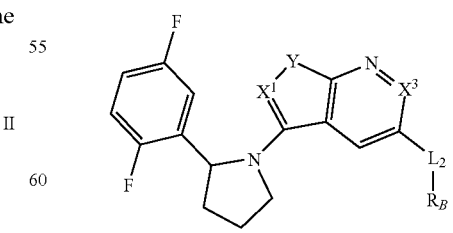

In another preferred embodiment, the compound has the structure selected from the following group.

In the second aspect of the invention, a pharmaceutical composition is provided, comprising (1) a compound according to the first aspect of the invention, or a stereoisomer or tautomer thereof, or a pharmaceutically acceptable salt, hydrate or solvate thereof; (2) pharmaceutically acceptable carriers.

In another preferred embodiment, the pharmaceutical composition is an injection, capsule, tablet, pill, powder or granule.

In another preferred embodiment, the disease is selected from the group consisting of cancers, proliferative diseases, pain, skin diseases or conditions, metabolic diseases, muscle diseases, neurological diseases, autoimmune diseases, itching caused by dermatitis, inflammation related diseases, bone related diseases.

In another preferred embodiment, the cancer is selected from the group consisting of TRK function abnormalities (abnormal activation functions induced by TRK gene amplification, overexpression, mutation or gene fusion) related cancers (including, but not limited to): neuroblastoma, prostate cancer, thyroid cancer, lung cancer, ovarian cancer, pancreatic cancer, colorectal cancer, non-small cell lung cancer, fibrosarcoma, etc.

In the third aspect of the invention, a use of the compound of the present invention or a stereoisomer or a tautomer thereof, or a pharmaceutically acceptable salt, hydrate or solvate thereof, or pharmaceutical compositions according to the second aspect of the invention is provided, in the preparation of pharmaceutical compositions for preventing and/or treating diseases related to TRK function abnormalities (abnormal activation functions induced by TRK gene amplification, overexpression, mutation or gene fusion).

In another preferred embodiment, the disease is selected from the group consisting of cancers, proliferative diseases, pain, skin diseases or conditions, metabolic diseases, muscle diseases, neurological diseases, autoimmune diseases, itching caused by dermatitis.

In the fourth aspect of the invention, a TRK inhibitor is provided, which comprises the compound, or a stereoisomer thereof, a tautomer thereof, or a pharmaceutically acceptable salt, hydrate or solvent thereof of the first aspect of the present invention.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Terms

Unless otherwise defined, all technical and scientific terms used herein have the same meaning as commonly understood by one of ordinary skill in the art to which this invention belongs.

As used herein, when used in reference to a particular recited value, the term "about" means that the value can vary by no more than 1% from the recited value. For example, as used herein, the expression "about 100" includes all the values between 99 and 101 (e.g., 99.1, 99.2, 99.3, 99.4, etc.).

As used herein, the terms "containing" or "including (comprising)" may be an open-ended form, semi-close-ended form, or close-ended form. In other words, the terms also include "essentially consisting of . . . " or "consisting of . . . ".

Definitions

As used herein, the term "alkyl" includes straight or branched alkyl groups. For example, $C_1$-$C_8$ alkyl refers to straight or branched alkyls having from 1-8 carbon atoms, such as methyl, ethyl, propyl, isopropyl, butyl, isobutyl, tert-butyl, and the like.

As used herein, the term "alkenyl" includes straight or branched alkenyl groups. For example, $C_2$-$C_6$ alkenyl refers to straight or branched alkenyl groups having 2-6 carbon atoms, such as vinyl, allyl, 1-propenyl, isopropenyl, 1-butenyl, 2-butenyl, and the like.

As used herein, the term "alkynyl" includes straight or branched alkynyl groups. For example, "$C_2$-$C_6$ alkynyl" refers to straight or branched alkynyls having 2-6 carbon atoms, such as ethynyl, propynyl, butynyl, and the like.

As used herein, the term "$C_3$-$C_8$ cycloalkyl" refers to cycloalkyl groups having 3 to 8 carbon atoms. It may be a monocyclic ring, such as cyclopropyl, cyclobutyl, cyclopentyl, cyclohexyl, and the like. It may also be of a bicyclic form, such as a bridged or spiro ring form.

As used herein, the term "$C_1$-$C_8$ alkoxyl" refers to straight or branched alkoxyl groups having 1-8 carbon atoms; for example, methoxy, ethoxy, propoxy, isopropoxy, butoxy, isobutoxy, tert-butoxy, and the like.

As used herein, the term "3-12 membered heterocyclo group comprising 1-3 heteroatoms selected from the group consisting of N, S and O" refers to a saturated or partially saturated cyclic group comprising 3-12 ring atoms, among which 1-3 atoms are heteroatoms selected from the group consisting of N, S and O. It may be a monocyclic ring or bicyclic form, such as a bridged or spiro ring form. Specific examples may be oxetane, azetidine, tetrahydro-2H-pyranyl, piperidinyl, tetrahydrofuranyl, morpholinyl and pyrrolidinyl, and the like.

As used herein, the term "$C_6$-$C_{10}$ aryl" refers to aryl groups comprising 6 to 10 carbon atoms, such as phenyl, naphthyl, and the like.

As used herein, the term "5-10 membered heteroaryl comprising 1-3 heteroatoms selected from the group consisting of N, S and O" refers to cyclic aromatic groups comprising 5-10 atoms, among which 1-3 atoms are heteroatoms selected from the group consisting of N, S and O. It may be a monocyclic ring or fused ring form. Specific examples may be pyridyl, pyridazinyl, pyrimidinyl, pyrazinyl, triazinyl, pyrrolyl, pyrazolyl, imidazolyl, (1,2,3)-triazolyl and (1,2,4)-triazolyl, tetrazyl, furyl, thienyl, isoxazolyl, thiazolyl, oxazolyl, etc.

Unless otherwise specified, all the groups of the present invention may be substituted with a substituent selected from the group consisting of a halogen, nitrile, nitro, hydroxy, amino, $C_1$-$C_6$ alkyl-amine group, $C_1$-$C_6$ alkyl, $C_2$-$C_6$ alkenyl, $C_2$-$C_6$ alkynyl, $C_1$-$C_6$ alkoxyl, halogenated $C_1$-$C_6$ alkyl, halogenated $C_2$-$C_6$ alkenyl, halogenated $C_2$-$C_6$ alkynyl, halogenated $C_1$-$C_6$ alkoxyl, allyl, benzyl, $C_6$-$C_{12}$ aryl, $C_1$-$C_6$ alkoxyl-$C_1$-$C_6$ alkyl, $C_1$-$C_6$ alkoxyl-carbonyl, phenoxycarbonyl, $C_2$-$C_6$ alkynyl-carbonyl, $C_2$-$C_6$ alkenyl-carbonyl, $C_3$-$C_6$ cycloalkyl-carbonyl, $C_1$-$C_6$ alkyl-sulfonyl, etc.

As used herein, "halogen" or "halogen atom" refers to F, Cl, Br, or I. More preferably, said halogen or halogen atom is selected from F, Cl or Br. "Halogenated" means that a group is substituted by atoms selected from the group consisting of F, Cl, Br and I.

Unless otherwise specified, the structural formula described herein are intended to include all isomeric forms (such as enantiomeric, diastereomeric, and geometric isomers (or conformational isomers)): for example, R, S configuration of asymmetrical centers, (Z), (E) isomers of double bonds, etc. Therefore, a mixture of single stereochemical isomers or enantiomers, diastereomers or geometric isomers (or conformers) of the compounds of the invention falls within the scope of the invention.

As used herein, the term "tautomer" means that structural isomers having different energies can exceed the low energy barrier and thereby transform between each other. For example, proton tautomers (proton shift) includes interconversion by proton transfer, such as 1H-carbazole and 2H-carbazole. Valence tautomers include interconversion through the recombination of some bonding electrons.

As used herein, the term "solvate" refers to a complex formed by a compound of the invention coordinating to a solvent molecule at a specific ratio.

Compound of Formula I

The present invention provides a compounds as shown in Formula I:

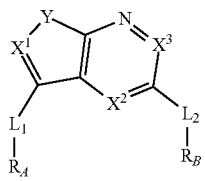

wherein, $X^1$, $X^2$ and $X^3$ are each independently CR or N;

Y is $NR_1$, wherein the $R_1$ is selected from the group consisting of H, or C1-C6 alkyl which is unsubstituted or substituted with C1-C4 alkyoxy;

R is selected from the group consisting of H, D, —OH, —$NH_2$;

$L_1$ is selected from the group consisting of a substituted or unsubstituted 5-10 membered heterocycloalkylene group comprising 1-3 heteroatoms selected from N, S or O, or substituted or unsubstituted —$(X^3)_y$—, wherein each $X^3$ is independently selected from the group consisting of: a substituted or unsubstituted $C_1$-$C_8$ alkylene group, —O—, —C(=O)—, —CONH—, —NHCO—, —S—, —S(=O)—, —S(=O)$_2$— and —NH—;

$L_2$ is selected from the group consisting of a substituted or unsubstituted —$(X^4)_z$—, wherein each of the $X^4$ is independently selected from the group consisting of a substituted or unsubstituted $C_1$-$C_8$ alkylene, —O—, —C(=O)—, —S—, —S(=O)—, —S(=O)$_2$—, —NH—, —CONH—, —NHCO—, —NHCONH—, —NHS(=O)—, —NHS(=O)$_2$—;

y is selected from 1 or 2; z is selected from 0, 1 or 2;

$R_A$ is selected from the group consisting of H, substituted or unsubstituted $C_6$-$C_{10}$ aryl, substituted or unsubstituted 5-10 membered heteroaryl comprising 1-3 heteroatoms selected from N, S or O;

$R_B$ is selected from the group consisting of H, $NH_2$, OH, —COOH, substituted or unsubstituted $C_1$-$C_8$ alkyl, substituted or unsubstituted $C_3$-$C_{10}$ cycloalkyl, substituted or unsubstituted $C_1$-$C_8$ alkoxyl, substituted or unsubstituted $C_6$-$C_{10}$ aryl, substituted or unsubstituted C1-C6 amino, substituted or unsubstituted 5-10 membered heteroaryl comprising 1-3 heteroatoms selected from N, S or O, substituted or unsubstituted 5-10 membered heterocyclic group comprising 1-3 heteroatoms selected from N, S or O (including a monocyclic, bicyclic, spiro or bridged ring);

unless otherwise specified, the "substituted" means that a group is substituted by one or more (e.g., 2, 3, 4, etc.) substituents selected from the group consisting of a halogen, C1-C6 alkoxyl, halogenated C1-C6 alkyl, halogenated C1-C6 alkoxyl, halogenated C3-C8 cycloalkyl, methyl sulfuryl, —S(=O)$_2NH_2$, oxo (=O), —CN, hydroxy, —$NH_2$, carboxyl, C1-C6 amide (—C(=O)—N(Rc)$_2$ or —NH—C(=O)(Rc), Rc is H or C1-C5 alkyl), C1-C6 alkyl-(C1-C6 amide),

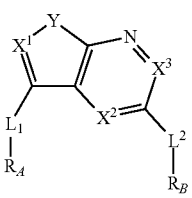

or a substituted or unsubstituted group selected from the group consisting of a C1-C6 alkyl, C3-C8 cycloalkyl, C1-C6 amido, C6-C10 aryl, 5-10 membered heteroaryl comprising 1-3 heteroatoms selected from N, S, or O, 5-12 membered heterocyclic ring group comprising 1-3 heteroatoms selected from N, S or O (including a monocyclic, bicyclic, spiro or bridged ring), —($CH_2$)—C6-C10 aryl, —($CH_2$)-(5-10 membered heteroaryl having 1-3 heteroatoms selected from N, S, or O), wherein the substituent is selected from the group consisting of a halogen, C1-C6 alkyl, halogenated C1-C6 alkyl, halogenated C1-C6 alkoxyl, halogenated C3-C8 cycloalkyl, benzyloxy, methyl sulfuryl, —S(=O)$_2NH_2$, oxo (=O), —CN, hydroxy, —$NH_2$, carboxy, C1-C6 amide (—C(=O)—N(Rc)$_2$ or —NH—C(=O)(Rc), wherein Rc is H or C1-C5 alkyl), C1-C6 alkyl-(C1-C6 amide),

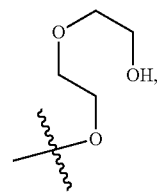 [SMILES: *OCCOCCO]

C1-C6 alkyl, C3-C8 cycloalkyl, C1-C6 amino, C1-C6 amide, C6-C10 aryl, 5-10 membered heteroaryl having 1-3 heteroatoms selected from N, S, or O, 5-12 membered heterocyclic ring group comprising 1-3 heteroatoms selected from N, S or O (including a monocyclic, bicyclic, spiro or bridged ring), —($CH_2$)—C6-C10 aryl, —($CH_2$)-(5-10 membered heteroaryl having 1-3 heteroatoms selected from N S, or O);

⁔ is the connection site of the group;

with the proviso that compounds of formula I are chemical stable structures.

In another preferred embodiment, $X^1$, $X^2$, $X^3$, $L_1$, $L_2$, $R_A$ and $R_B$ are each independently the corresponding group of the compound in the examples.

In another preferred embodiment the compound is selected from the following group.
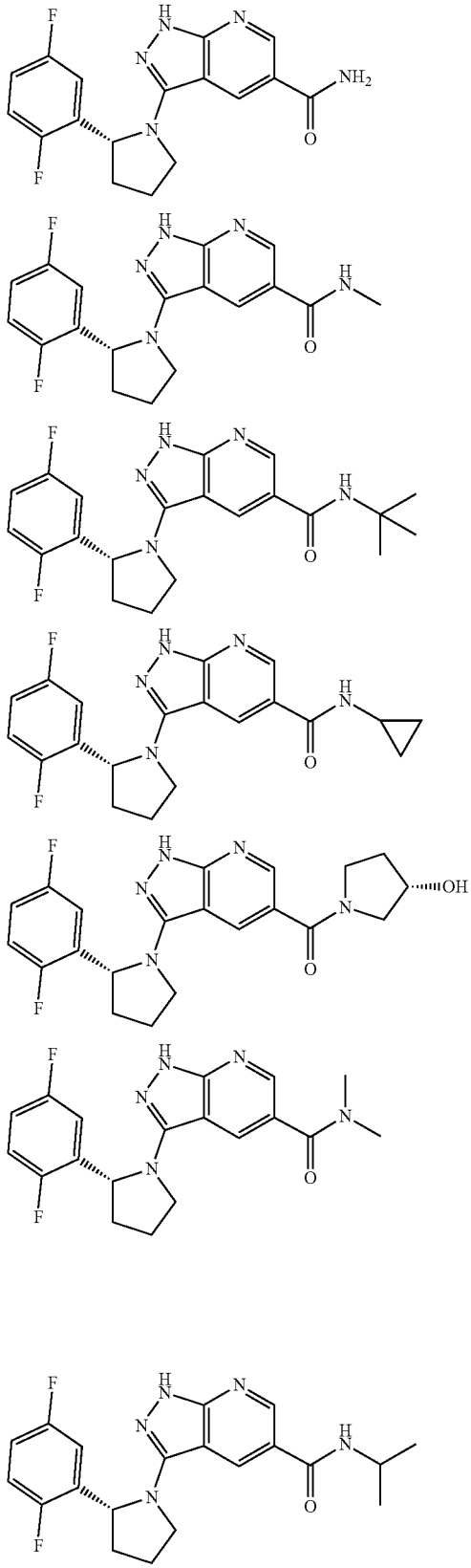
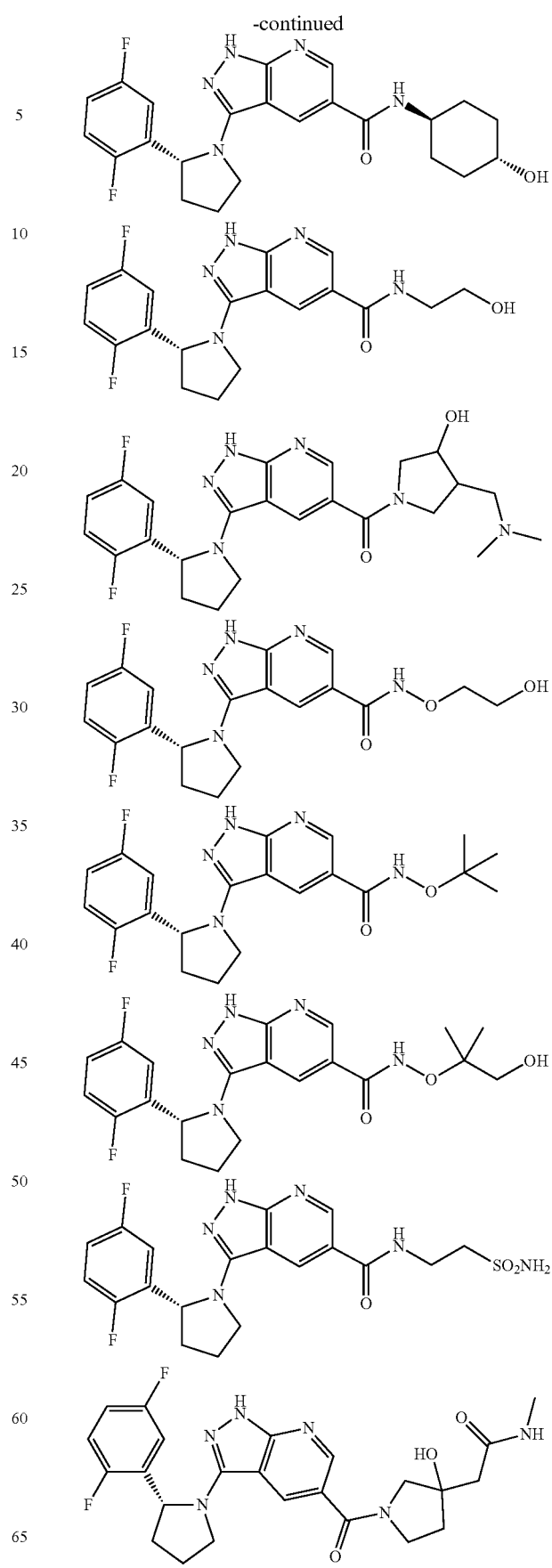

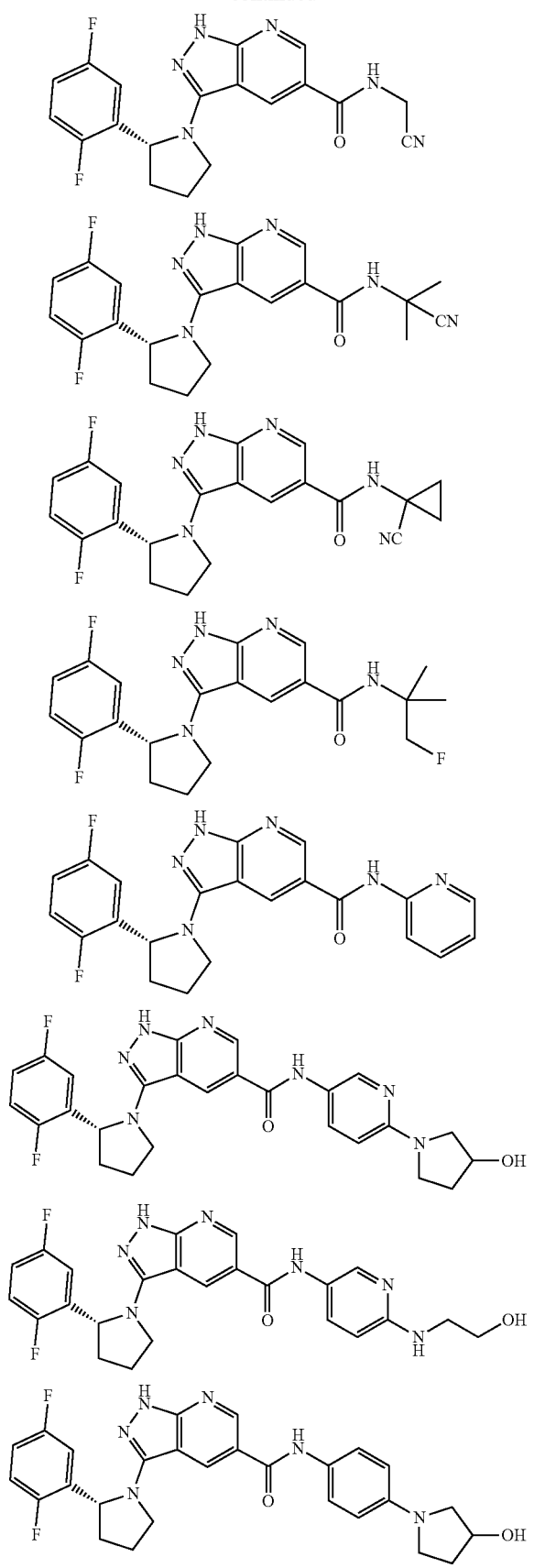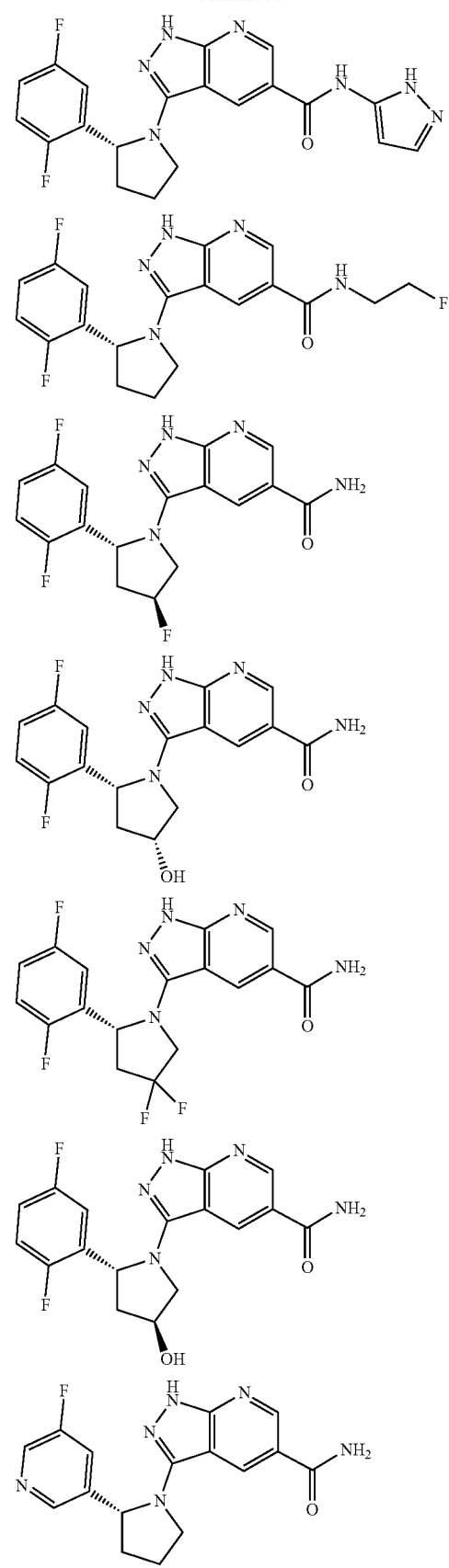

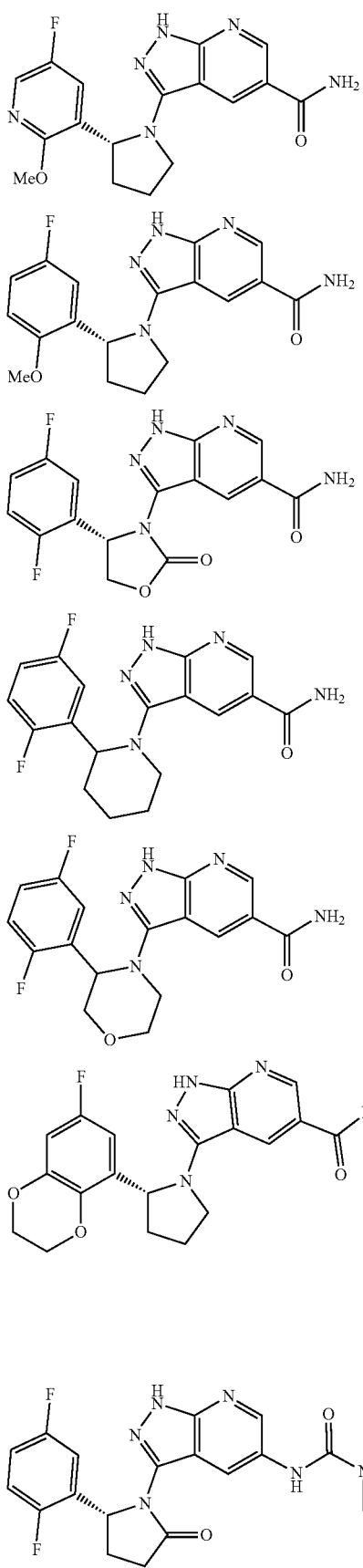
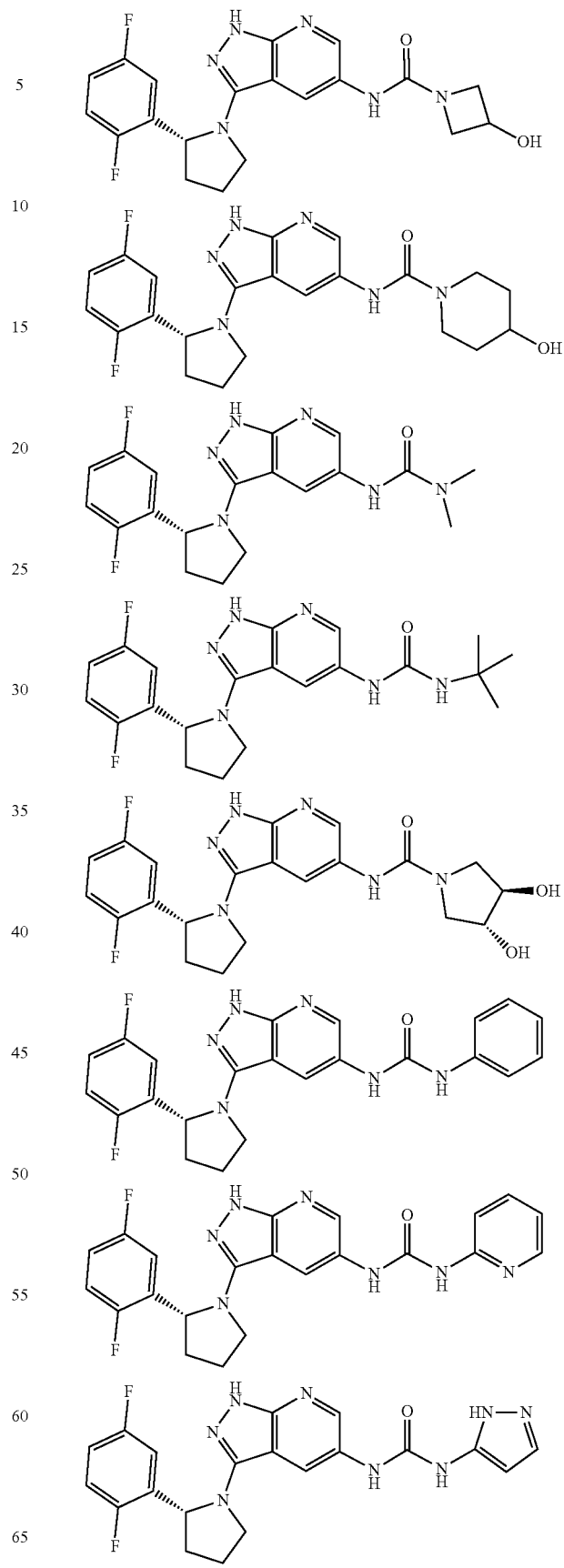

17
-continued
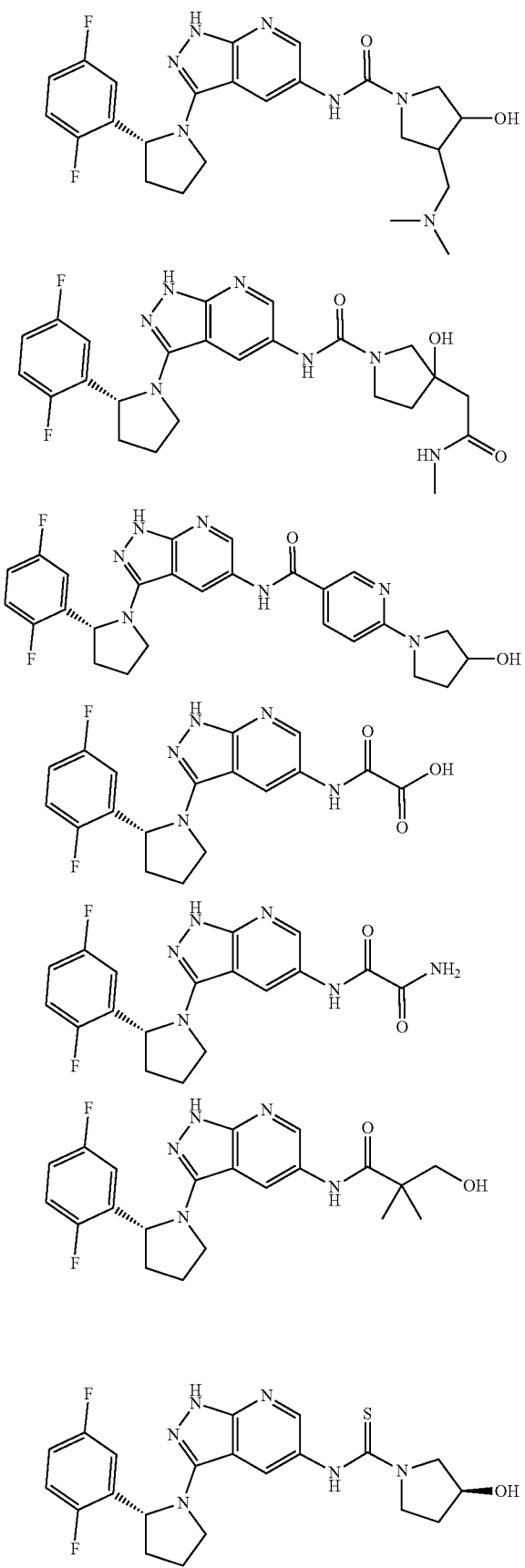
18
-continued
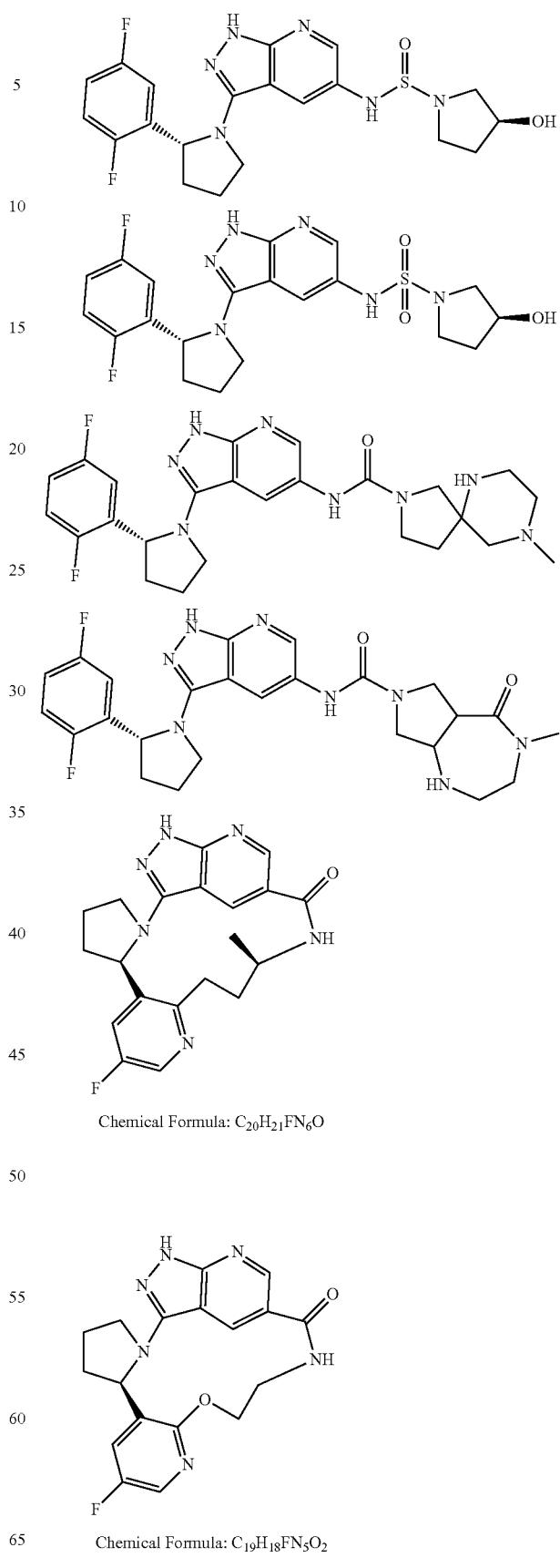
Chemical Formula: $C_{20}H_{21}FN_6O$
Chemical Formula: $C_{19}H_{18}FN_5O_2$ -continued
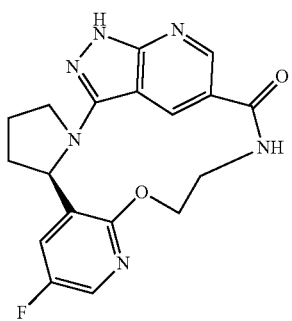
Chemical Formula: $C_{18}H_{17}FN_6O_2$
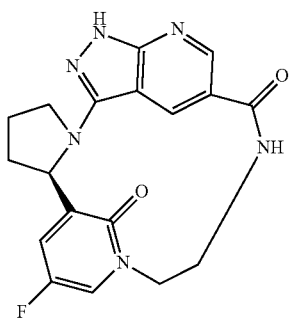
Chemical Formula: $C_{18}H_{17}FN_6O_2$
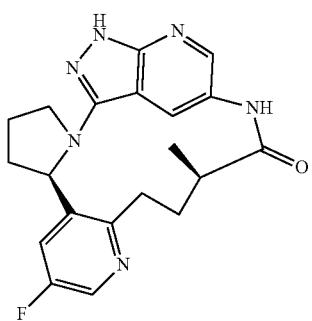
Chemical Formula: $C_{20}H_{21}FN_6O$
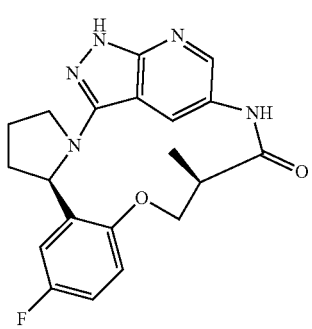
Chemical Formula: $C_{20}H_{20}FN_5O_2$
-continued
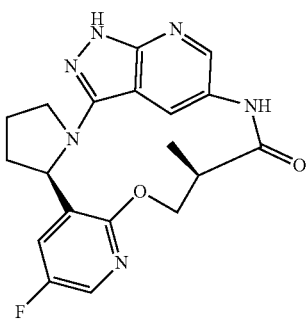
Chemical Formula: $C_{19}H_{19}FN_6O_2$
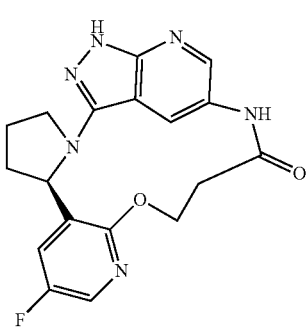
Chemical Formula: $C_{18}H_{17}FN_6O_2$
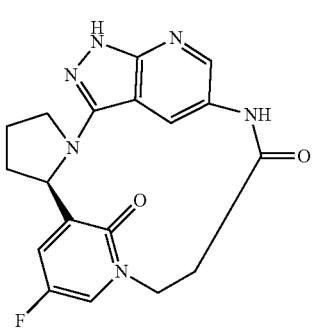
Chemical Formula: $C_{18}H_{17}FN_6O_2$
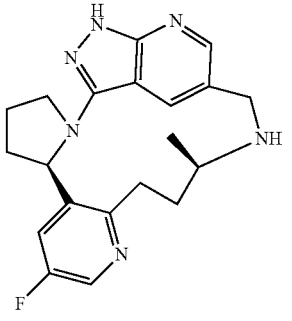
Chemical Formula: $C_{20}H_{23}FN_6$ -continued
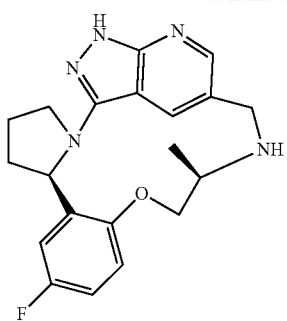
Chemical Formula: C₂₀H₂₂FN₅O
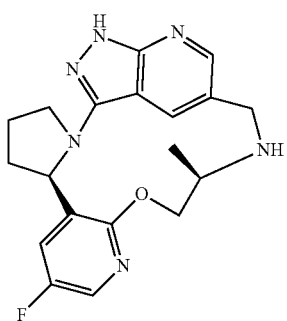
Chemical Formula: C₁₉H₂₁FN₆O
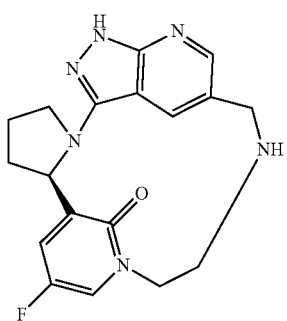
Chemical Formula: C₁₈H₁₉FN₆O
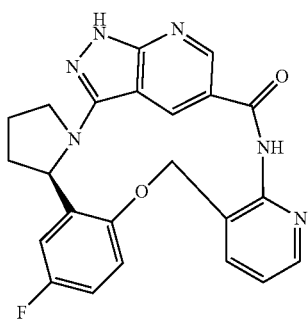
Chemical Formula: C₂₃H₁₉FN₆O₂
-continued
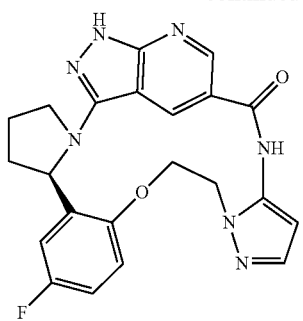
Chemical Formula: C₂₂H₂₀FN₇O₂
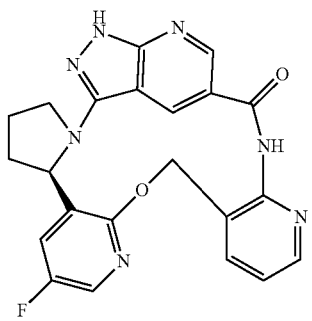
Chemical Formula: C₂₂H₁₈FN₇O₂
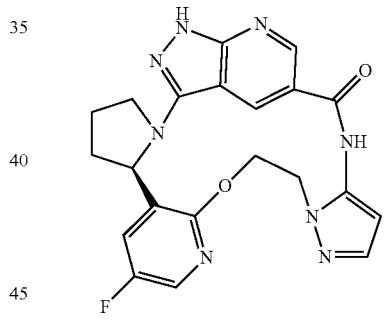
Chemical Formula: C₂₁H₁₉FN₈O₂
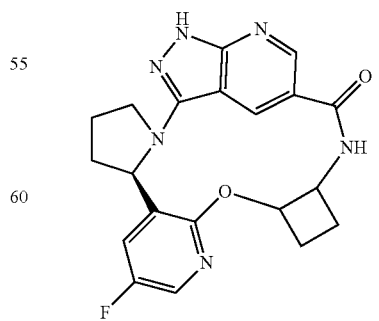
Chemical Formula: C₂₁H₂₀FN₆O₂

23

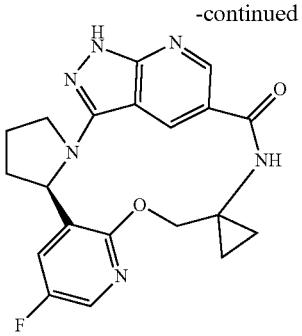

Chemical Formula: $C_{21}H_{20}FN_5O_2$

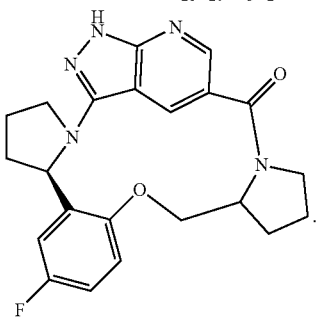

Chemical Formula: $C_{22}H_{22}FN_5O_2$

In another preferred embodiment, the formula I compound of the present invention is any compound prepared in the examples.

Preparation of Compound of Formula I

The compound of the formula I of the present invention can be prepared by the following method:

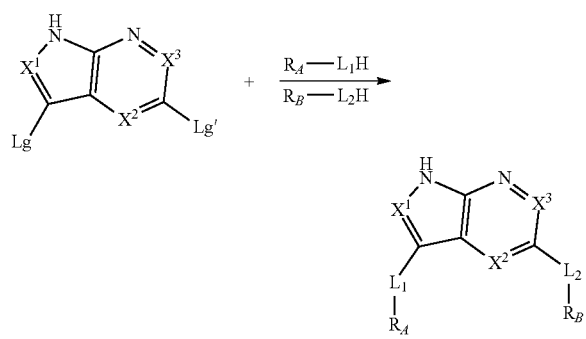

wherein Lag and Lg' are leaving groups, preferably Tf, fluorine, chlorine, bromine or iodine.

Pharmaceutical Composition and Administration Thereof

The compounds of the present invention possess outstanding activity of inhibiting TRK kinase. Therefore, the compound of the present invention, and the crystal forms, pharmaceutically acceptable inorganic or organic salts, hydrates or solvates thereof, and the pharmaceutical composition comprising the compound of the present invention as a main active ingredient can be used for preventing or treating diseases related to activity or expression of TRK kinase (e.g., cancers).

The pharmaceutical composition of the invention comprises the compound of the present invention in a safe and effective dosage range and pharmaceutically acceptable excipients or carriers. Wherein the "safe and effective dosage" means that the amount of compound is sufficient to significantly ameliorate the condition without causing significant side effects. Generally, the pharmaceutical composition contains 1-2000 mg of the compound of the invention per dose, preferably, 10-200 mg of the compound of the invention per dose. Preferably, the "dose" is a capsule or tablet.

"Pharmaceutically acceptable carrier" means one or more compatible solid or liquid fillers, or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation on administration mode for the compound or pharmaceutical compositions of the present invention, and the representative administration mode includes (but is not limited to): oral, parenteral (intravenous, intramuscular or subcutaneous) administration.

Solid dosage forms for oral administration include capsules, tablets, pills, powders and granules. In these solid dosage forms, the active compounds are mixed with at least one conventional inert excipient (or carrier), such as sodium citrate or CaHPO4, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or a combination thereof.

Besides these inert diluents, the composition may also contain additives such as wetting agents, emulsifiers, and suspending agent, sweetener, flavoring agents and perfume.

In addition to the active compounds, the suspension may contain a suspending agent, for example, ethoxylated isooctadecanol, polyoxyethylene sorbitol and sorbitan esters, microcrystalline cellulose, methanol aluminum and agar, or a combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

Compounds of the present invention can be administrated alone, or in combination with any other pharmaceutically acceptable compounds.

In the case of co-administration, the pharmaceutical composition can also include one or more other pharmaceutically acceptable compounds. The one or more other pharmaceutically acceptable compounds may be administered simultaneously, separately or sequentially with the compound of the present invention.

When the pharmaceutical compositions are used, a safe and effective amount of compound of the present invention is applied to a mammal (such as human) in need of, wherein the dose of administration is a pharmaceutically effective dose. For a person weighed 60 kg, the daily dose is usually 1-2000 mg, preferably 20-500 mg. Of course, the particular dose should also depend on various factors, such as the route of administration, patient healthy status, which are well within the skills of an experienced physician.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

Synthesis of Intermediate A

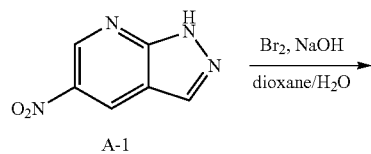

A-1

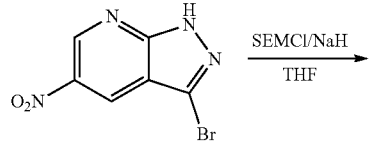

A-2

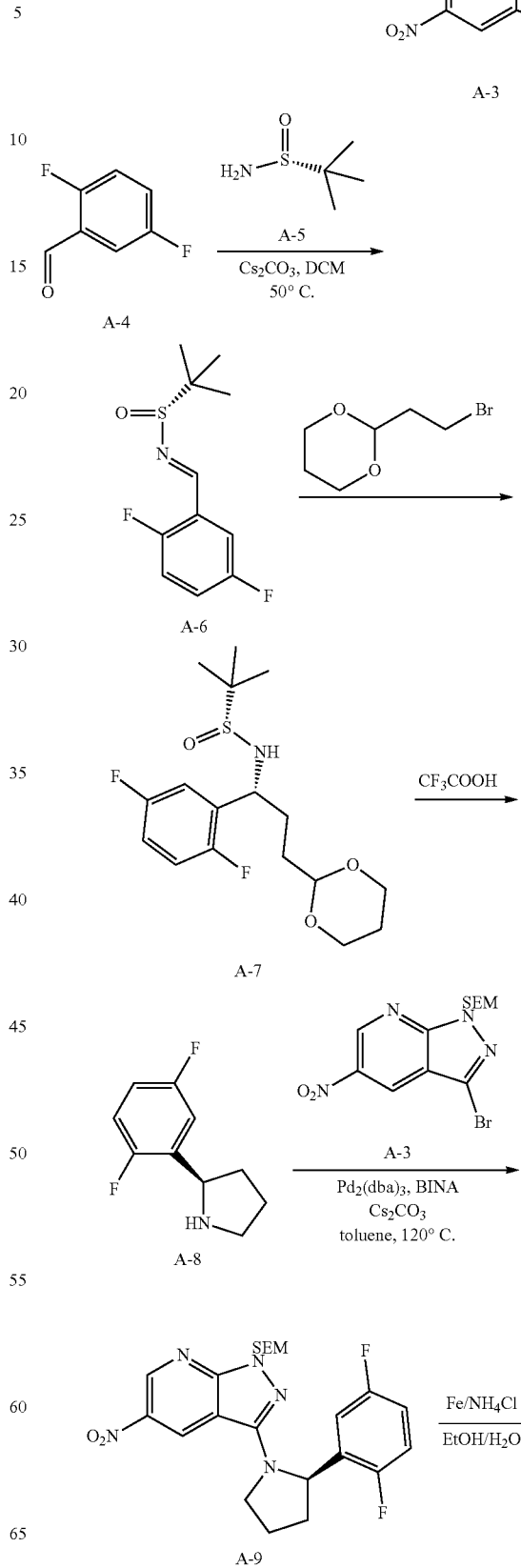

-continued

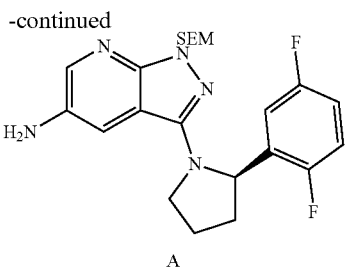

A (R)—N-(2,5-Difluorobenzylidene)-2-methylpropan-2-sulfinamide

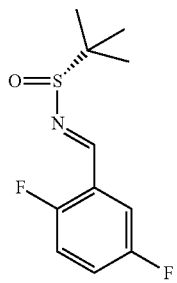 [SMILES: CC(C)(C)[S@@](=O)/N=C/c1cc(F)ccc1F]

2,5-Difluorobenzaldehyde (5 g, 35.2 mmol) and (R)-2-methylpropan-2-sulfinamide (4.47 g, 36.9 mmol) were dissolved in dichloromethane (50 mL), and cesium carbonate (8.0 g, 24.6 mmol) was added at room temperature. The solution was warmed to 50° C. to react for 3 h. TLC showed that the reaction was completed. The solution was filtered, the residue was washed with dichloromethane, and the combined filtrate was washed with brine, dried over $Na_2SO_4$, and concentrated to afford (R)—N-(2,5-difluorzylmethylene)-2-methylpropane-2-sulfamide as a yellow liquid (9 g).

(R)—N—((R)-1-(2,5-Difluorophenyl)-3-(1,3-dioxan-2-yl)propyl)-2-methylpropane-2-sulfinamide

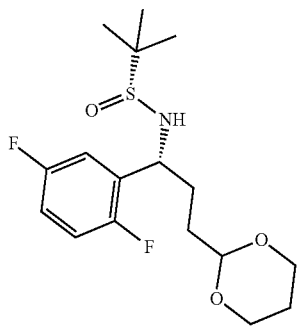 [SMILES: CC(C)(C)[S@@](=O)N[C@H](CCC1OCCCO1)c1cc(F)ccc1F]

To a suspension of magnesium granules (2 g, 83.3 mmol) in dry tetrahydrofuran (72 mL) under nitrogen atmosphere at 40° C., Dibal-H (0.1 mL, 1.5 m, 0.15 mmol) was added dropwise, and the mixture was allowed to react at 40° C. for 0.5 h. Then 2-(2-bromoethyl)-1,3-dioxane (14.3 g, 73.47 mmol) in tetrahydrofuran (40 ml) was slowly added to the system and the temperature was controlled at 40-50° C., and upon addition, the system was kept at 40° C. and stirred for 1 h. The reaction system was cooled to −30° C., then (R,E)-N-(2,5-difluorobenzylidene)-2-methylpropan-2-sulfinamide (9 g, 36.73 mmol) in tetrahydrofuran (40 mL) was added dropwise to the mixture, and the temperature was controlled at −30° C.-20° C. After addition, the mixture was stirred at −30° C. for 2 h. After TLC showed that the reaction was completed, the reaction was quenched with 10% aqueous citric acid solution and the inner temperature was controlled at 10° C. After extracted with dichloromethane, the organic phase was washed with saturated brine, dried over $Na_2SO_4$ and the filtrate was concentrated to afford (R)—N—((R)-1-(2,5-difluorophenyl)-3-(1,3-dioxan-2-yl)propyl)-2-methylpropane-2-sulfinamide as colorless liquid (15.8 g).

(R)-2-(2,5-Difluorophenyl)pyrrolidine

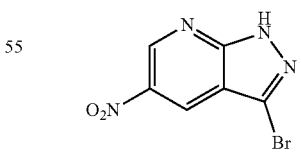

A mixture of (R)—N—((R)-1-(2,5-Difluorophenyl)-3-(1,3-dioxan-2-yl)propyl)-2-methylpropan-2-sulfinamide (15.8 g, 43.76 mmol) in trifluoroacetic acid (32 mL) and water (8 mL) was stirred at room temperature for 1 h. Then another portion of trifluoroacetic acid (60 mL) was added dropwise to the mixture followed by triethylsilane (15.2 g, 131.1 mmol) and the mixture was allowed to react at room temperature for overnight. LC-MS showed that the reaction was completed, and the reaction mixture was concentrated under vacuum. The residue was diluted in hydrochloric acid (1N, 100 mL) and stirred for 0.5 hours. The resulting mixture was extracted with methyl tert-butyl ether, and the organic phase was washed with hydrochloric acid (1N, 50 mL). The combined aqueous phase was adjusted to pH=11 with aqueous sodium hydroxide solution, then extracted with dichloromethane. The combined organic phase was washed with saturated brine and dried over anhydrous sodium sulfate, and the filtrate was concentrated to afford (R)-2-(2,5-difluorophenyl)pyrrolidine as liquid (6.7 g).

3-Bromo-5-nitro-1H-pyrazolo[3,4-b]pyridine

To a mixture of 5-nitro-1H-pyrazolo[3,4-b]pyridine (500 mg, 3.05 mmol) in doxane (20 mL) and $H_2O$ (5 mL) was added NaOH (488 mg, 12.19 mmol) at 0° C. $Br_2$ (1.9 g, 12.19 mmol) was added drop wise. The mixture was stirred at r.t. for 0.5 h. After the reaction was completed, EtOAc was added and the mixture was washed with aq. $NaHCO_3$ solution. The organic layer was separated and concentrated.

The residue was purified by column chromatography to afford the desired product (530 mg, yield 72%) as a yellow solid.

3-Bromo-5-nitro-1-((2-(trimethylsilyl)ethoxy)methyl)-1H-pyrazolo[3,4-b]pyridine

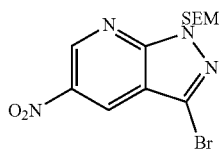 [SMILES: C[Si](C)(C)CCOCn1nc(Br)c2cc([N+](=O)[O-])cnc21]

To a mixture of 3-bromo-5-nitro-TH-pyrazolo[3,4-b]pyridine (530 mg, 2.18 mmol) in THF (2 mL) was added NaH (175 mg, 4.36 mmol) slowly at 0° C. The mixture was stirred at 0° C. for 0.5 h. SEMCl (545 mg, 3.27 mmol) was added and stirred for 0.5 h. The reaction was quenched with ice-water and extracted with EtOAc. The organic layer was dried over $NaSO_4$ and concentrated. The residue was purified by column chromatograpgy (petroluenm ether/EtOAc=5/1) to afford the desired product (560 mg, yield 69%) as a yellow solid.

(R)-3-(2-(2,5-Difluorophenyl)pyrrolidin-1-yl)-5-nitro-1-((2-(trimethylsilyl)ethoxy)methyl)-1H-pyrazolo[3,4-b]pyridine

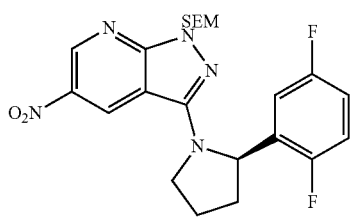 [SMILES: C[Si](C)(C)CCOCn1nc(N2CCC[C@@H]2c2cc(F)ccc2F)c2cc([N+](=O)[O-])cnc21]

A mixture of 3-bromo-5-nitro-1-((2-(trimethylsilyl)ethoxy)methyl)-1H-pyrazolo[3,4-b]pyridine (560 mg, 1.50 mmo), (R)-2-(2,5-difluorophenyl)pyrrolidine (275 mg, 1.50 mmol), $Pd_2(dba)_3$ (137 mg, 0.15 mmol), BINAP (187 mg, 0.30 mmol) and $Cs_2CO_3$ (733 mg, 2.25 mmol) in toluene (15 mL) was stirred at 120° C. for overnight. After cooling down to room temperature, water was added. The mixture was extracted with EtOAc. The organic layer was dried over $NaSO_4$ and concentrated. The residue was purified by column chromatograpgy (petroleum ether/EtOAc=3/1) to afford the desired product (403 mg, yield 56%) as a yellow solid.

(R)-3-(2-(2,5-Difluorophenyl)pyrrolidin-1-yl)-1-((2-(trimethylsilyl)ethoxy)methyl)-1H-pyrazolo[3,4-b]pyridin-5-amine

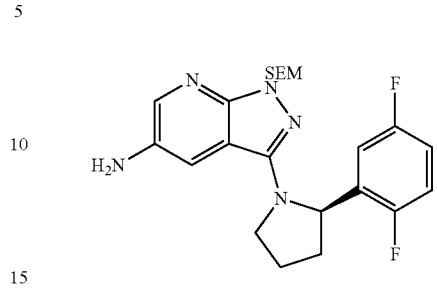

A mixture of (R)-3-(2-(2,5-difluorophenyl)pyrrolidin-1-yl)-5-nitro-1-((2-(trimethylsilyl)ethoxy)methyl)-1H-pyrazolo[3,4-b]pyridine (403 mg, 0.85 mmol), $NH_4Cl$ (400 mg) and Fe (400 mg) in $EtOH/H_2O$ (20 mL/5 mL) was stirred at 80° C. for 3 h. The mixture was filtered. The filtrate was concentrated. The residue was diluted with EtOAc and washed with aq.$NaHCO_3$. The organic layer was dried with $NaSO_4$ and concentrated. The residue was purified by column chromatograpgy (petroleum ether/EtOAc=1/2) to afford the desired product (260 mg, yield 69%) as a yellow solid.

MS-ESI: m/z 446[M+H]+.

$^1$H NMR (400 MHz, $CDCl_3$): δ (ppm) 8.10 (d, 1H, J=2.8 Hz), 7.14-7.07 (m, 2H), 7.03-7.01 (m, 1H), 6.97-6.93 (m, 1H), 5.67-5.63 (m, 1H), 5.45-5.43 (m, 1H), 4.06-4.03 (m, 1H), 3.82-3.78 (m, 1H), 3.66-3.61 (m, 2H), 2.53-2.50 (m, 1H), 2.11-2.04 (m, 3H), 0.99-0.93 (m, 2H), 0.08 (s, 9H).

Synthesis of Intermediate B

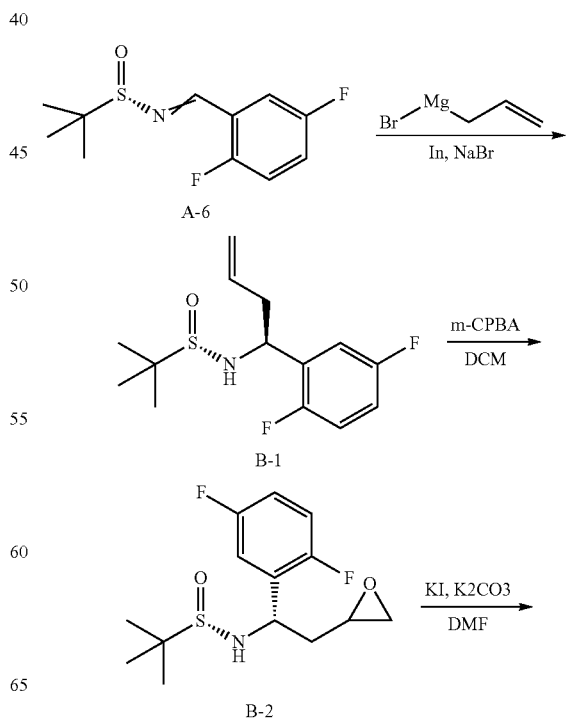

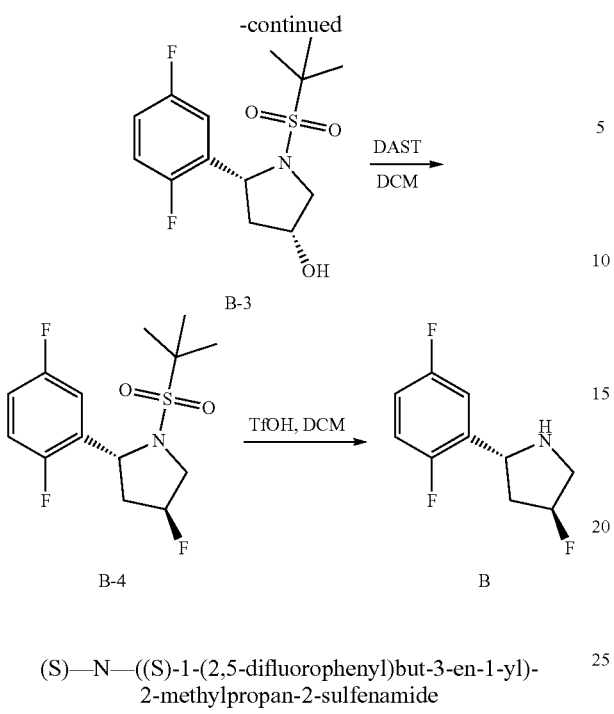

B-3

B-4 → B

TfOH, DCM (S)—N—((S)-1-(2,5-difluorophenyl)but-3-en-1-yl)-2-methylpropan-2-sulfenamide

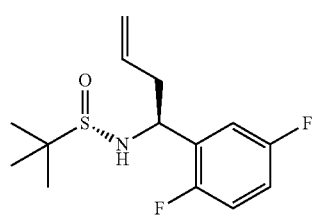 [SMILES: C=CC[C@H](N[S@@](=O)C(C)(C)C)c1cc(F)ccc1F]

(R)—N-(2,5-difluorobenzyliden)-2-methylpropan-2-sulfinamide (30 g, 122.45 mmol) was added to an aqueous solution of saturated sodium bromide (480 mL) at room temperature. Indium (42 g, 367.35 mmol) was added, followed by the addition of allyl magnesium bromide (42 ml, 489.8 mmol). The mixture was stirred at room temperature for 6 h. TLC showed that the reaction was completed, then the reaction was quenched with saturated sodium bicarbonate and filtered. The filtrate was extracted with ethyl acetate, washed with saturated brine, dried over anhydrous sodium sulfate, and concentrated to afford (S)—N—((S)-1-(2,5-difluorophenyl)but-3-en-1-yl)-2-methylpropan-2-sulfenamide as yellow solid (35 g).

(S)—N-((1S)-1-(2,5-difluorophenyl)-2-(oxiran-2-yl)ethyl)-2-methylpropan-2-sulfinylamide

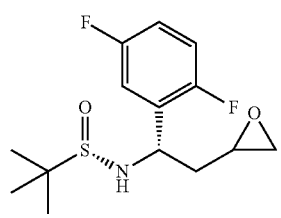 [SMILES: CC(C)(C)[S@](=O)N[C@@H](CC1CO1)c1cc(F)ccc1F]

(S)—N—((S)-1-(2,5-difluorophenyl)but-3-en-1-yl)-2-methylpropan-2-sulfenamide (35 g, 121.95 mmol) was dissolved in dichloromethane (800 mL), and 3-chloroperbenzoic acid (80 g, 365.85 mmol) was added in batches at room temperature and the resulting mixture was stirred at room temperature overnight. TLC showed that the reaction was completed, and the mixture was washed sequentially with saturated sodium bicarbonate, saturated sodium thiosulfate, saturated brine, and dried over anhydrous sodium sulfate, and the filtrate was concentrated to afford (S)—N-((1S)-1-(2,5-difluorophenyl)-2-(oxiran-2-yl)ethyl)-2-methylpropan-2-sulfinylamide as yellow solid (31 g, yield: 79%).

(3R,5R)-1-(tert-butylsulfonyl)-5-(2,5-difluorophenyl)pyrrolidin-3-ol

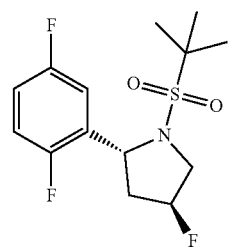 [SMILES: CC(C)(C)S(=O)(=O)N1C[C@@H](F)C[C@@H]1c1cc(F)ccc1F]

A mixture of (S)—N-((1S)-1-(2,5-difluorophenyl)-2-(oxiran-2-yl)ethyl)-2-methylpropan-2-sulfinylamide (31 g, 97.18 mmol), potassium carbonate (40 g, 291.53 mmol) and potassium iodide (16 g, 97.18 mmol) in N,N-dimethylformamide (300 mL) was stirred at 100° C. for 1 h. TLC showed that the reaction was completed. The reaction solution was cooled to room temperature and filtered. The filtrate was poured into water and extracted with ethyl acetate. The combined organic phase was washed with saturated brine, dried with anhydrous sodium sulfate, and the filtrate was concentrated and purified by column chromatography (petroleum ether/ethyl acetate=10/1-5/1) to afford (3R,5R)-1-(tert-butylsulfonyl)-5-(2,5-difluorophenyl)pyrrolidin-3-ol (7.5 g).

2R,4S)-2-(2,5-difluorophenyl)-4-fluoropyrrolidine (3R,5R)-1-(tert-butylsulfonyl)-5-(2,5-difluorophenyl)pyrrolidin-3-ol (2.0 g, 6.27 mmol) was dissolved in dichloromethane (50 mL) and cooled to −60° C., then DAST (2 mL) was added to the mixture. The mixture was spontaneously warmed to room temperature and stirred overnight. LC-MS showed that the reaction was completed. The reaction solution was diluted with dichloromethane, and slowly poured into ice water. The organic phase was separated, washed with saturated brine and dried with anhydrous sodium sulfate, then the filtrate was concentrated and purified by column chromatography (petroleum ether/ethyl acetate=10/1) to afford (2R,4S)-1-(tert-butylsulfonyl)-2-(2,5-difluorophenyl)-4-fluorine as yellow solid (1.2 g, yield: 60%).

(2R,4S)-2-(2,5-difluorophenyl)-4-fluoropyrrolidine

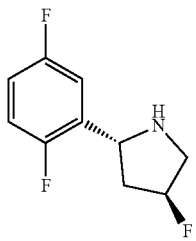 [SMILES: Fc1ccc(F)c([C@H]2C[C@H](F)CN2)c1]

Trifluoromethanesulfonic acid (0.7 mL) was added dropwise to a mixture of (2R,4S)-1-(tert-butylsulfonyl)-2-(2,5-difluorophenyl)-4-fluorine (500 mg, 1.55 mmol) in dichloromethane (20 mL) at room temperature and the mixture was stirred at room temperature for 2 h. The mixture was concentrated, and residue was washed with 2M sodium hydroxide and extracted with ethyl acetate. The organic phase was separated, washed with saturated brine, dried over anhydrous sodium sulfate. The filtrate was concentrated and purified by column chromatography (petroleum ether/ethyl acetate=4/1) to afford (2R,4S)-2-(2,5-difluorophenyl)-4-fluoropyrroline as yellow solid (305 mg, yield: 99%).

Synthesis of Intermediate C

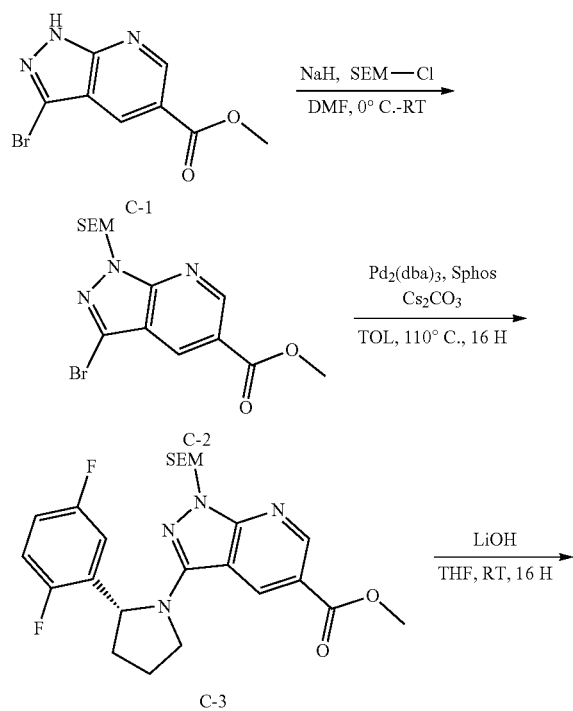

Methyl 3-bromo-1-((2-(trimethylsilyl)ethoxy)methyl)-1H-pyrazolo[3,4-b]pyridine-5-carboxylate

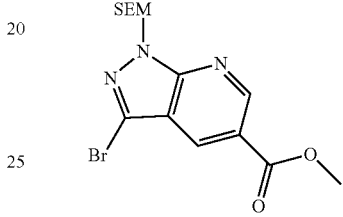

To a mixture of methyl 3-bromo-1H-pyrazolo[3,4-b]pyridine-5-carboxylate (200 mg, 0.78 mmol) in THF (18 mL) was added NaH (47 mg, 1.17 mmol) slowly at 0° C. The mixture was stirred at 0° C. for 0.5 h. SEMCl (130 mg, 1.17 mmol) was added and stirred for 0.5 h. The reaction was quenched with ice-water and extracted with EtOAc. The organic layer was dried over NaSO₄ and concentrated. The residue was purified by column chromatograpgy (petroluenm ether/EtOAc=10/1) to afford the desired product (180 mg, yield 60%) as a yellow solid.

Methyl (R)-3-(2-(2,5-difluorophenyl)pyrrolidin-1-yl)-1-((2-(trimethylsilyl)ethoxy)methyl)-1H-pyrazolo[3,4-b]pyridine-5-carboxylate

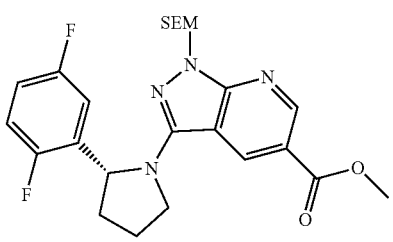 [SMILES: COC(=O)c1cnc2c(c1)c(N1CCC[C@@H]1c1cc(F)ccc1F)nn2COCC[Si](C)(C)C]

A mixture of methyl 3-bromo-1-((2-(trimethylsilyl)ethoxy)methyl)-1H-pyrazolo[3,4-b]pyridine-5-carboxylate (180 mg, 0.46 mmol), (R)-2-(2,5-difluorophenyl)pyrrolidine (85 mg, 0.46 mmol), Pd₂(dba)₃ (42 mg, 0.046 mmol), S-Phos (23 mg, 0.055 mmol) and Cs₂CO₃ (300 mg, 0.92 mmol) in Toluene (15 mL) was stirred at 120° C. for overnight. After cooling down to room temperature, ice-water was added. The mixture was extracted with EtOAc. The organic layer was dried over NaSO₄ and concentrated. The residue was purified by column chromatograpgy (petroluenm ether/EtOAc=10/1) to afford the desired product (50 mg, yield 22%) as a yellow solid.

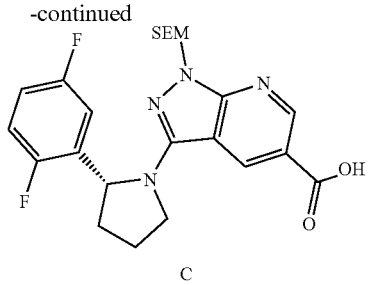

(R)-3-(2-(2,5-Difluorophenyl)pyrrolidin-1-yl)-1-((2-(trimethylsilyl)ethoxy)methyl)-1H-pyrazolo[3,4-b]pyridine-5-carboxylic acid

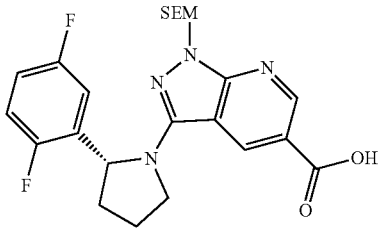 [SMILES: C[Si](C)(C)CCOCn1nc(N2CCC[C@@H]2c2cc(F)ccc2F)c2cc(C(=O)O)cnc21]

To a mixture of methyl (R)-3-(2-(2,5-difluorophenyl)pyrrolidin-1-yl)-1-((2-(trimethylsilyl)ethoxy)methyl)-1H-pyrazolo[3,4-b]pyridine-5-carboxylate (50 mg, 0.10 mmol) in THF (2 mL) was added LiOH monohydrate (16 mg, 0.40 mmol) and H$_2$O (0.5 mL). The mixture was stirred at r.t. for 16 h. TLC shows majority starting martial. The mixture was heated to 80° C. for 2 h. The mixture was concentrated to afford crude product (100 mg, yield 100%) as a yellow solid.

Synthesis of Intermediate D

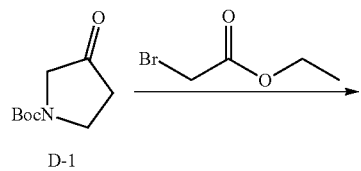

D-1

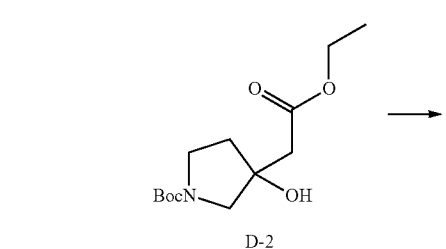

D-2

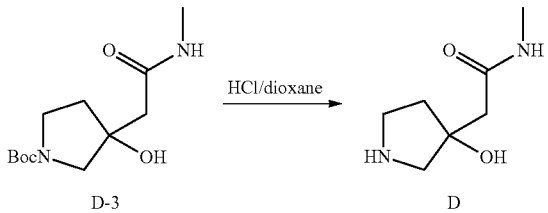

D-3 → D

Tert-butyl 3-(2-ethoxy-2-oxoethyl)-3-hydroxypyrrolidine-1-carboxylate

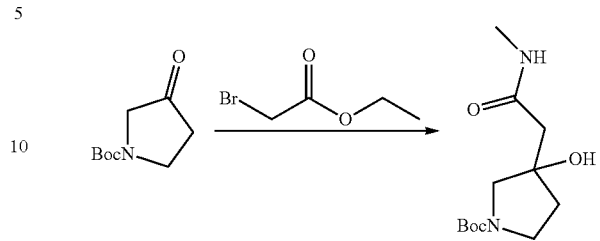

A mixture of Zn (6.4 g, 97.2 mmol) in THF (150 mL) was heated to 80° C. Tert-butyl 3-oxopyrrolidine-1-carboxylate (15.0 g, 81.0 mmol) and ethyl 2-bromoacetate (13.7 g, 82.0 mmol) was added drop wise to the mixture. The mixture was stirred at 80° C. for 1 h. TLC shows the reaction was completed. The mixture was poured to aq. NH$_4$Cl and extracted with EtOAc. The organic layer was washed with aq. NaHCO$_3$ and brine. The mixture was dried and concentrated. The residue was purified by column chromatograpgy (petroleum ether/EtOAc=10/1) to afford the desired product (10.2 g, yield 46%) as yellow oil.

Tert-butyl 3-hydroxy-3-(2-(methylamino)-2-oxoethyl)pyrrolidine-1-carboxylate

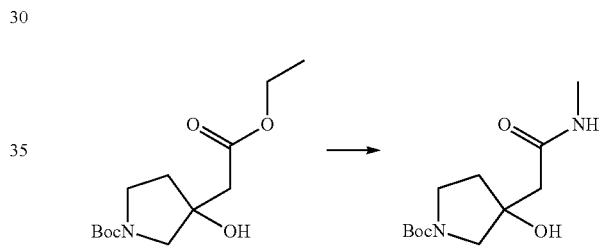

A mixture of tert-butyl 3-(2-ethoxy-2-oxoethyl)-3-hydroxypyrrolidine-1-carboxylate (500 mg, 2.10 mmol) in NH$_3$/MeOH solution (7 mL, 30%) was stirred at 100° C. in a sealed bottle for 2 h. TLC showed the reaction was completed. The mixture was concentrated to afford the desired product (400 mg, yield 84%) as oil.

2-(3-Hydroxypyrrolidin-3-yl)-N-methylacetamide

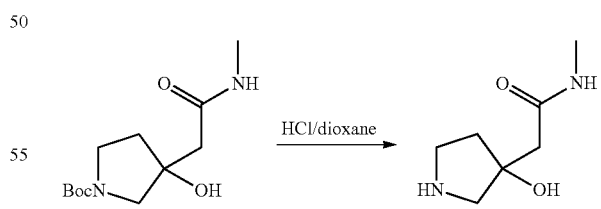

A mixture of tert-butyl 3-hydroxy-3-(2-(methylamino)-2-oxoethyl)pyrrolidine-1-carboxylate (400 mg, 1.60 mmol) in DCM (4 mL) and HCl in dioxane (6 mL, 6.0 M) was stirred at r.t. for overnight. LC-MS showed the reaction was completed. The mixture was concentrated to afford the desired product (240 mg, yield 97%) as oil.

$^1$H NMR (400 MHz, DMSO-d$_6$): δ 9.50 (s, 1H), 9.08 (s, 1H), 8.02-7.92 (m, 1H), 3.25-3.12 (m, 4H), 2.65-2.49 (m, 3H), 1.97-1.83 (m, 2H), 1.79 (s, 2H).

Example 1: N-(3-((R)-2-(2,5-difluorophenyl)pyrrolidin-1-yl)-1H-pyrazolo[3,4-b]pyridin-5-yl)-3-hydroxy-3-(2-(methylamino)-2-oxoethyl)pyrrolidine-1-carboxamide

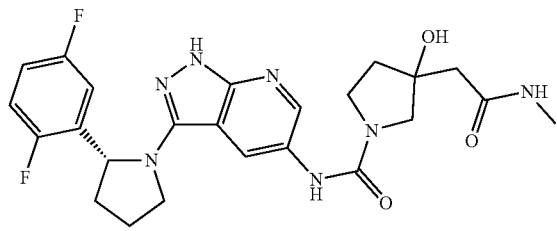 [SMILES: CNC(=O)CC1(O)CCN(C(=O)Nc2cnc3[nH]nc(N4CCC[C@@H]4c4cc(F)ccc4F)c3c2)C1]

To the mixture of (R)-3-(2-(2,5-difluorophenyl)pyrrolidin-1-yl)-1-((2-(trimethylsilyl)ethoxy)methyl)-1H-pyrazolo[3,4-b]pyridin-5-amine (10 mg, 0.023 mmol), Triphosgene (10 mg, 0.033 mmol) in DCM (2 mL) was added DIEA (30 mg, 0.23 mmol) and then stirred at 0° C. for 0.5 h. Then 2-(3-hydroxypyrrolidin-3-yl)-N-methylacetamide (36 mg, 0.23 mmol) was added followed by DIEA (6.0 mg, 0.69 mmol) and stirred at r.t. for 2 h. The mixture was concentrated and re-dissolved in 4 N HCl in dioxane (4 mL). The mixture was stirred at r.t. for 2 h. It was concentrated and purified by reverse phase column chromatography to give the desired product (5.5 mg, yield 47.9%) as yellow solid.

MS (ESI): m/z=500 [M+H]+.

1H NMR (400 MHz, CD3OD) δ 8.32 (d, J=1.6 Hz, 1H), 8.04 (dd, J=5.4, 2.3 Hz, 1H), 7.13-7.06 (m, 1H), 6.96-6.88 (m, 2H), 5.35 (d, J=7.3 Hz, 1H), 4.58 (s, 2H), 4.13-4.08 (m, 1H), 3.72 (m, 1H), 3.63-3.53 (m, 2H), 3.48-3.46 (m, 1H), 2.71 (s, 3H), 2.55 (s, 2H), 2.52-2.42 (m, 1H), 2.08-1.92 (m, 4H).

Example 2: (S)—N-(3-((R)-2-(2,5-difluorophenyl)pyrrolidin-1-yl)-1H-pyrazolo[3,4-b]pyridin-5-yl)-3-hydroxypyrrolidine-1-carboxamide

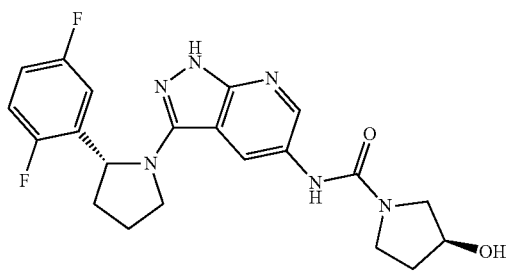 [SMILES: O=C(Nc1cnc2[nH]nc(N3CCC[C@@H]3c3cc(F)ccc3F)c2c1)N1CC[C@H](O)C1]

(S)—N-(3-((R)-2-(2,5-Difluorophenyl)pyrrolidin-1-yl)-1H-pyrazolo[3,4-b]pyridin-5-yl)-3-hydroxypyrrolidine-1-carboxamide (3 mg, yield 15%) was prepared using a method similar to that in example 1 by replacing the corresponding starting material.

MS-ESI: m/z=429 [M+H]+.

1H NMR (400 MHz, DMSO-d6) δ 7.16 (s, 1H), 6.01 (s, 1H), 5.88-5.68 (m, 3H), 4.14-4.12 (m, 1H), 3.22-3.20 (m, 2H), 2.95-2.80 (m, 1H), 5.55-2.48 (m, 1H), 2.52-2.31 (m, 3H), 1.60-1.40 (m, 3H), 1.38-1.20 (m, 2H), 0.88-0.75 (m, 9H).

Example 3

N-(3-((R)-2-(2,5-difluorophenyl)pyrrolidin-1-yl)-1H-pyrazolo[3,4-b]pyridin-5-yl)-6-((S)-3-hydroxypyrrolidin-1-yl)nicotinamide

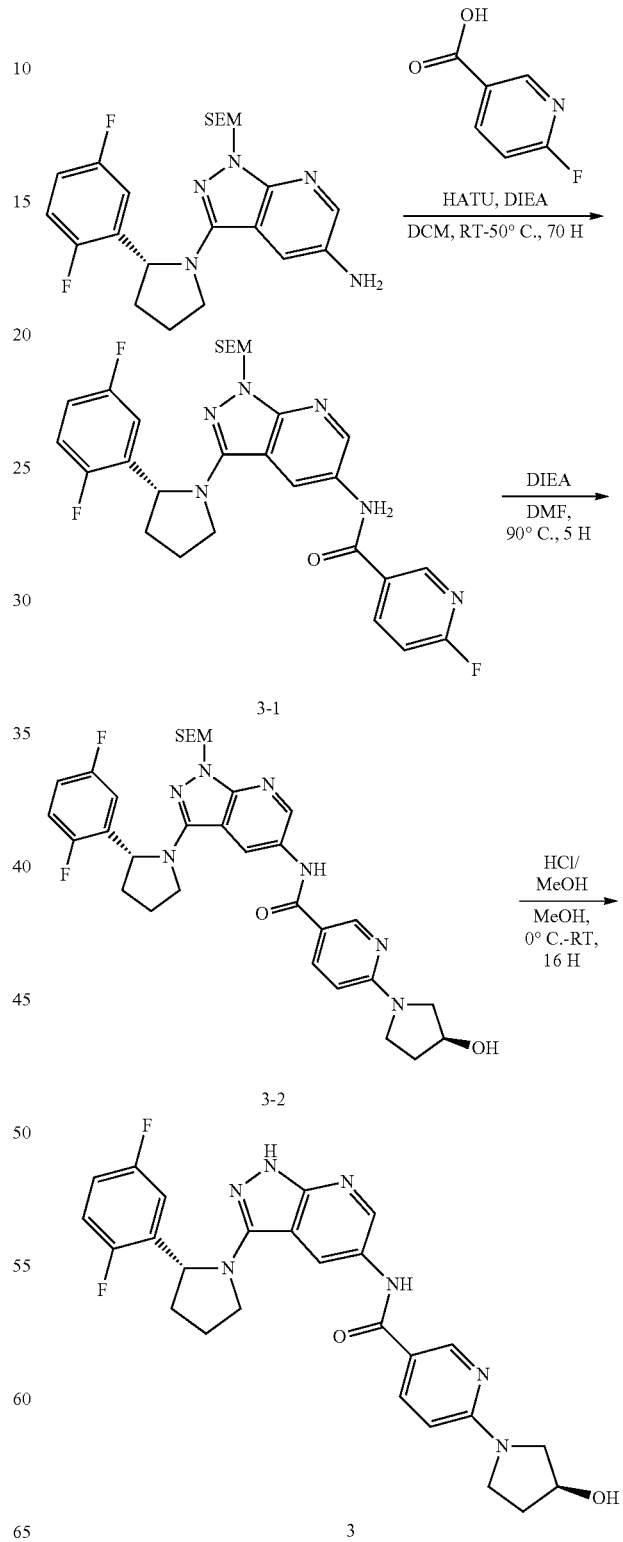

(R)—N-(3-(2-(2,5-difluorophenyl)pyrrolidin-1-yl)-1-((2-(trimethylsilyl)ethoxy)methyl)-1H-pyrazolo[3,4-b]pyridin-5-yl)-6-fluoronicotinamide

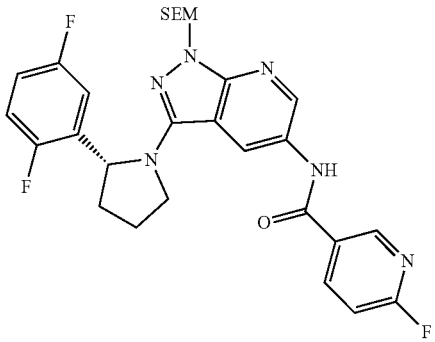 [SMILES: C[Si](C)(C)CCOCn1nc(N2CCC[C@@H]2c2cc(F)ccc2F)c2cc(NC(=O)c3ccc(F)nc3)cnc21]

To a solution of (R)-3-(2-(2,5-difluorophenyl)pyrrolidin-1-yl)-1-((2-(trimethylsilyl)ethoxy)methyl)-1H-pyrazolo[3,4-b]pyridin-5-amine (60 mg, 0.13 mmol) and HATU (274 mg, 0.72 mmol) in anhydrous DMF (2 mL) was added 6-fluoronicotinic acid (92 mg, 0.65 mmol) and DIEA (134 mg, 1.04 mmol). The reaction solution was stirred at room temperature for 16 h. LC-MS showed most starting materials were remaining, the mixture was stirred at 50° C. for another 72 h. Then the mixture was purified by Prep-HPLC to obtain the desired product (R)—N-(3-(2-(2,5-difluorophenyl)pyrrolidin-1-yl)-1-((2-(trimethylsilyl)ethoxy)methyl)-1H-pyrazolo[3,4-b]pyridin-5-yl)-6-fluoronicotinamide (25 mg, 34%), as yellow solid.

MS (ESI): m/z=439 [M+H−130]$^+$.

N-(3-((R)-2-(2,5-difluorophenyl)pyrrolidin-1-yl)-1-((2-(trimethylsilyl)ethoxy)methyl)-1H-pyrazolo[3,4-b]pyridin-5-yl)-6-((S)-3-hydroxypyrrolidin-1-yl)nicotinamide

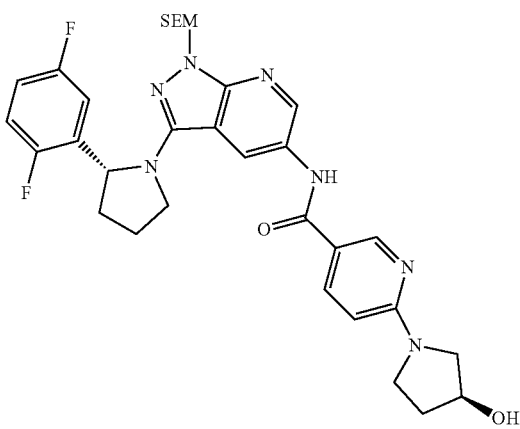 [SMILES: C[Si](C)(C)CCOCn1nc(N2CCC[C@@H]2c2cc(F)ccc2F)c2cc(NC(=O)c3ccc(N4CC[C@H](O)C4)nc3)cnc21]

To a solution of (R)—N-(3-(2-(2,5-difluorophenyl)pyrrolidin-1-yl)-1-((2-(trimethylsilyl)ethoxy)methyl)-1H-pyrazolo[3,4-b]pyridin-5-yl)-6-fluoronicotinamide (25 mg, 0.04 mmol) and (S)-pyrrolidin-3-ol (274 mg, 0.72 mmol) in anhydrous DMF (1 mL) was added DIEA (41 mg, 0.32 mmol). The reaction solution was stirred at 90° C. for 3 h and the mixture was purified by Prep-HPLC to obtain the desired product N-(3-((R)-2-(2,5-difluorophenyl)pyrrolidin-1-yl)-1-((2-(trimethylsilyl)ethoxy)methyl)-1H-pyrazolo[3,4-b]pyridin-5-yl)-6-((S)-3-hydroxypyrrolidin-1-yl)nicotinamide (16 mg, 57%), as yellow solid.

MS (ESI): m/z=506 [M+H−130]$^+$.

N-(3-((R)-2-(2,5-difluorophenyl)pyrrolidin-1-yl)-1H-pyrazolo[3,4-b]pyridin-5-yl)-6-((S)-3-hydroxypyrrolidin-1-yl)nicotinamide

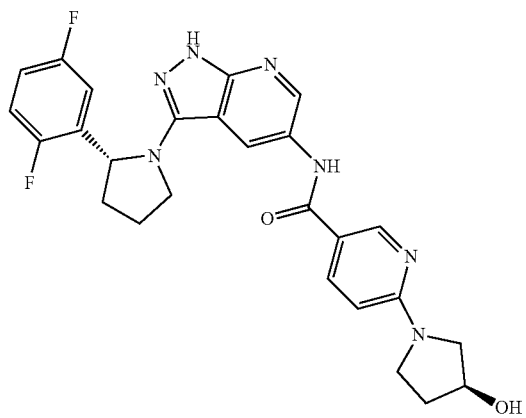 [SMILES: O=C(Nc1cnc2[nH]nc(N3CCC[C@@H]3c3cc(F)ccc3F)c2c1)c1ccc(N2CC[C@H](O)C2)nc1]

To a solution of N-(3-((R)-2-(2,5-difluorophenyl)pyrrolidin-1-yl)-1-((2-(trimethylsilyl)ethoxy)methyl)-1H-pyrazolo[3,4-b]pyridin-5-yl)-6-((S)-3-hydroxypyrrolidin-1-yl)nicotinamide (16 mg, 0.03 mmol) in methonal (1 mL) was added HCl in dioxane (2 mL, 4M) under ice bath. The reaction solution was warmed to room temperature and stirred for 16 h. The reaction solution was concentrated, and the residue was purified by Prep-HPLC to obtain the desired product N-(3-((R)-2-(2,5-difluorophenyl)pyrrolidin-1-yl)-1-((2-(trimethylsilyl)ethoxy)methyl)-1H-pyrazolo[3,4-b]pyridin-5-yl)-6-((S)-3-hydroxypyrrolidin-1-yl)nicotinamide (8.4 mg, 66%), as yellow solid. MS (ESI): m/z=506 [M+H]$^+$.

$^1$H NMR (400 MHz, DMSO-d6) δ 12.14 (s, 1H), 10.04 (s, 1H), 8.71 (d, J=2.5 Hz, 1H), 8.55 (d, J=2.2 Hz, 1H), 8.50 (d, J=2.3 Hz, 1H), 8.03 (dd, J=8.9, 2.5 Hz, 1H), 7.24-7.17 (m, 1H), 7.07-6.97 (m, 2H), 6.50 (d, J=9.0 Hz, 1H), 5.18 (dd, J=8.4, 3.8 Hz, 1H), 5.00 (s, 1H), 4.38 (s, 1H), 4.16-4.09 (m, 1H), 3.63 (m, 1H), 3.55-3.45 (m, 3H), 2.42-2.34 (m, 1H), 2.06-1.76 (m, 6H).

Example 4

(R)-3-(2-(2,5-difluorophenyl)pyrrolidin-1-yl)-1H-pyrazolo[3,4-b]pyridine-5-carboxamide

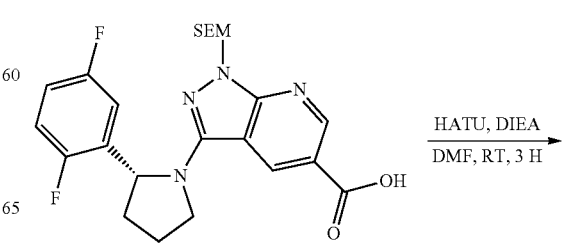

-continued

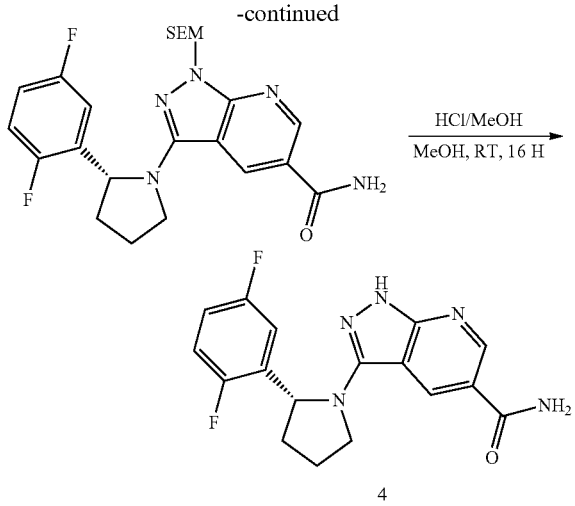

(R)-3-(2-(2,5-difluorophenyl)pyrrolidin-1-yl)-1-((2-(trimethylsilyl)ethoxy)methyl)-1H-pyrazolo[3,4-b]pyridine-5-carboxamide

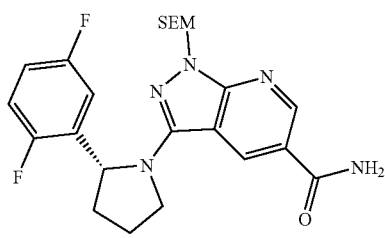 [SMILES: C[Si](C)(C)CCOCn1nc(N2CCC[C@@H]2c2cc(F)ccc2F)c2cc(C(N)=O)cnc21]

To a solution of (R)-3-(2-(2,5-difluorophenyl)pyrrolidin-1-yl)-1-((2-(trimethylsilyl)ethoxy)methyl)-1H-pyrazolo[3,4-b]pyridine-5-carboxylic acid (50 mg crude, 0.06 mmol) and HATU (57 mg, 0.15 mmol) in anhydrous DMF (1 mL) was added DIEA (39 mg, 0.30 mmol) and ammonium chloride (9 mg, 0.18 mmol). The reaction solution was stirred at room temperature for 16 h. The mixture was purified by Prep-HPLC to obtain the desired product (R)-3-(2-(2,5-difluorophenyl)pyrrolidin-1-yl)-1-((2-(trimethylsilyl)ethoxy)methyl)-1H-pyrazolo[3,4-b]pyridine-5-carboxamide (30 mg), as yellow solid.

MS (ESI): m/z=474 [M+H]$^+$.

(R)-3-(2-(2,5-difluorophenyl)pyrrolidin-1-yl)-1H-pyrazolo[3,4-b]pyridine-5-carboxamide

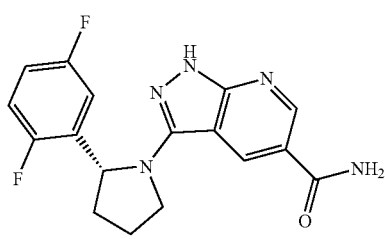 [SMILES: NC(=O)c1cnc2[nH]nc(N3CCC[C@@H]3c3cc(F)ccc3F)c2c1]

To a solution of (R)-3-(2-(2,5-difluorophenyl)pyrrolidin-1-yl)-1-((2-(trimethylsilyl)ethoxy)methyl)-1H-pyrazolo[3, 4-b]pyridine-5-carboxamide (30 mg, 0.06 mmol) in methonal (1 mL) was added HCl in dioxane (2 mL, 4M) under ice bath. The reaction solution was stirred at room temperature for 16 h and concentrated. The residue was purified by Prep-HPLC to obtain the desired product (R)-3-(2-(2,5-difluorophenyl)pyrrolidin-1-yl)-1H-pyrazolo[3,4-b]pyridine-5-carboxamide (8.4 mg, yield 42%).

MS (ESI): m/z=344 [M+H]$^+$.

$^1$H NMR (400 MHz, DMSO-d$_6$) δ 12.47 (s, 1H), 8.85-8.79 (m, 1H), 8.64-8.58 (m, 1H), 8.06 (s, 1H), 7.32 (s, 1H), 7.24-7.17 (m, 1H), 7.08-6.93 (m, 2H), 5.23-5.17 (m, 1H), 4.24-4.16 (m, 1H), 3.67 (m, 1H), 2.43-2.34 (m, 1H), 2.08-1.94 (m, 2H), 1.85-1.76 (m, 1H).

Example 5

3-((2R,4S)-2-(2,5-difluorophenyl)-4-fluoropyrrolidin-1-yl)-1H-pyrazolo[3,4-b]pyridine-5-carboxamide

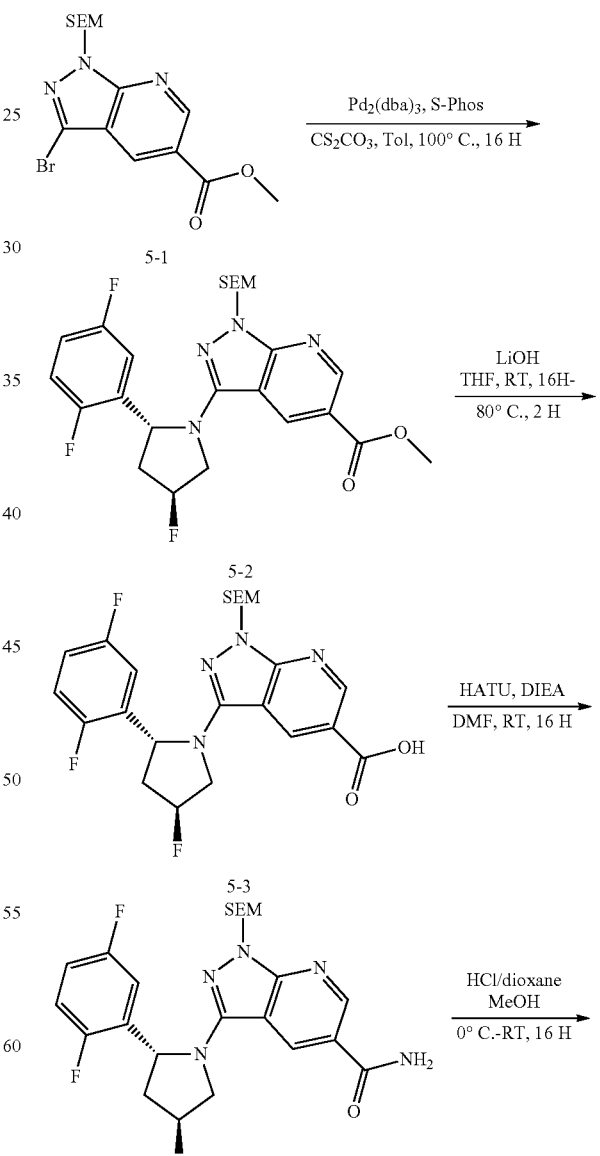

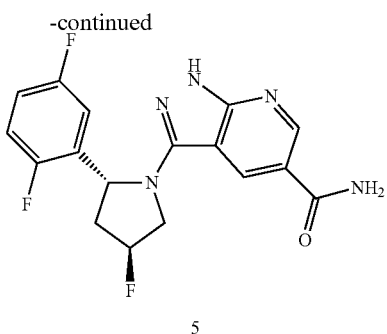

Methyl 3-((2R,4S)-2-(2,5-difluorophenyl)-4-fluoro-pyrrolidin-1-yl)-1-((2-(trimethylsilyl)ethoxy)methyl)-1H-pyrazolo[3,4-b]pyridine-5-carboxylate

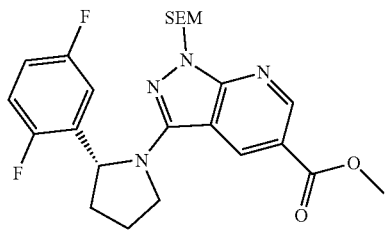 [SMILES: COC(=O)c1cnc2c(c1)c(N1CCC[C@@H]1c1cc(F)ccc1F)nn2COCC[Si](C)(C)C]

To a solution of methyl 3-bromo-1-((2-(trimethylsilyl)ethoxy)methyl)-1H-pyrazolo[3,4-b]pyridine-5-carboxylate (139 mg, 0.36 mmol), (2R,4S)-2-(2,5-difluorophenyl)-4-fluoropyrrolidine (60 mg, 0.30 mmol), Cesium carbonate (196 mg, 0.60 mmol) in anhydrous DMF (2 mL) was added Tris(dibenzylideneacetone)dipalladium (27 mg, 0.03 mmol) and 2-Dicyclohexylphosphino-2',6'-dimethoxy-1,1'-biphenyl (16 mg, 0.04 mmol). The reaction solution was stirred at 100° C. for 16 h and concentrated. The residue was purified by combiflash column chromatography (petroleum ether:ethyl acetate=8:1) to obtain the desired product 3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine-5-carboxylate (100 mg crude, 66%), as yellow solid.

MS (ESI): m/z=506.9 [M+H]$^+$.

3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine-5-carboxylic acid

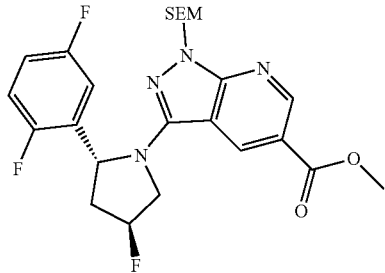 [SMILES: COC(=O)c1cnc2c(c1)c(N1C[C@@H](F)C[C@@H]1c1cc(F)ccc1F)nn2COCC[Si](C)(C)C]

To a solution of methyl 3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine-5-carboxylate (100 mg crude, 0.20 mmol) in tetrahydrofuran (2 mL) was added LiOH (16 mg, 0.40 mmol) and water (0.5 mL). The reaction solution was stirred at room temperature for 16 h, TLC showed most starting material remaining, then the reaction mixture was heated to 80° C. for 2 h, After that the mixture was cooled to room temperature an concentrated to obtain the desired product 3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine-5-carboxylic acid (100 mg crude, 100%), as yellow solid.

MS (ESI): m/z=374.9 [M−117]$^+$.

3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine-5-carboxamide

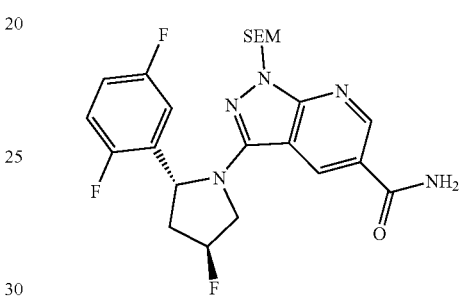

To a solution of 3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine-5-carboxylic acid (40 mg crude, 0.06 mmol) and HATU (57 mg, 0.15 mmol) in anhydrous DMF (1 mL) was added DIEA (39 mg, 0.30 mmol) and ammonium chloride (9 mg, 0.18 mmol). The reaction solution was stirred at room temperature for 16 h. The mixture was purified by Prep-HPLC to obtain the desired product 3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine-5-carboxamide (15 mg, 52%), as yellow solid.

MS (ESI): m/z=491.9 [M+H]$^+$.

3-((2R,4S)-2-(2,5-difluorophenyl)-4-fluoropyrrolidin-1-yl)-1H-pyrazolo[3,4-b]pyridine-5-carboxamide

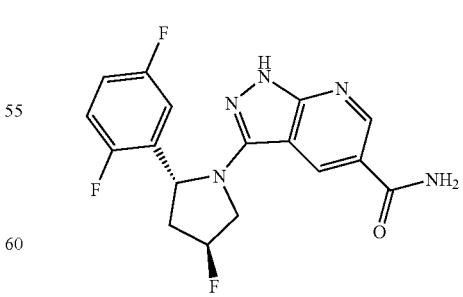

To a solution of 3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine-5-carboxamide (15 mg, 0.03 mmol) in methonal (1 mL) was added HCl in dioxane (2 mL, 4M) under ice bath. The reaction solution was stirred at room temperature for 16 h and concentrated. The residue was purified by Prep-HPLC to obtain the desired product 3-((2R,4S)-2-(2,5-difluorophenyl)-4-fluoropyrrolidin-1-yl)-1H-pyrazolo[3,4-b]pyridine-5-carboxamide (3 mg, 27%), as yellow solid.

MS (ESI): m/z=362 [M+H]$^+$.

$^1$H NMR (400 MHz, DMSO-d$_6$) δ 12.56 (s, 1H), 8.84 (d, J=2.0 Hz, 1H), 8.64 (d, J=2.0 Hz, 1H), 8.08 (s, 1H), 7.37 (s, 1H), 7.24-7.09 (m, 2H), 7.09-7.00 (m, 1H), 5.58-5.45 (m, 1H), 5.32-5.26 (m, 1H), 4.48-4.38 (m, 1H), 4.07-3.95 (m, 1H), 2.77-2.65 (m, 1H), 2.18-2.01 (m, 1H).

Example 6: (R)-3-(2-(2,5-difluorophenyl)pyrrolidin-1-yl)-N-(2-hydroxyethyl)-1H-pyrazolo[3,4-b]pyridine-5-carboxamide

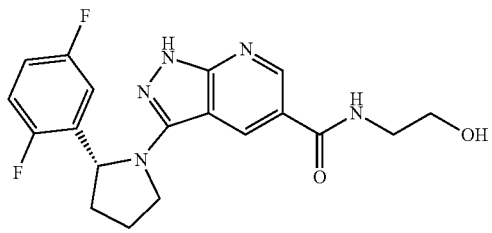 [SMILES: O=C(NCCO)c1cnc2[nH]nc(N3CCC[C@@H]3c3cc(F)ccc3F)c2c1]

(R)-3-(2-(2,5-Difluorophenyl)pyrrolidin-1-yl)-N-(2-hydroxyethyl)-1H-pyrazolo[3,4-b]pyridine-5-carboxamide was prepared using a method similar to that in example 4 by replacing the corresponding starting material.

MS (ESI): m/z=388 [M+H]$^+$.

$^1$H NMR (400 MHz, DMSO-d$_6$) δ 9.61 (s, 1H), 8.61 (s, 1H), 7.90 (d, J=8.0 Hz, 1H), 7.76 (d, J=9.8 Hz, 1H), 7.44 (s, 1H), 7.08-6.98 (m, 2H), 6.92-6.86 (m, 1H), 6.69 (d, J=8.8 Hz, 2H), 5.24 (d, J=6.5 Hz, 1H), 3.95-3.85 (m, 1H), 3.55 (m, 1H), 3.27 (s, 1H), 3.11 (m, 5H), 2.42-2.29 (m, 1H), 2.03-1.90 (m, 2H), 1.85-1.76 (m, 1H).

Example 7

(R)-3-(2-(2,5-difluorophenyl)pyrrolidin-1-yl)-N-methyl-1H-pyrazolo[3,4-b]pyridine-5-carboxamide

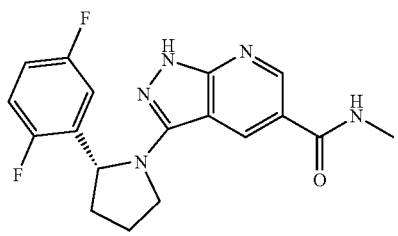 [SMILES: CNC(=O)c1cnc2[nH]nc(N3CCC[C@@H]3c3cc(F)ccc3F)c2c1]

(R)-3-(2-(2,5-Difluorophenyl)pyrrolidin-1-yl)-N-methyl-1H-pyrazolo[3,4-b]pyridine-5-carboxamide was prepared using a method similar to that in example 4 by replacing the corresponding starting material.

MS (ESI): m/z=358 [M+Na]$^+$

1H NMR (400 MHz, DMSO-d6) δ 12.47 (s, 1H), 8.80 (d, J=2.0 Hz, 1H), 8.56 (d, J=2.0 Hz, 1H), 8.53-8.47 (m, 1H), 7.25-7.19 (m, 1H), 7.08-6.95 (m, 2H), 5.21 (dd, J=8.2, 3.3 Hz, 1H), 4.22-4.75 (m, 1H), 3.68 (m, 1H), 2.78 (d, J=4.5 Hz, 3H), 2.44-2.34 (m, 1H), 2.10-1.93 (m, 2H), 1.85-1.77 (m, 1H).

Example 8: (R)-3-(2-(2,5-difluorophenyl)pyrrolidin-1-yl)-N-(2-methoxyethyl)-1H-pyrazolo[3,4-b]pyridine-5-carboxamide

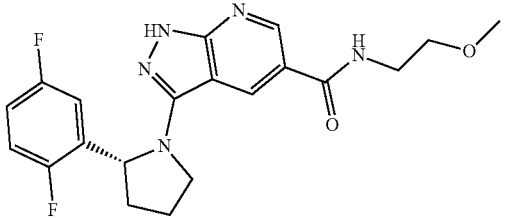 [SMILES: COCCNC(=O)c1cnc2[nH]nc(N3CCC[C@@H]3c3cc(F)ccc3F)c2c1]

(R)-3-(2-(2,5-difluorophenyl)pyrrolidin-1-yl)-N-(2-methoxyethyl)-1H-pyrazolo[3,4-b]pyridine-5-carboxamide was prepared using a method similar to that in example 4 by replacing the corresponding starting material.

MS (ESI): m/z=402 [M+H]$^+$.

$^1$H NMR (400 MHz, CD$_3$OD) S 8.79 (d, J=2.0 Hz, 1H), 8.53 (d, J=2.0 Hz, 1H), 7.14-7.08 (m, 1H), 6.95-6.89 (m, 2H), 5.39 (d, J=6.5 Hz, 1H), 4.21-4.14 (m, 1H), 3.78 (dd, J=16.1, 8.6 Hz, 1H), 3.58-3.53 (m, 4H), 3.37 (s, 3H), 2.51-2.45 (m, 1H), 2.14-2.03 (m, 2H), 2.00-1.93 (m, 1H).

Example 9: (R)-3-(2-(2,5-difluorophenyl)pyrrolidin-1-yl)-N-(3-hydroxypropyl)-1H-pyrazolo[3,4-b]pyridine-5-carboxamide

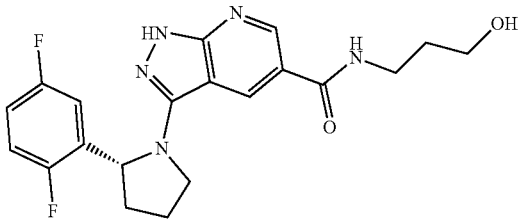 [SMILES: O=C(NCCCO)c1cnc2[nH]nc(N3CCC[C@@H]3c3cc(F)ccc3F)c2c1]

(R)-3-(2-(2,5-difluorophenyl)pyrrolidin-1-yl)-N-(3-hydroxypropyl)-1H-pyrazolo[3,4-b]pyridine-5-carboxamide was prepared using a method similar to that in example 4 by replacing the corresponding starting material.

MS (ESI): m/z=402 [M+H]$^+$.

$^1$H NMR (400 MHz, CD$_3$OD) δ 8.77 (d, J=2.0 Hz, 1H), 8.51 (d, J=2.0 Hz, 1H), 7.11 (td, J=9.3, 4.3 Hz, 1H), 6.97-6.85 (m, 2H), 5.39 (d, J=6.8 Hz, 1H), 4.21-4.13 (m, 1H), 3.78 (dd, J=16.0, 8.6 Hz, 1H), 3.64 (t, J=6.3 Hz, 2H), 3.53-3.41 (m, 2H), 2.55-2.44 (m, 1H), 2.17-2.02 (m, 2H), 2.02-1.94 (m, 1H), 1.86-1.79 (m, 2H).

Example 10: (R)-3-(2-(2,5-difluorophenyl)pyrrolidin-1-yl)-N-(2-hydroxy-2-methylpropyl)-1H-pyrazolo[3,4-b]pyridine-5-carboxamide

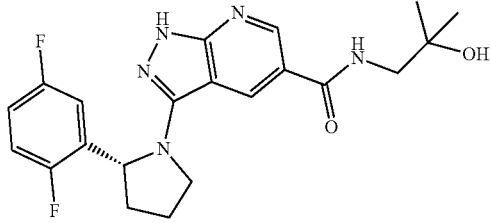 [SMILES: CC(C)(O)CNC(=O)c1cnc2[nH]nc(N3CCC[C@@H]3c3cc(F)ccc3F)c2c1]

(R)-3-(2-(2,5-difluorophenyl)pyrrolidin-1-yl)-N-(2-hydroxy-2-methylpropyl)-1H-pyrazolo[3,4-b]pyridine-5-carboxamide was prepared using a method similar to that in example 4 by replacing the corresponding starting material.

MS (ESI): m/z=416 [M+H]⁺.

¹H NMR (400 MHz, CD₃OD) δ 8.81 (d, J=2.0 Hz, 1H), 8.51 (d, J=2.0 Hz, 1H), 7.11 (td, J=9.2, 4.3 Hz, 1H), 6.97-6.86 (m, 2H), 5.40 (d, J=6.6 Hz, 1H), 4.20-4.12 (m, 1H), 3.78 (dd, J=15.9, 8.7 Hz, 1H), 3.39 (dd, J=30.2, 13.5 Hz, 2H), 2.55-2.43 (m, 1H), 2.14-2.02 (m, 2H), 2.00-1.94 (m, 1H), 1.22 (d, J=2.4 Hz, 6H).

Example 11

N-(3-((2R,4S)-2-(2,5-difluorophenyl)-4-fluoropyrrolidin-1-yl)-1H-pyrazolo[3,4-b]pyridin-5-yl)-6-((S)-3-hydroxypyrrolidin-1-yl)nicotinamide

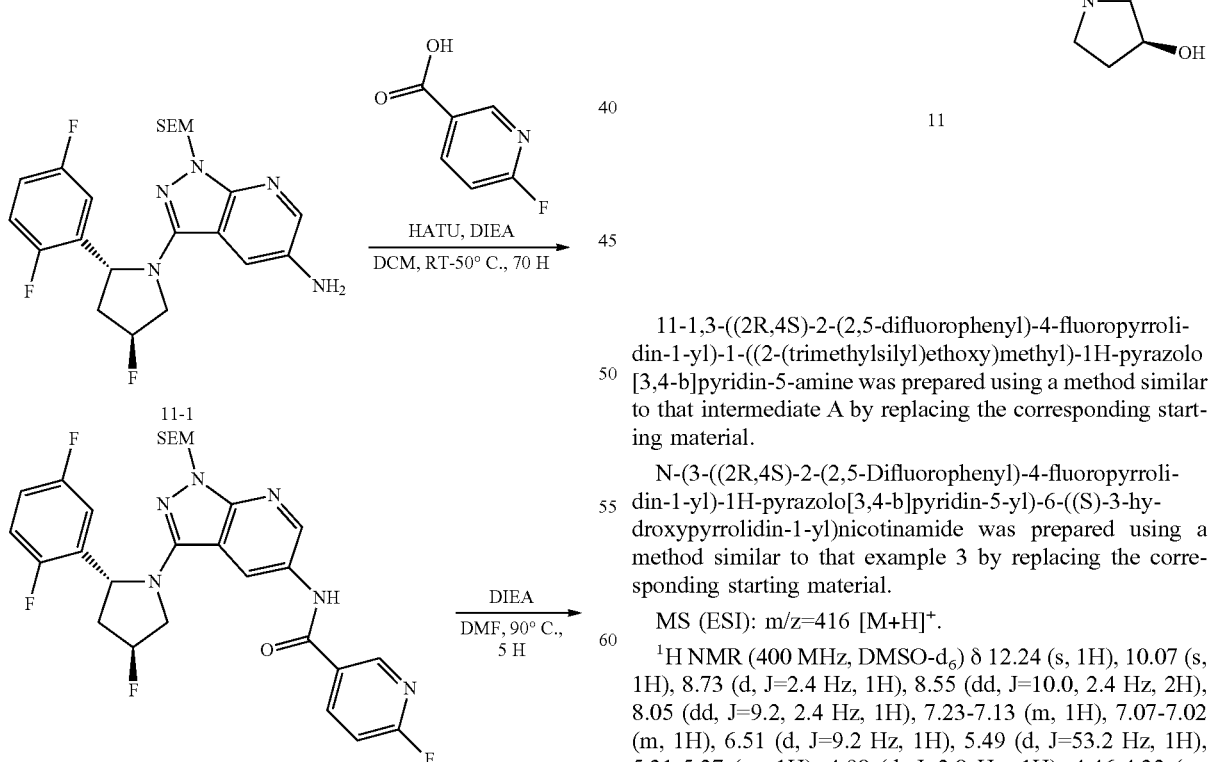

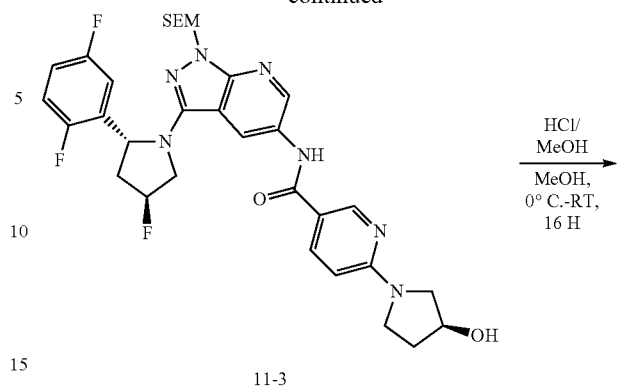

11-1,3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridin-5-amine was prepared using a method similar to that intermediate A by replacing the corresponding starting material.

N-(3-((2R,4S)-2-(2,5-Difluorophenyl)-4-fluoropyrrolidin-1-yl)-1H-pyrazolo[3,4-b]pyridin-5-yl)-6-((S)-3-hydroxypyrrolidin-1-yl)nicotinamide was prepared using a method similar to that example 3 by replacing the corresponding starting material.

MS (ESI): m/z=416 [M+H]⁺.

¹H NMR (400 MHz, DMSO-d₆) δ 12.24 (s, 1H), 10.07 (s, 1H), 8.73 (d, J=2.4 Hz, 1H), 8.55 (dd, J=10.0, 2.4 Hz, 2H), 8.05 (dd, J=9.2, 2.4 Hz, 1H), 7.23-7.13 (m, 1H), 7.07-7.02 (m, 1H), 6.51 (d, J=9.2 Hz, 1H), 5.49 (d, J=53.2 Hz, 1H), 5.31-5.27 (m, 1H), 4.98 (d, J=2.8 Hz, 1H), 4.46-4.32 (m, 2H), 3.95-3.86 (m, 1H), 3.54-3.47 (m, 2H), 2.69-2.63 (m, 1H), 2.15-1.86 (m, 4H).

Example 12: (R)-3-(2-(2,5-difluorophenyl)pyrrolidin-1-yl)-N-(4-hydroxybutyl)-1H-pyrazolo[3,4-b]pyridine-5-carboxamide

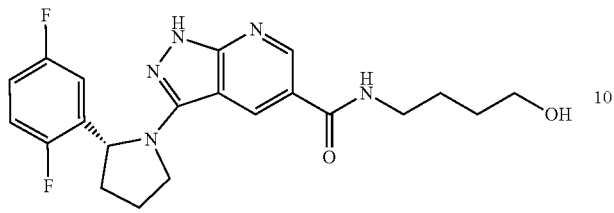

(R)-3-(2-(2,5-difluorophenyl)pyrrolidin-1-yl)-N-(4-hydroxybutyl)-1H-pyrazolo[3,4-b]pyridine-5-carboxamide was prepared using a method similar to that example 4 by replacing the corresponding starting material.

MS (ESI): m/z=416 [M+H]$^+$.

$^1$H NMR (400 MHz, CD$_3$OD) δ 8.78 (d, J=2.0 Hz, 1H), 8.50 (d, J=2.0 Hz, 1H), 7.11 (td, J=9.3, 4.3 Hz, 1H), 6.97-6.87 (m, 2H), 5.39 (d, J=6.0 Hz, 1H), 4.19-4.11 (m, 1H), 3.77 (dd, J=15.9, 8.7 Hz, 1H), 3.60 (t, J=6.3 Hz, 2H), 3.46-3.34 (m, 2H), 2.57-2.44 (m, 1H), 2.12-2.00 (m, 2H), 2.00-1.93 (m, 1H), 1.71-1.58 (m, 4H).

Example 13: Methyl 3-((2R,4S)-2-(2,5-difluorophenyl)-4-fluoropyrrolidin-1-yl)-1H-pyrazolo[3,4-b]pyridine-5-carboxylate

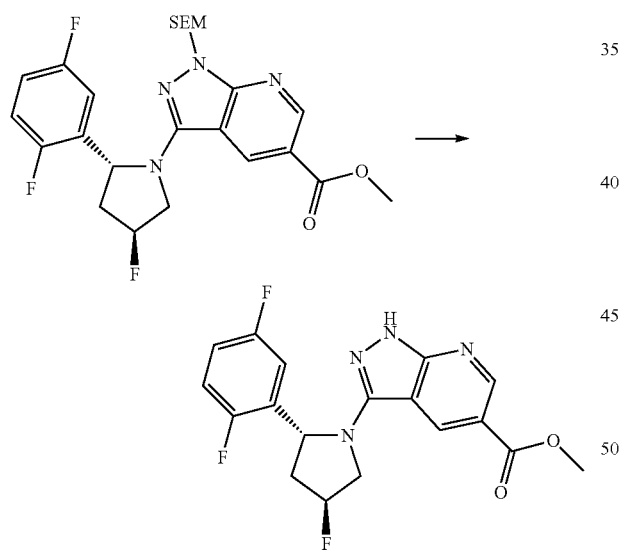

The mixture of methyl 3-((2R,4S)-2-(2,5-difluorophenyl)-4-fluoropyrrolidin-1-yl)-1-((2-(trimethylsilyl) ethoxy)methyl)-1H-pyrazolo[3,4-b]pyridine-5-carboxylate (50 mg, 0.03 mmol) in methanol (1 mL) and 4N HCl in dioxane (2 mL) was stirred at r.t. for 16 h. The mixture was concentrated and purified by reverse phase column chromatography to give methyl 3-((2R,4S)-2-(2,5-difluorophenyl)-4-fluoropyrrolidin-1-yl)-1H-pyrazolo[3,4-b]pyridine-5-carboxylate (22 mg, yield 2.6%) as yellow solid.

MS (ESI): m/z=377 [M+H]$^+$.

$^1$H NMR (400 MHz, CD$_3$OD) δ 8.92 (d, J=1.8 Hz, 1H), 8.61 (d, J=1.8 Hz, 1H), 7.14-7.08 (m, 1H), 7.06-7.01 (m, 1H), 6.99-6.89 (m, 1H), 5.51-5.37 (m, 2H), 4.34 (ddd, J=37.7, 12.1, 3.1 Hz, 1H), 4.13 (dd, J=24.9, 11.9 Hz, 1H), 3.91 (s, 3H), 2.92-2.80 (m, 1H), 2.22-2.02 (m, 1H).

Example 14: 3-((R)-2-(2,5-difluorophenyl)pyrrolidin-1-yl)-N-((1s,4S)-4-hydroxycyclohexyl)-1H-pyrazolo[3,4-b]pyridine-5-carboxamide

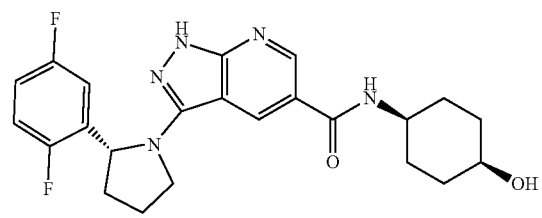 [SMILES: O=C(N[C@H]1CC[C@@H](O)CC1)c1cnc2[nH]nc(N3CCC[C@@H]3c3cc(F)ccc3F)c2c1]

MS (ESI): m/z=442 [M+H]$^+$.

$^1$H NMR (400 MHz, CD$_3$OD) δ 8.77 (d, J=2.0 Hz, 1H), 8.44 (d, J=2.0 Hz, 1H), 7.13 (td, J=9.4, 4.3 Hz, 1H), 6.98-6.87 (m, 2H), 5.42 (d, J=6.7 Hz, 1H), 4.18-4.12 (m, 1H), 3.96-3.83 (m, 2H), 3.77 (dd, J=15.9, 8.8 Hz, 1H), 3.35-3.30 (m, 1H), 2.56-2.44 (m, 1H), 2.17-1.95 (m, 3H), 1.85-1.60 (m, 7H).

Example 15: (R)—N-(3-amino-3-oxopropyl)-3-(2-(2,5-difluorophenyl)pyrrolidin-1-yl)-1H-pyrazolo[3,4-b]pyridine-5-carboxamide

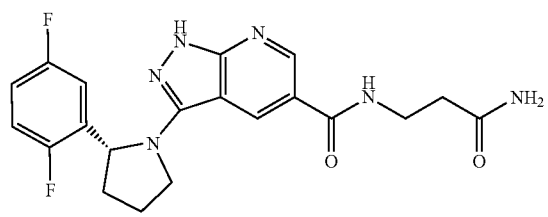 [SMILES: NC(=O)CCNC(=O)c1cnc2[nH]nc(N3CCC[C@@H]3c3cc(F)ccc3F)c2c1]

MS (ESI): m/z=442 [M+H]$^+$.

$^1$H NMR (400 MHz, CD$_3$OD) δ 8.78 (d, J=1.9 Hz, 1H), 8.53 (d, J=2.0 Hz, 1H), 7.12 (td, J=9.3, 4.2 Hz, 1H), 6.96-6.85 (m, 2H), 5.38 (d, J=6.6 Hz, 1H), 4.22-4.11 (m, 1H), 3.78 (dd, J=16.0, 8.8 Hz, 1H), 3.63 (t, J=7.0 Hz, 2H), 2.57-2.43 (m, 3H), 2.17-1.92 (m, 3H).

Example 16: N-(3-((2R,4S)-2-(2,5-difluorophenyl)-4-fluoropyrrolidin-1-yl)-1H-pyrazolo[3,4-b]pyridin-5-yl)-5-(3-hydroxy-3-methylpyrrolidin-1-yl)pyrazine-2-carboxamide

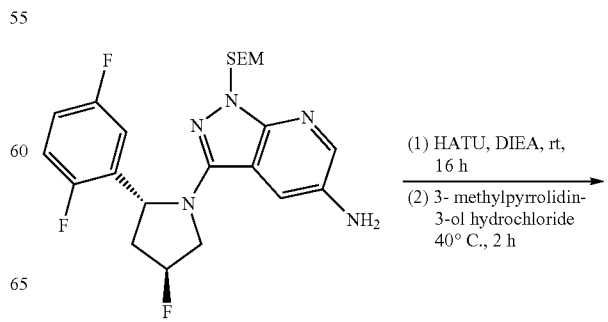

-continued

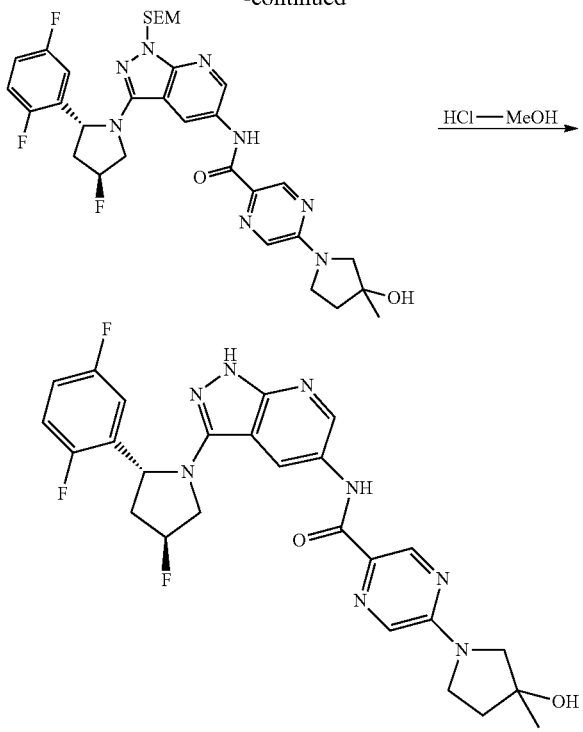

N-(3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridin-5-yl)-5-(3-hydroxy-3-methylpyrrolidin-1-yl)pyrazine-2-carboxamide To a stirred solution of 3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridin-5-amine (93 mg, 0.2 mmol) and 5-chloropyrazine-2-carboxylic acid (48 mg, 0.3 mmol) in DMF (3 mL) were added HATU (114 mg, 0.3 mmol) and DIPA (52 mg, 0.4 mmol). After the mixture was stirred overnight at room temperature, 3-methylpyrrolidin-3-ol hydrochloride (110 mg, 0.8 mmol) and DIPA (52 mg, 0.4 mmol) were added, then stirred further 2 h at 40° C. The mixture was diluted with EtOAc (20 mL), washed with water (2×20 mL) and brine (1×20 mL), dried over anhydrous Na$_2$SO$_4$, filtered and concentrated. The resulting dryness was purified by column chromatography (eluting with 0-6% MeOH/DCM) to afford product 85 mg (60% yield) as a yellow solid.

MS (ESI): m/z=691 [M+H]$^+$.

N-(3-((2R,4S)-2-(2,5-Difluorophenyl)-4-fluoropyrrolidin-1-yl)-1H-pyrazolo[3,4-b]pyridin-5-yl)-5-(3-hydroxy-3-methylpyrrolidin-1-yl)pyrazine-2-carboxamide

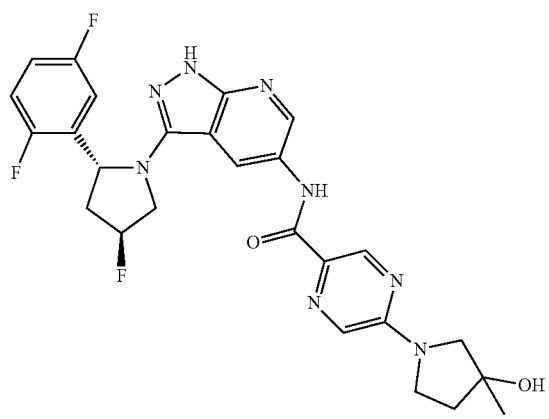 [SMILES: CC1(O)CCN(c2cnc(C(=O)Nc3cnc4[nH]nc(N5C[C@@H](F)C[C@@H]5c5cc(F)ccc5F)c4c3)cn2)C1]

A solution of N-(3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridin-5-yl)-5-(3-hydroxy-3-methylpyrrolidin-1-yl)pyrazine-2-carboxamide (30 mg, 0.045 mmol) in HCl in MeOH (3M, 3 mL) was stirred at r.t. for 1 hr. After removal of solvent, the resulting residue was purified by reverse phase column chromatography to afford product (9.0 mg, yield 35.5%) as a white solid.

MS (ESI): m/z=539 [M+H]$^+$.

$^1$H NMR (400 MHz, CD$_3$OD) δ 8.75 (s, 1H), 8.59 (d, J=2.2 Hz, 2H), 7.95 (s, 1H), 7.18-6.99 (m, 2H), 6.92 (d, J=8.2 Hz, 1H), 5.53-5.33 (m, 2H), 4.37 (dd, J=36.7, 10.8 Hz, 1H), 4.09 (dd, J=25.1, 10.7 Hz, 1H), 3.73 (s, 2H), 3.67-3.54 (m, 1H), 3.45 (d, J=11.5 Hz, 1H), 2.85 (s, 1H), 2.08 (t, J=20.5 Hz, 3H), 1.48 (s, 3H).

Example 17: 3-((2R,4S)-2-(2,5-difluorophenyl)-4-fluoropyrrolidin-1-yl)-1H-pyrazolo[3,4-b]pyridine-5-carboxylic acid

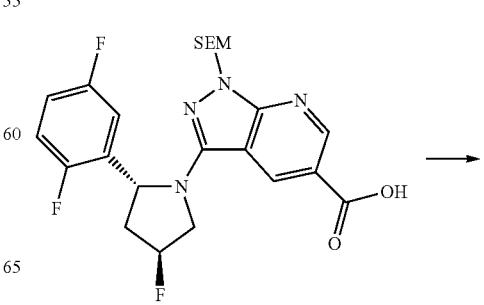

-continued

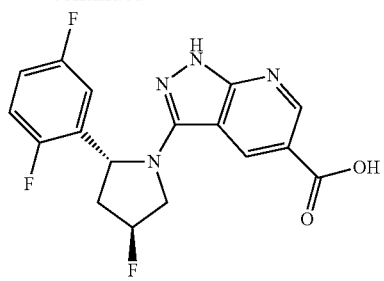

3-((2R,4S)-2-(2,5-difluorophenyl)-4-fluoropyrrolidin-1-yl)-1H-pyrazolo[3,4-b]pyridine-5-carboxylic acid was prepared using a method similar to that example 13 by replacing the corresponding starting material.

MS (ESI): m/z=363 [M+H]+.

¹H NMR (400 MHz, DMSO-d₆) δ 12.61 (s, 2H), 8.85 (d, J=1.8 Hz, 1H), 8.56 (d, J=1.8 Hz, 1H), 7.26-7.10 (m, 2H), 7.10-6.98 (m, 1H), 5.48 (d, J=52.8 Hz, 1H), 5.36-5.24 (m, 1H), 4.43 (dd, J=38.2, 10.6 Hz, 1H), 3.98 (dd, J=25.8, 11.9 Hz, 1H), 2.78-2.60 (m, 1H), 2.07 (dt, J=42.1, 10.6 Hz, 1H).

Example 18

3-((2R,4S)-2-(2,5-difluorophenyl)-4-fluoropyrrolidin-1-yl)-N,N-dimethyl-1H-pyrazolo[3,4-b]pyridine-5-carboxamide

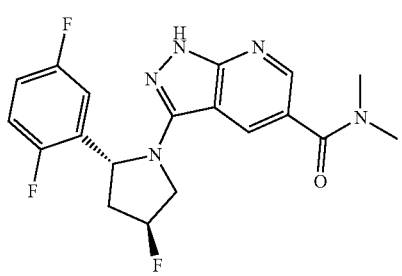 [SMILES: CN(C)C(=O)c1cnc2[nH]nc(N3C[C@@H](F)C[C@@H]3c3cc(F)ccc3F)c2c1]

3-((2R,4S)-2-(2,5-difluorophenyl)-4-fluoropyrrolidin-1-yl)-N,N-dimethyl-1H-pyrazolo[3,4-b]pyridine-5-carboxamide was prepared using a method similar to that example 4 by replacing the corresponding starting material.

MS (ESI): m/z=390 [M+H]+.

¹H NMR (400 MHz, DMSO-d6) δ 12.54 (s, 1H), 8.41 (d, J=1.8 Hz, 1H), 8.18 (d, J=1.7 Hz, 1H), 7.24-7.03 (m, 3H), 5.47 (d, J=52.4 Hz, 1H), 5.36-5.21 (m, 1H), 4.39 (dd, J=38.5, 11.0 Hz, 1H), 3.95 (dd, J=26.2, 12.5 Hz, 1H), 2.97 (s, 6H), 2.76-2.60 (m, 1H), 2.18-1.95 (m, 1H).

Example 19: isopropyl 3-((2R,4S)-2-(2,5-difluorophenyl)-4-fluoropyrrolidin-1-yl)-1H-pyrazolo[3,4-b]pyridine-5-carboxylate

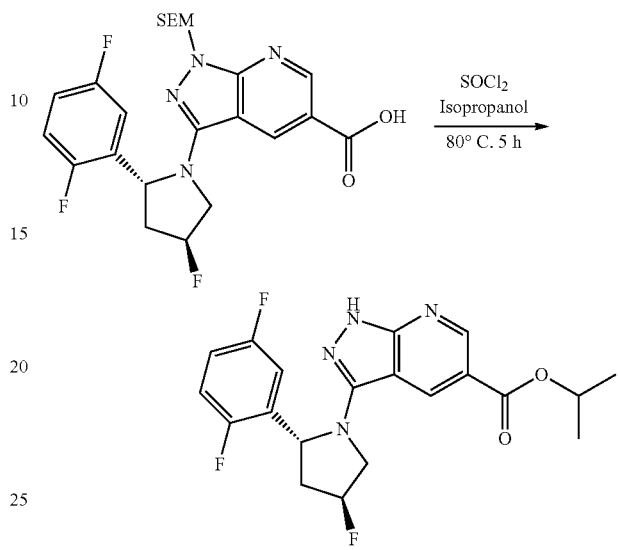

The mixture of 3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine-5-carboxylic acid (60 mg, 0.122 mmol), SOCl₂ (0.5 mL) in isopropanol (40 mL) was stirred at 80° C. for 5 h. Then it was concentrated, and purified by prep-HPLC to give isopropyl 3-((2R,4S)-2-(2,5-difluorophenyl)-4-fluoropyrrolidin-1-yl)-1H-pyrazolo[3,4-b]pyridine-5-carboxylate (21.8 mg, 44.2%) as a yellow solid.

MS (ESI): m/z=405 [M+H]+.

¹H NMR (400 MHz, DMSO-d₆) δ 12.75 (s, 1H), 8.83 (d, J=1.9 Hz, 1H), 8.48 (d, J=1.9 Hz, 1H), 7.28-7.13 (m, 2H), 7.12-7.04 (m, 1H), 5.49 (d, J=53.1 Hz, 1H), 5.40-5.28 (m, 1H), 5.15-5.08 (m, 1H), 4.37 (dd, J=37.9, 10.4 Hz, 1H), 4.02 (dd, J=23.8, 12.1 Hz, 1H), 2.90-2.67 (m, 1H), 2.17-1.99 (m, 1H), 1.30 (dd, J=6.1, 4.2 Hz, 6H).

Example 20: 3-((2R,4S)-2-(2,5-difluorophenyl)-4-fluoropyrrolidin-1-yl)-5-(1H-pyrazol-4-yl)-1H-pyrazolo[3,4-b]pyridine

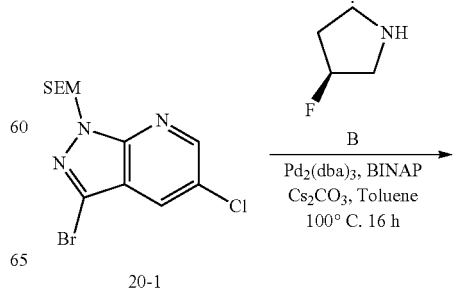

20-1

-continued

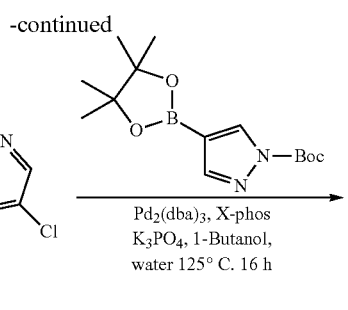

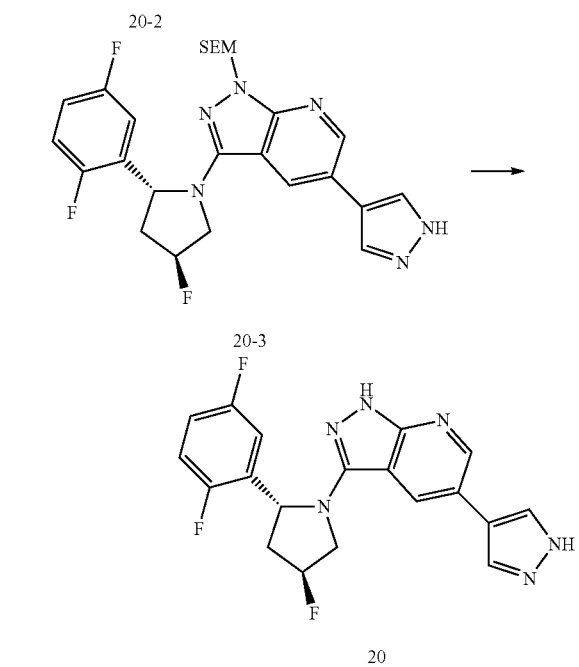

5-Chloro-3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine

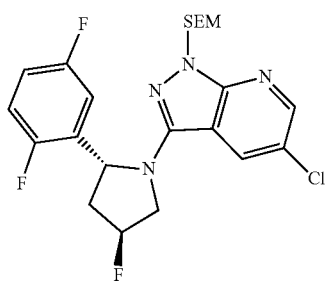 [SMILES: C[Si](C)(C)CCOCn1nc(N2C[C@@H](F)C[C@@H]2c2cc(F)ccc2F)c2cc(Cl)cnc21]

To a screw-capped vial was added 3-bromo-5-chloro-1-((2-(trimethylsilyl)ethoxy)methyl)-1H-pyrazolo [3,4-b]pyridine (120 mg, 0.331 mmol), (2R,4S)-2-(2,5-difluorophenyl)-4-fluoropyrrolidine (66 mg, 0.331 mmol), Pd₂(dba)₃ (30 mg, 0.0331 mmol), BINAP (41 mg, 0.0662 mmol), Cs₂CO₃ (216 mg, 0.662 mmol) and Toluene (6 mL). The mixture was stirred at 100° C. for 16 h. The mixture was diluted with EtOAc (50 mL), washed with water (50 mL*2), dried over Na₂SO₄, filtered. The filtrate was concentrated and purified by column chromatography (petroleumn ether/EtOAc=8/1) to give 5-chloro-3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine (81 mg, yield 52.6%) as yellow oil.

MS (ESI): m/z=365 [M+H]⁺.

3-((2R,4S)-2-(2,5-Difluorophenyl)-4-fluoropyrrolidin-1-yl)-5-(1H-pyrazol-4-yl)-1-((2-(trimethylsilyl)ethoxy)methyl)-1H-pyrazolo[3,4-b]pyridine

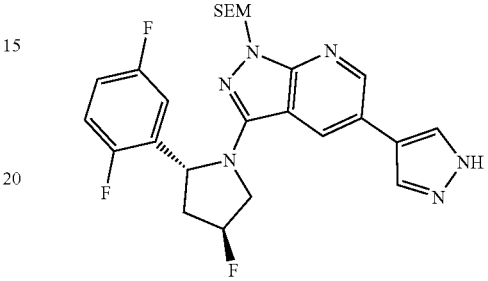

To a screw-capped vial was added 5-chloro-3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine (70 mg, 0.150 mmol), tert-butyl 4-(4,4,5,5-tetramethyl-1,3,2-dioxaborolan-2-yl)-1H-pyrazole-1-carboxylate (133 mg, 0.452 mmol), Pd₂(dba)₃ (27 mg, 0.030 mmol), K₃PO₄ (159 mg, 0.75 mmol) and 1-Butanol (5 mL), water (1 mL). The mixture was stirred at 125° C. for 16 h. It was added water (50 mL), extracted with DCM (50 mL*2). The combined organic layer was dried over Na₂SO₄, filtered. The filtrate was concentrated and purified by column chromatography (petroleumn ether/EtOAc=1/1) to give 3-((2R,4S)-2-(2,5-difluorophenyl)-4-fluoropyrrolidin-1-yl)-5-(1H-pyrazol-4-yl)-1-((2-(trimethylsilyl)ethoxy)methyl)-1H-pyrazolo[3,4-b]pyridine (70 mg, yield 90.7%) as yellow oil.

MS (ESI): m/z=397 [M+H]⁺.

3-((2R,4S)-2-(2,5-Difluorophenyl)-4-fluoropyrrolidin-1-yl)-5-(1H-pyrazol-4-yl)-1H-pyrazolo[3,4-b]pyridine

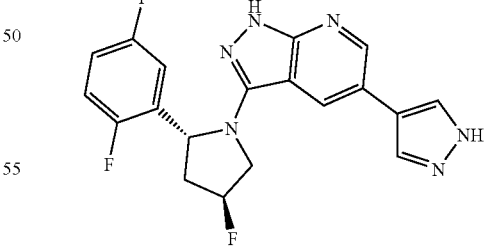

3-((2R,4S)-2-(2,5-difluorophenyl)-4-fluoropyrrolidin-1-yl)-5-(1H-pyrazol-4-yl)-1H-pyrazolo[3,4-b]pyridine was prepared using a method similar to that example 13 by replacing the corresponding starting material.

MS (ESI): m/z=385 [M+H]⁺.

¹H NMR (400 MHz, DMSO-d₆) δ 12.90 (s, 1H), 12.25 (s, 1H), 8.67 (d, J=2.0 Hz, 1H), 8.24 (s, 1H), 8.22-7.98 (m, 2H), 7.25-7.18 (m, 1H), 7.17-7.12 (m, 1H), 7.09-7.01 (m, 1H), 5.50 (d, J=52.8 Hz, 1H), 5.36-5.27 (m, 1H), 4.44 (dd, J=40.1, 12.4 Hz, 1H), 3.98 (dd, J=26.7, 12.0 Hz, 1H), 2.77-2.60 (m, 1H), 2.18-2.00 (m, 1H).

Example 21

3-((2R,4S)-2-(2,5-difluorophenyl)-4-fluoropyrrolidin-1-yl)-5-(2H-tetrazol-5-yl)-1H-pyrazolo[3,4-b]pyridine

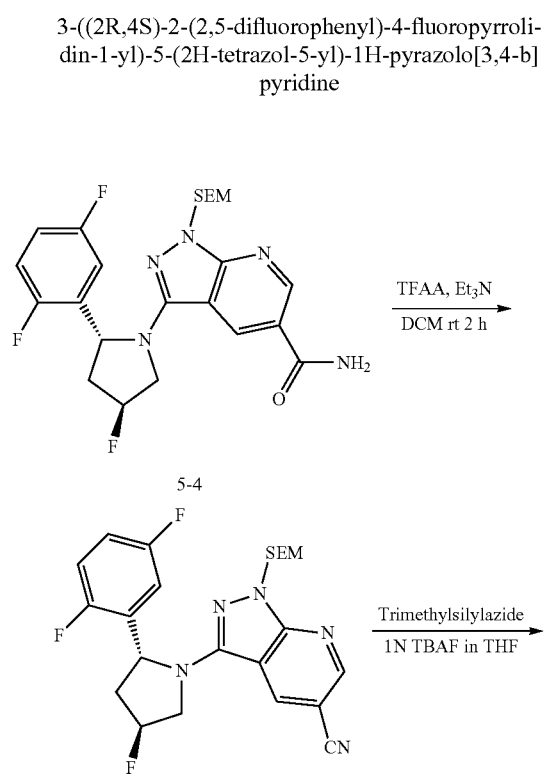

3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine-5-carbonitrile

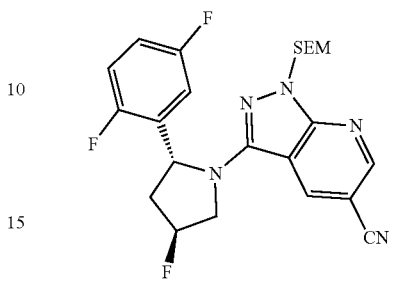

The mixture of 3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine-5-carboxamide (100 mg, 0.20 mmol) and Et$_3$N (202 mg, 2.0 mmol) in DCM (3 mL) was added TFAA (126 mg, 0.60 mmol) and then stirred at r.t. for 2 h. It was concentrated and purified by column chromatography (petroleumn ether/EtOAc=4/1) to give 3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine-5-carbonitrile (70 mg, yield 73.9%) as a yellow solid.

MS (ESI): m/z=356 [M–SEM+CH$_3$]$^+$.

3-((2R,4S)-2-(2,5-difluorophenyl)-4-fluoropyrrolidin-1-yl)-5-(2H-tetrazol-5-yl)-1-((2-(trimethylsilyl)ethoxy)methyl)-1H-pyrazolo[3,4-b]pyridine

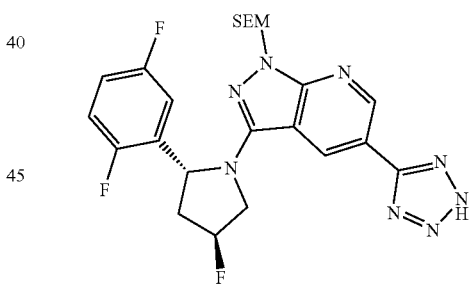

To the mixture of 3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine-5-carbonitrile (70 mg, 0.15 mmol) and 1N TBAF in THF (0.75 ml, 0.75 mmol) in DMF (2 mL) was added Trimethylsilylazide (86 mg, 0.75 mmol) and the mixture was stirred at 90° C. for 16 h. It was diluted with water (50 mL), extracted with EA (50 ml*l). The organic layer was dried over Na$_2$SO$_4$ and filtered. The filtrate was concentrated and purified by column chromatography (DCM/methanol=10/1) to give 3-((2R,4S)-2-(2,5-difluorophenyl)-4-fluoropyrrolidin-1-yl)-5-(2H-tetrazol-5-yl)-1-((2-(trimethylsilyl)ethoxy)methyl)-1H-pyrazolo[3,4-b]pyridine (70 mg, 90.3%) as yellow solid.

MS (ESI): m/z=399 [M–SEM+CH$_3$]$^+$.

3-((2R,4S)-2-(2,5-difluorophenyl)-4-fluoropyrrolidin-1-yl)-5-(2H-tetrazol-5-yl)-1H-pyrazolo[3,4-b]pyridine

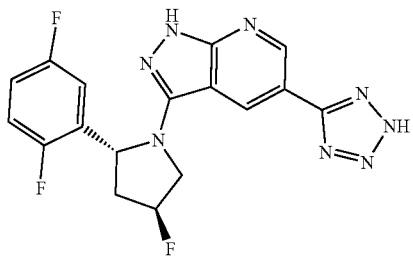 [SMILES: Fc1ccc(F)c([C@H]2C[C@H](F)CN2c2n[nH]c3ncc(-c4nn[nH]n4)cc23)c1]

3-((2R,4S)-2-(2,5-difluorophenyl)-4-fluoropyrrolidin-1-yl)-5-(2H-tetrazol-5-yl)-1H-pyrazolo[3,4-b]pyridine was prepared using a method similar to that example 13 by replacing the corresponding starting material.

MS (ESI): m/z=387 [M+H]+.

$^1$H NMR (400 MHz, DMSO-$d_6$) δ 12.62 (s, 1H), 8.99 (d, J=1.9 Hz, 1H), 8.71 (d, J=1.5 Hz, 1H), 7.24-7.16 (m, 2H), 7.08-7.03 (m, 1H), 5.53 (d, J=52.8 Hz, 1H), 5.31 (dd, J=9.8, 6.8 Hz, 1H), 4.58-4.35 (m, 1H), 4.02 (dd, J=25.8, 11.9 Hz, 1H), 2.80-2.66 (m, 1H), 2.21-1.99 (m, 1H).

Example 22

3-((2R,4S)-2-(2,5-difluorophenyl)-4-fluoropyrrolidin-1-yl)-5-(1-(piperidin-4-yl)-1H-pyrazol-4-yl)-1H-pyrazolo[3,4-b]pyridine

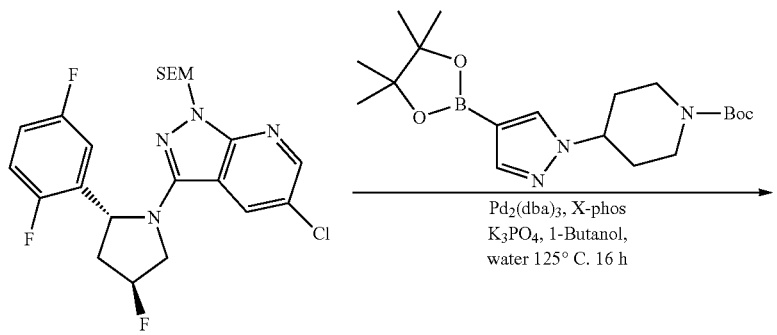

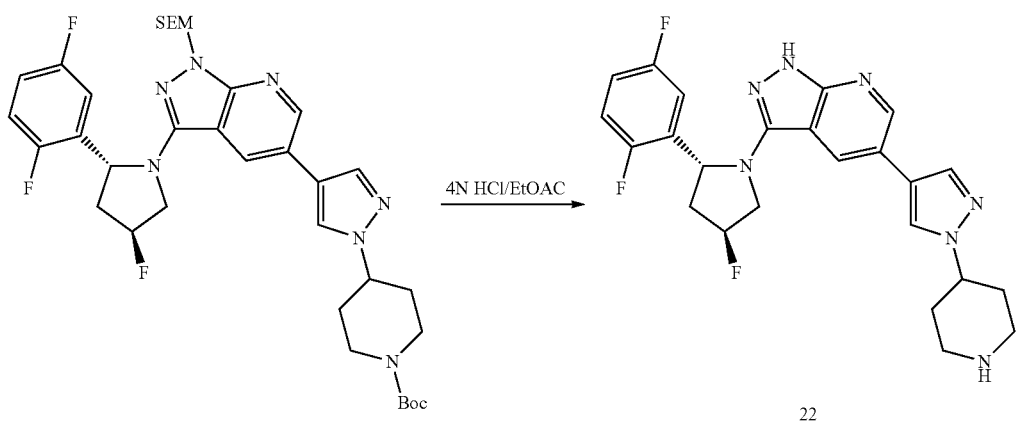

3-((2R,4S)-2-(2,5-difluorophenyl)-4-fluoropyrrolidin-1-yl)-5-(1-(piperidin-4-yl)-1H-pyrazol-4-yl)-1H-pyrazolo[3,4-b]pyridine was prepared using a method similar to that example 20 by replacing the corresponding starting material.

MS (ESI): m/z=468 [M+H]+.

1H NMR (400 MHz, DMSO-d6) δ 12.26 (s, 1H), 8.65 (d, J=2.0 Hz, 1H), 8.29 (s, 1H), 8.23 (d, J=1.9 Hz, 1H), 7.91 (s, 1H), 7.21 (d, J=4.3 Hz, 1H), 7.18-7.11 (m, 1H), 7.10-7.01 (m, 1H), 5.50 (d, J=53.4 Hz, 1H), 5.31 (dd, J=10.0, 6.9 Hz, 1H), 4.55-4.34 (m, 1H), 4.21-4.09 (m, 1H), 3.98 (dd, J=26.2, 11.9 Hz, 1H), 3.02 (d, J=12.6 Hz, 2H), 2.77-2.64 (m, 1H), 2.57 (t, J=11.2 Hz, 1H), 2.20-1.92 (m, 3H), 1.83-1.71 (m, 2H).

Example 23

4-(4-(3-((2R,4S)-2-(2,5-difluorophenyl)-4-fluoropyrrolidin-1-yl)-1H-pyrazolo[3,4-b]pyridin-5-yl)-1H-pyrazol-1-yl)piperidin-2-one

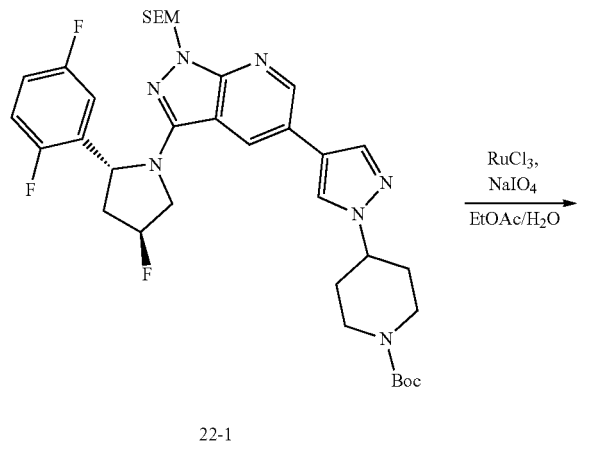

22-1

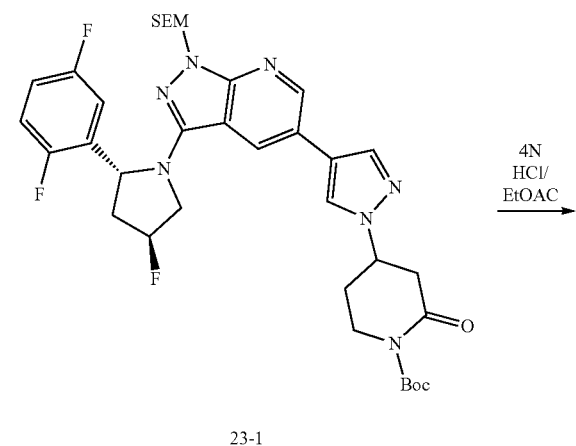

23-1

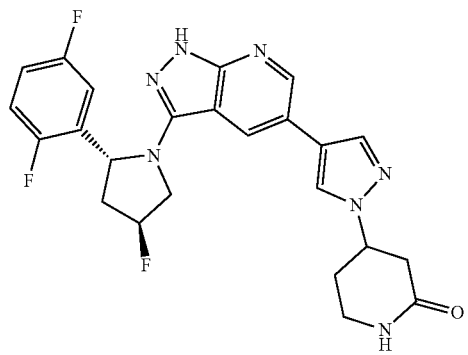

23

Tert-butyl 4-(4-(3-((2R,4S)-2-(2,5-difluorophenyl)-4-fluoropyrrolidin-1-yl)-1H-pyrazolo[3,4-b]pyridin-5-yl)-1H-pyrazol-1-yl)-2-oxopiperidine-1-carboxylate A mixture of tert-butyl 4-(4-(3-((2R,4S)-2-(2,5-difluorophenyl)-4-fluoropyrrolidin-1-yl)-1H-pyrazolo[3,4-b]pyridin-5-yl)-1H-pyrazol-1-yl)piperidine-1-carboxylate (180 mg, 0.26 mmol), NaIO4 (280 mg, 1.30 mmol) and RuCl3H2O (10 mg) in EtOAc (4 mL) and H2O (4 mL) was stirred at r.t. for 1.5 h. The mixture was washed with Na2S2O3 solution and brine. The mixture was dried and filtered. The filtrate was concentrated and purified by column chromatography (petroleumn ether/EtOAc=1/1) to afford tert-butyl 4-(4-(3-((2R,4S)-2-(2,5-difluorophenyl)-4-fluoropyrrolidin-1-yl)-1H-pyrazolo[3,4-b]pyridin-5-yl)-1H-pyrazol-1-yl)-2-oxopiperidine-1-carboxylate (68 mg, yield 37%).

MS (ESI): m/z=734 [M+Na]+.

63
4-(4-(3-((2R,4S)-2-(2,5-difluorophenyl)-4-fluoropyrrolidin-1-yl)-1H-pyrazolo[3,4-b]pyridin-5-yl)-1H-pyrazol-1-yl)piperidin-2-one

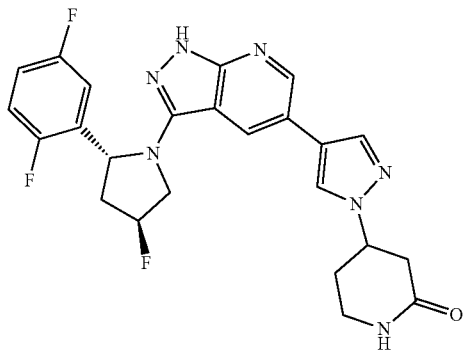 [SMILES: O=C1CC(n2cc(-c3cnc4[nH]nc(N5C[C@@H](F)C[C@@H]5c5cc(F)ccc5F)c4c3)cn2)CCN1]

4-(4-(3-((2R,4S)-2-(2,5-difluorophenyl)-4-fluoropyrrolidin-1-yl)-1H-pyrazolo[3,4-b]pyridin-5-yl)-1H-pyrazol-1-yl)piperidin-2-one was prepared using a method similar to that example 13 by replacing the corresponding starting material.

MS (ESI): m/z=482 [M+H]+.

$^1$H NMR (400 MHz, DMSO-d$_6$) δ 13.51-13.29 (m, 1H), 8.78 (d, J=2.1 Hz, 1H), 8.57 (d, J=2.1 Hz, 1H), 8.27 (s, 1H), 7.88 (s, 1H), 7.31-7.14 (m, 2H), 7.09 (m, 1H), 5.88-5.81 (m, 1H), 5.69 (dt, J=52.3, 7.5 Hz, 1H), 4.28-4.17 (m, 1H), 3.05 (d, J=12.8 Hz, 2H), 3.01-2.84 (m, 1H), 2.69-2.54 (m, 3H), 1.98 (d, J=10.4 Hz, 2H), 1.82 (dt, J=12.1, 8.4 Hz, 2H),

Example 24: 3-((2R,4S)-2-(2,5-difluorophenyl)-4-fluoropyrrolidin-1-yl)-5-(1-((R)-pyrrolidin-3-yl)-1H-pyrazol-4-yl)-1H-pyrazolo[3,4-b]pyridine

64

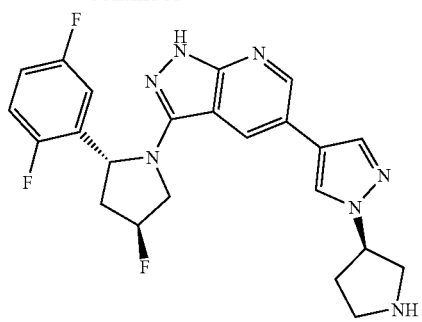

3-((2R,4S)-2-(2,5-difluorophenyl)-4-fluoropyrrolidin-1-yl)-5-(1-((R)-pyrrolidin-3-yl)-1H-pyrazol-4-yl)-1H-pyrazolo[3,4-b]pyridine was prepared using a method similar to that example 20 by replacing the corresponding starting material.

MS (ESI): m/z=454 [M+H]+.

$^1$H NMR (400 MHz, CD$_3$OD) δ 8.58 (d, J=2.0 Hz, 1H), 8.14 (d, J=2.0 Hz, 1H), 8.08 (s, 1H), 7.82 (s, 1H), 7.15-7.03 (m, 2H), 6.97-6.88 (m, 1H), 5.58-5.35 (m, 2H), 5.00-4.91 (m, 1H), 4.36 (dd, J=37.9, 12.4 Hz, 1H), 4.10 (dd, J=25.2, 12.3 Hz, 1H), 3.32-3.30 (m, 1H), 3.26-3.18 (m, 2H), 3.06-2.96 (m, 1H), 2.92-2.80 (m, 1H), 2.40-2.32 (m, 1H), 2.25-1.99 (m, 2H).

Example 25: 3-((2R,4S)-2-(2,5-difluorophenyl)-4-fluoropyrrolidin-1-yl)-5-(1-((S)-pyrrolidin-3-yl)-1H-pyrazol-4-yl)-1H-pyrazolo[3,4-b]pyridine

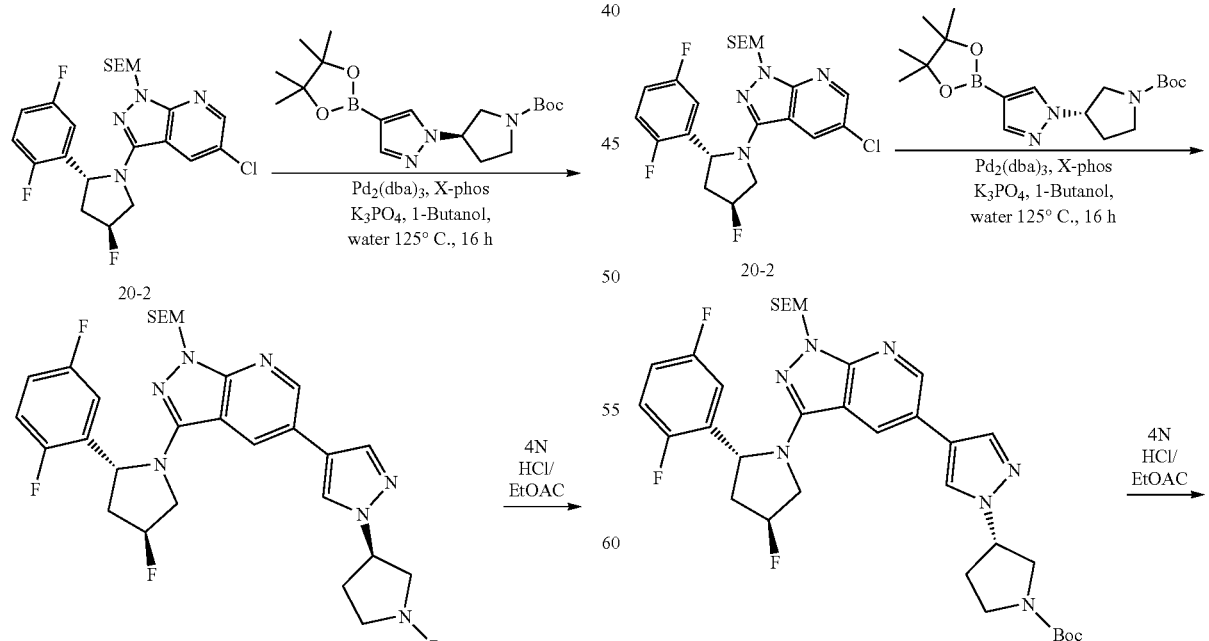

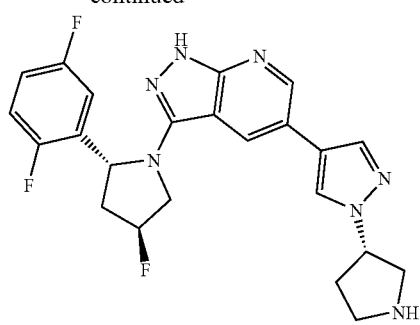

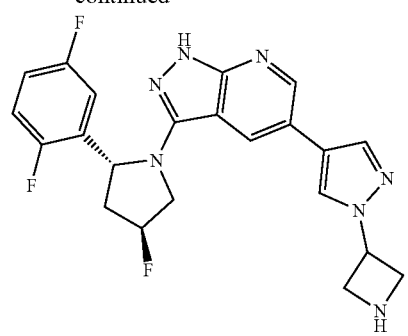

3-((2R,4S)-2-(2,5-difluorophenyl)-4-fluoropyrrolidin-1-yl)-5-(1-((S)-pyrrolidin-3-yl)-1H-pyrazol-4-yl)-1H-pyrazolo[3,4-b]pyridine was prepared using a method similar to that example 20 by replacing the corresponding starting material.

MS (ESI): m/z=454 [M+H]+.

1H NMR (400 MHz, CD3OD) δ 8.58 (d, J=2.0 Hz, 1H), 8.14 (d, J=2.0 Hz, 1H), 8.08 (s, 1H), 7.82 (s, 1H), 7.16-7.02 (m, 2H), 6.96-6.90 (m, 1H), 5.55-5.34 (m, 2H), 5.00-4.91 (m, 1H), 4.46-4.26 (m, 1H), 4.10 (dd, J=24.9, 12.0 Hz, 1H), 3.27-3.14 (m, 3H), 3.07-2.97 (m, 1H), 2.93-2.78 (m, 1H), 2.42-2.32 (m, 1H), 2.25-2.00 (m, 2H).

Example 26: 5-(1-(azetidin-3-yl)-1H-pyrazol-4-yl)-3-((2R,4S)-2-(2,5-difluorophenyl)-4-fluoropyrrolidin-1-yl)-1H-pyrazolo[3,4-b]pyridine 5-(1-(Azetidin-3-yl)-1H-pyrazol-4-yl)-3-((2R,4S)-2-(2,5-difluorophenyl)-4-fluoropyrrolidin-1-yl)-1H-pyrazolo[3,4-b]pyridine was prepared using a method similar to that example 20 by replacing the corresponding starting material.

MS (ESI): m/z=441 [M+H]+.

1H NMR (400 MHz, CD3OD) δ 8.58 (d, J=2.0 Hz, 1H), 8.18-8.12 (m, 2H), 7.89 (s, 1H), 7.16-7.02 (m, 2H), 6.97-6.89 (m, 1H), 5.54-5.34 (m, 2H), 5.34-5.26 (m, 1H), 4.43-4.20 (m, 1H), 4.20-4.13 (m, 2H), 4.13-4.04 (m, 1H), 4.03-3.98 (m, 2H), 2.95-2.78 (m, 1H), 2.19-2.00 (m, 1H).

Example 27: 3-((2R,4S)-2-(2,5-difluorophenyl)-4-fluoropyrrolidin-1-yl)-5-(1-(methylsulfonyl)-1H-pyrazol-4-yl)-1H-pyrazolo[3,4-b]pyridine

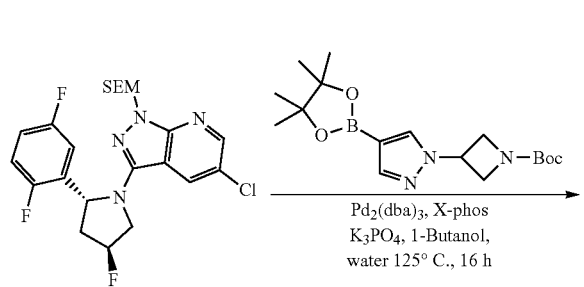

20-2

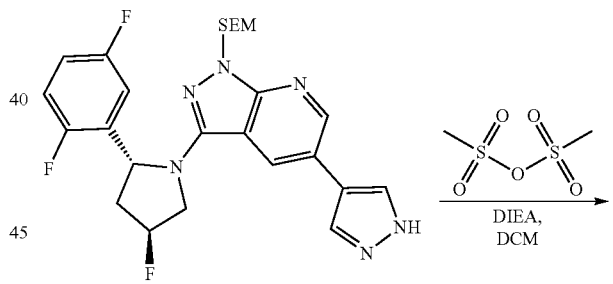

20-3

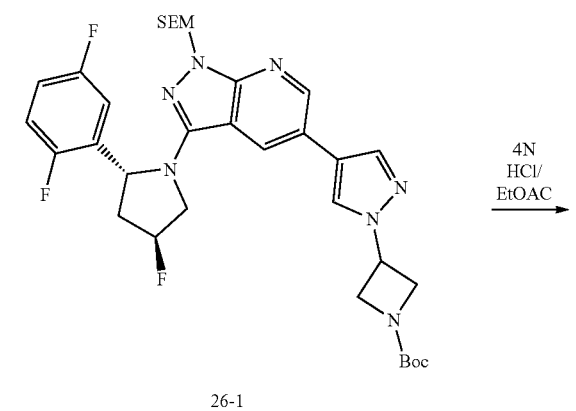

26-1

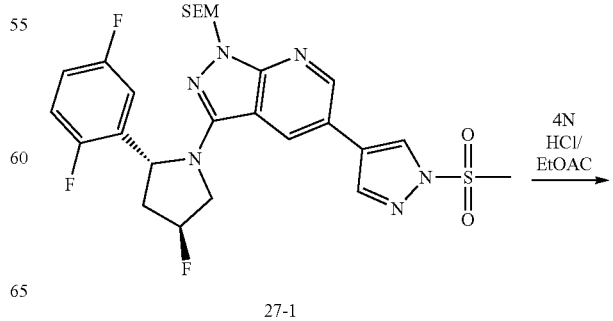

27-1

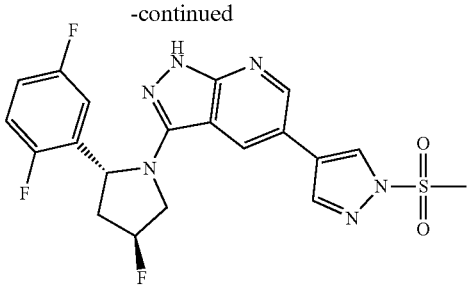

27

3-((2R,4S)-2-(2,5-difluorophenyl)-4-fluoropyrroli-
din-1-yl)-5-(1-(methylsulfonyl)-1H-pyrazol-4-yl)-1-
((2-(trimethylsilyl)ethoxy)methyl)-1H-pyrazolo[3,4-
b]pyridine

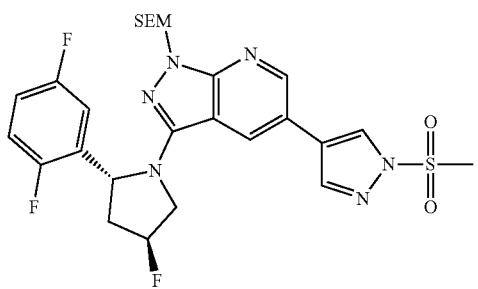 [SMILES: C[Si](C)(C)CCOCn1nc(N2C[C@@H](F)C[C@@H]2c2cc(F)ccc2F)c2cc(-c3cnn(S(C)(=O)=O)c3)cnc21]

To the mixture of 3-((2R,4S)-2-(2,5-difluorophenyl)-4-fluoropyrrolidin-1-yl)-5-(1H-pyrazol-4-yl)-1-((2-(trimethylsilyl)ethoxy)methyl)-1H-pyrazolo[3,4-b]pyridine (90 mg, 0.175 mmol), DIEA (136 mg, 1.05 mmol) in DCM (5 mL) was added methanesulfonic anhydride (91 mg, 0.525 mmol). The mixture was stirred at r.t. for 1 h. It was quenched with water (50 ml), extracted with DCM (50 mL*2). The combined organic layer was dried over, filtered. The filtrate was concentrated to give 3-((2R,4S)-2-(2,5-difluorophenyl)-4-fluoropyrrolidin-1-yl)-5-(1-(methylsulfonyl)-1H-pyrazol-4-yl)-1-((2-(trimethylsilyl)ethoxy)methyl)-1H-pyrazolo[3,4-b]pyridine (100 mg, 96.4%) as yellow oil.

MS (ESI): m/z=593 [M+H]+.

3-((2R,4S)-2-(2,5-difluorophenyl)-4-fluoropyrroli-
din-1-yl)-5-(1-(methylsulfonyl)-1H-pyrazol-4-yl)-
1H-pyrazolo[3,4-b]pyridine

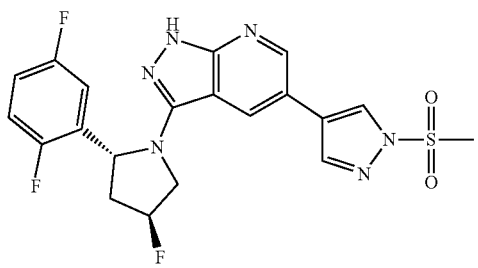 [SMILES: CS(=O)(=O)n1cc(-c2cnc3[nH]nc(N4C[C@@H](F)C[C@@H]4c4cc(F)ccc4F)c3c2)cn1]

3-((2R,4S)-2-(2,5-difluorophenyl)-4-fluoropyrrolidin-1-
yl)-5-(1-(methylsulfonyl)-1H-pyrazol-4-yl)-1H-pyrazolo[3,
4-b]pyridine was prepared using a method similar to that example 13 by replacing the corresponding starting material.

MS (ESI): m/z=463 [M+H]+.

1H NMR (400 MHz, CD3OD) δ 8.66 (d, J=1.9 Hz, 1H), 8.56 (s, 1H), 8.30-8.24 (m, 2H), 7.15-7.02 (m, 2H), 6.97-6.89 (m, 1H), 5.54-5.35 (m, 2H), 4.45-4.32 (m, 1H), 4.12 (dd, J=24.4, 11.5 Hz, 1H), 3.44 (s, 3H), 2.93-2.78 (m, 1H), 2.19-1.99 (m, 1H).

Example 28: 3-((2R,4S)-2-(2,5-difluorophenyl)-4-
fluoropyrrolidin-1-yl)-5-(1-(tetrahydro-2H-pyran-4-
yl)-1H-pyrazol-4-yl)-1H-pyrazolo[3,4-b]pyridine

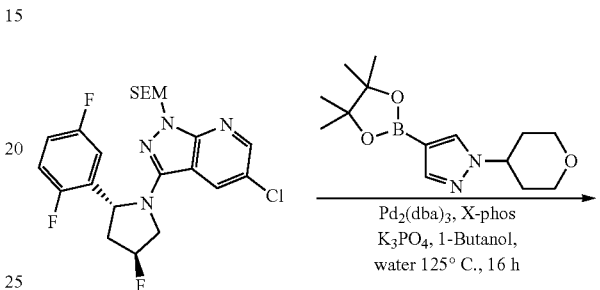

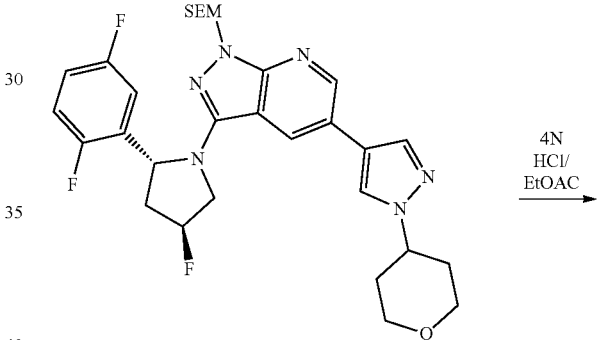

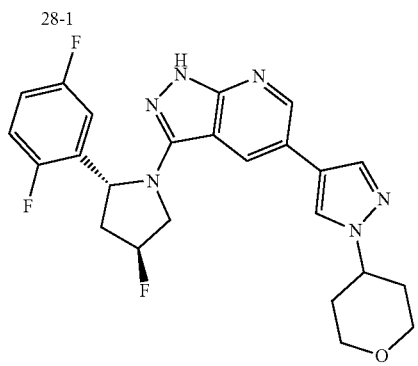

3-((2R,4S)-2-(2,5-Difluorophenyl)-4-fluoropyrrolidin-1-yl)-5-(1-(tetrahydro-2H-pyran-4-yl)-1H-pyrazol-4-yl)-1H-pyrazolo[3,4-b]pyridine was prepared using a method similar to that example 20 by replacing the corresponding starting material.

MS (ESI): m/z=469 [M+H]+.

1H NMR (400 MHz, CD3OD) δ 8.58 (d, J=2.0 Hz, 1H), 8.14 (d, J=2.0 Hz, 1H), 8.10 (d, J=0.5 Hz, 1H), 7.82 (d, J=0.7 Hz, 1H), 7.15-7.03 (m, 2H), 6.97-6.89 (m, 1H), 5.54-5.36

(m, 2H), 4.48-4.28 (m, 2H), 4.16-4.04 (m, 3H), 3.62-3.55 (m, 2H), 2.93-2.80 (m, 1H), 2.19-1.99 (m, 5H).

Example 29: 3-((2R,4S)-2-(2,5-difluorophenyl)-4-fluoropyrrolidin-1-yl)-5-(1-(1-methylazetidin-3-yl)-1H-pyrazol-4-yl)-1H-pyrazolo[3,4-b]pyridine

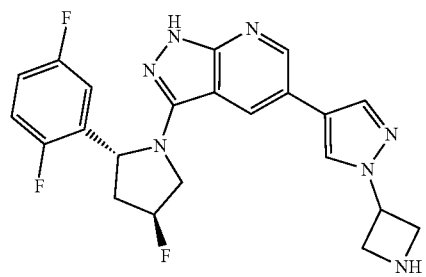

28

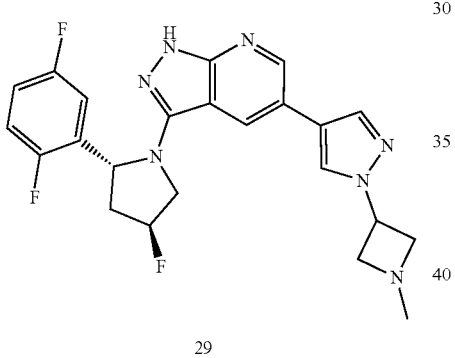

29

The mixture of 5-(1-(azetidin-3-yl)-1H-pyrazol-4-yl)-3-((2R,4S)-2-(2,5-difluorophenyl)-4-fluoropyrrolidin-1-yl)-1H-pyrazolo[3,4-b]pyridine (100 mg, 0.149 mmol), 30% formaldehyde (0.4 mL), $CH_3COOH$ (0.05 mL) in DCM (5 mL) and methanol (5 mL) was stirred at r.t. for 2 h. Then $NaBH(OAc)_3$ (253 mg, 1.19 mmol) was added at 0° C. and stirred at 0° C. for 1 h. It was concentrated and purified by reverse phase column chromatography to give 3-((2R,4S)-2-(2,5-difluorophenyl)-4-fluoropyrrolidin-1-yl)-5-(1-(1-methylazetidin-3-yl)-1H-pyrazol-4-yl)-1H-pyrazolo[3,4-b]pyridine (25 mg, 37.0%) as a yellow solid.

MS (ESI): m/z=454 [M+H]+.

$^1$H NMR (400 MHz, $CD_3OD$) δ 8.58 (d, J=2.0 Hz, 1H), 8.15 (d, J=0.8 Hz, 2H), 7.87 (s, 1H), 7.14-7.04 (m, 2H), 6.98-6.87 (m, 1H), 5.56-5.34 (m, 2H), 5.09-4.99 (m, 1H), 4.45-4.28 (m, 1H), 4.10 (dd, J=24.1, 11.4 Hz, 1H), 3.89 (td, J=7.3, 1.7 Hz, 2H), 3.65 (t, J=7.6 Hz, 2H), 2.93-2.79 (m, 1H), 2.49 (s, 3H), 2.19-2.02 (m, 1H).

Example 30: 5-(1-(2,2-difluoroethyl)-1H-pyrazol-4-yl)-3-((2R,4S)-2-(2,5-difluorophenyl)-4-fluoropyrrolidin-1-yl)-1H-pyrazolo[3,4-b]pyridine

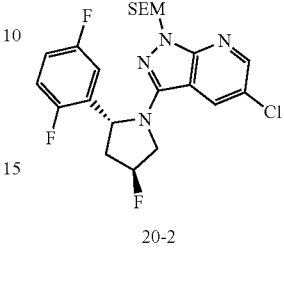 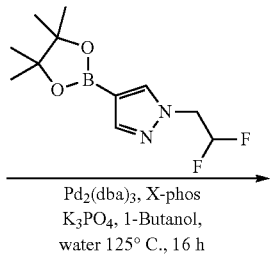

20-2

Pd$_2$(dba)$_3$, X-phos
K$_3$PO$_4$, 1-Butanol,
water 125° C., 16 h

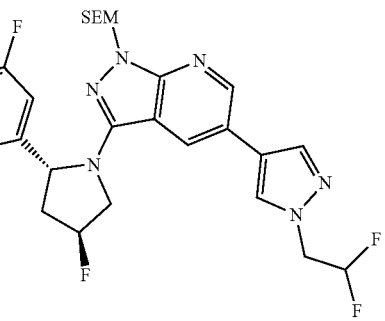

30-1

4N HCl/ EtOAC

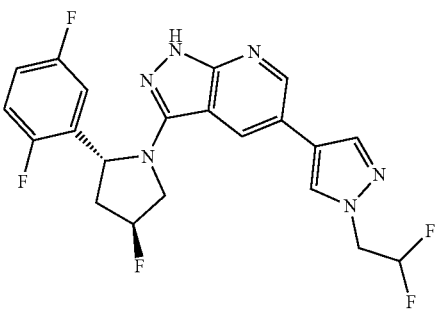

30

5-(1-(2,2-Difluoroethyl)-1H-pyrazol-4-yl)-3-((2R,4S)-2-(2,5-difluorophenyl)-4-fluoropyrrolidin-1-yl)-1H-pyrazolo[3,4-b]pyridine was prepared using a method similar to that example 20 by replacing the corresponding starting material.

MS (ESI): m/z=449 [M+H]+.

$^1$H NMR (400 MHz, $CD_3OD$) δ 8.58 (d, J=1.9 Hz, 1H), 8.14 (d, J=2.0 Hz, 1H), 8.06 (s, 1H), 7.88 (s, 1H), 7.13-7.02 (m, 2H), 6.96-6.90 (m, 1H), 6.21 (tt, J=55.2, 3.8 Hz, 1H), 5.54-5.31 (m, 2H), 4.60 (td, J=14.4, 3.8 Hz, 2H), 4.43-4.28 (m, 1H), 4.16-4.04 (m, 1H), 2.98-2.79 (m, 2H), 2.18-2.00 (m, 1H).

Example 31: 5-(1-((benzyloxy)methyl)-1H-pyrazol-4-yl)-3-((2R,4S)-2-(2,5-difluorophenyl)-4-fluoropyrrolidin-1-yl)-1H-pyrazolo[3,4-b]pyridine

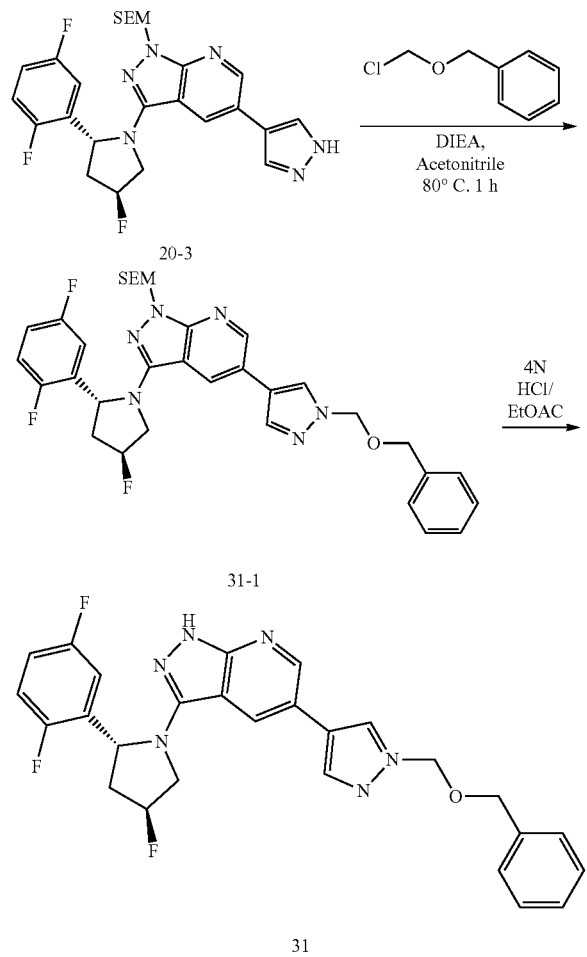

31

5-(1-((Benzyloxy)methyl)-1H-pyrazol-4-yl)-3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine

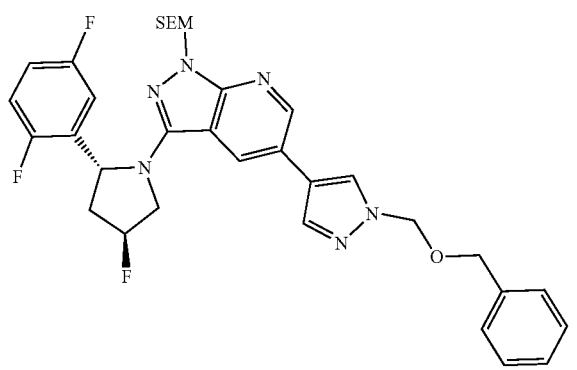 [SMILES: C[Si](C)(C)CCOCn1nc(N2C[C@@H](F)C[C@@H]2c2cc(F)ccc2F)c2cc(-c3cnn(COCc4ccccc4)c3)cnc21]

To a screw-capped vial was added 3-((2R,4S)-2-(2,5-difluorophenyl)-4-fluoropyrrolidin-1-yl)-5-(1H-pyrazol-4-yl)-1-((2-(trimethylsilyl)ethoxy)methyl)-1H-pyrazolo[3,4-b]pyridine (100 mg, 0.194 mmol), ((chloromethoxy)methyl)benzene (60 mg, 0.389 mmol), DIEA (124 mg, 0.97 mmol) and acetonitrile (5 mL). The mixture was stirred at 80° C. for 1 h. Water (50 mL) was added and the mixture was extracted with EA (50 mL*2). The combined organic layer was dried over Na₂SO₄ and filtered. The filtrate was concentrated and purified by column chromatography (petrolumen ether/EtOAc=3/1) to give 5-(1-((benzyloxy)methyl)-1H-pyrazol-4-yl)-3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine (100 mg, 81.2%) as yellow oil.

MS (ESI): m/z=635 [M+H]⁺.

5-(1-((Benzyloxy)methyl)-1H-pyrazol-4-yl)-3-((2R,4S)-2-(2,5-difluorophenyl)-4-fluoropyrrolidin-1-yl)-1H-pyrazolo[3,4-b]pyridine

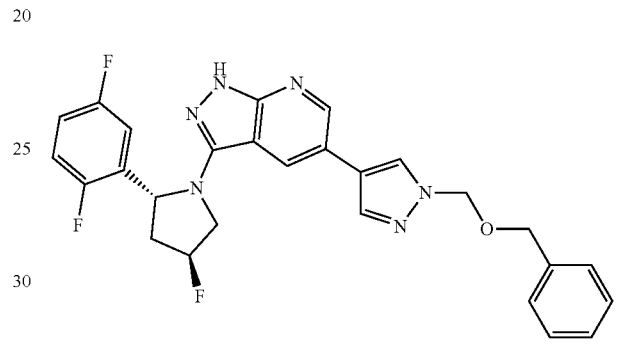

5-(1-((Benzyloxy)methyl)-1H-pyrazol-4-yl)-3-((2R,4S)-2-(2,5-difluorophenyl)-4-fluoropyrrolidin-1-yl)-1H-pyrazolo[3,4-b]pyridine was prepared using a method similar to that example 20 by replacing the corresponding starting material.

MS (ESI): m/z=505 [M+H]⁺.

¹H NMR (400 MHz, CD₃OD) δ 8.58 (d, J=1.9 Hz, 1H), 8.15 (d, J=2.1 Hz, 2H), 7.90 (s, 1H), 7.33-7.21 (m, 5H), 7.13-7.03 (m, 2H), 6.95-6.88 (m, 1H), 5.56 (s, 2H), 5.54-5.32 (m, 2H), 4.56 (s, 2H), 4.44-4.28 (m, 1H), 4.11 (dd, J=24.7, 11.8 Hz, 1H), 2.92-2.78 (m, 1H), 2.19-2.00 (m, 1H).

Example 32

1-(4-(3-((2R,4S)-2-(2,5-difluorophenyl)-4-fluoropyrrolidin-1-yl)-1H-pyrazolo[3,4-b]pyridin-5-yl)-1H-pyrazol-1-yl)-2-methylpropan-2-ol

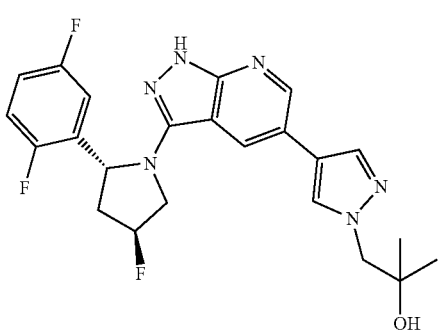 [SMILES: CC(C)(O)Cn1cc(-c2cnc3[nH]nc(N4C[C@@H](F)C[C@@H]4c4cc(F)ccc4F)c3c2)cn1]

1-(4-(3-((2R,4S)-2-(2,5-Difluorophenyl)-4-fluoropyrrolidin-1-yl)-1H-pyrazolo[3,4-b]pyridin-5-yl)-1H-pyrazol-1-yl)-2-methylpropan-2-ol was prepared using a method similar to that example 20 by replacing the corresponding starting material.

MS (ESI): m/z=457 [M+H]⁺.

¹H NMR (400 MHz, CD₃OD) δ 8.58 (d, J=2.0 Hz, 1H), 8.11 (d, J=2.0 Hz, 1H), 7.98 (d, J=0.6 Hz, 1H), 7.80 (d, J=0.7 Hz, 1H), 7.16-7.01 (m, 2H), 6.96-6.90 (m, 1H), 5.57-5.35 (m, 2H), 4.41-4.28 (m, 1H), 4.16-4.05 (m, 3H), 2.93-2.79 (m, 1H), 2.19-1.99 (m, 1H), 1.19 (d, J=1.6 Hz, 6H).

Example 33: 2-(4-(3-((2R,4S)-2-(2,5-difluorophenyl)-4-fluoropyrrolidin-1-yl)-1H-pyrazolo[3,4-b]pyridin-5-yl)-1H-pyrazol-1-yl)-N,N-dimethylethan-1-amine

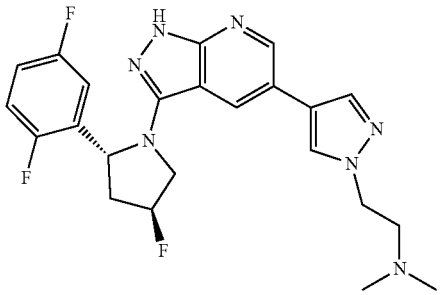 [SMILES: CN(C)CCn1cc(-c2cnc3[nH]nc(N4C[C@@H](F)C[C@@H]4c4cc(F)ccc4F)c3c2)cn1]

2-(4-(3-((2R,4S)-2-(2,5-Difluorophenyl)-4-fluoropyrrolidin-1-yl)-1H-pyrazolo[3,4-b]pyridin-5-yl)-1H-pyrazol-1-yl)-N,N-dimethylethan-1-amine was prepared using a method similar to that example 20 by replacing the corresponding starting material.

MS (ESI): m/z=456 [M+H]⁺.

¹H NMR (400 MHz, CD₃OD) δ 8.57 (d, J=2.0 Hz, 1H), 8.13 (d, J=2.0 Hz, 1H), 8.03 (d, J=0.7 Hz, 1H), 7.80 (d, J=0.8 Hz, 1H), 7.15-7.03 (m, 2H), 6.96-6.89 (m, 1H), 5.55-5.34 (m, 2H), 4.43-4.26 (m, 3H), 4.15-4.05 (m, 1H), 2.93-2.79 (m, 3H), 2.30 (s, 6H), 2.19-2.01 (m, 1H).

Example 34

5-(1-(azetidin-3-ylmethyl)-1H-pyrazol-4-yl)-3-((2R,4S)-2-(2,5-difluorophenyl)-4-fluoropyrrolidin-1-yl)-1H-pyrazolo[3,4-b]pyridine

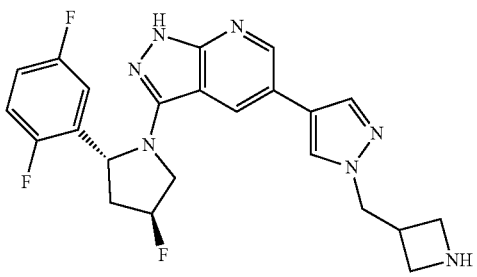 [SMILES: Fc1ccc(F)c([C@H]2C[C@H](F)CN2c2n[nH]c3ncc(-c4cnn(CC5CNC5)c4)cc23)c1]

5-(1-(azetidin-3-ylmethyl)-1H-pyrazol-4-yl)-3-((2R,4S)-2-(2,5-difluorophenyl)-4-fluoropyrrolidin-1-yl)-1H-pyrazolo[3,4-b]pyridine was prepared using a method similar to that example 20 by replacing the corresponding starting material.

MS (ESI): m/z=454 [M+H]⁺.

¹H NMR (400 MHz, DMSO-d₆) δ 12.15 (s, 1H), 8.62 (d, J=2.0 Hz, 1H), 8.20-8.11 (m, 2H), 7.86 (s, 1H), 7.25-7.10 (m, 2H), 7.08-7.00 (m, 1H), 5.61-5.36 (m, 2H), 4.52-4.36 (m, 1H), 4.33 (d, J=7.4 Hz, 2H), 4.02 (dd, J=26.1, 11.8 Hz, 1H), 3.56 (t, J=7.6 Hz, 2H), 3.37-3.32 (m, 2H), 3.10-3.04 (m, 1H), 2.80-2.69 (m, 1H), 2.22-2.05 (m, 1H).

Example 35

3-((2R,4S)-2-(2,5-difluorophenyl)-4-fluoropyrrolidin-1-yl)-5-(1-(2,2,2-trifluoroethyl)-1H-pyrazol-4-yl)-1H-pyrazolo[3,4-b]pyridine

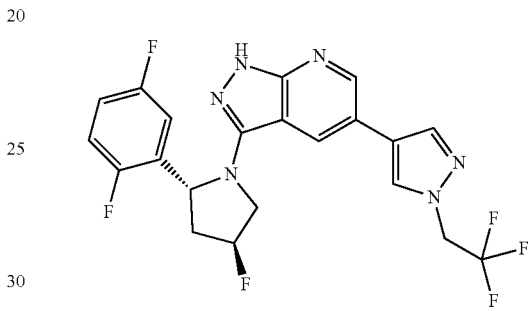

3-((2R,4S)-2-(2,5-Difluorophenyl)-4-fluoropyrrolidin-1-yl)-5-(1-(2,2,2-trifluoroethyl)-1H-pyrazol-4-yl)-1H-pyrazolo[3,4-b]pyridine was prepared using a method similar to that example 20 by replacing the corresponding starting material.

MS (ESI): m/z=467 [M+H]⁺.

¹H NMR (400 MHz, DMSO-d₆) δ 12.30 (s, 1H), 8.66 (d, J=2.0 Hz, 1H), 8.33 (s, 1H), 8.28 (d, J=1.9 Hz, 1H), 8.09 (s, 1H), 7.25-7.09 (m, 2H), 7.09-6.98 (m, 1H), 5.58-5.42 (m, 1H), 5.36-5.29 (m, 1H), 5.15 (q, J=9.1 Hz, 2H), 4.52-4.36 (m, 1H), 4.00 (dd, J=26.7, 11.8 Hz, 1H), 2.77-2.61 (m, 1H), 2.18-2.00 (m, 1H).

Example 36

5-(1-(2,2-difluoroethyl)-1H-pyrazol-3-yl)-3-((2R,4S)-2-(2,5-difluorophenyl)-4-fluoropyrrolidin-1-yl)-1H-pyrazolo[3,4-b]pyridine

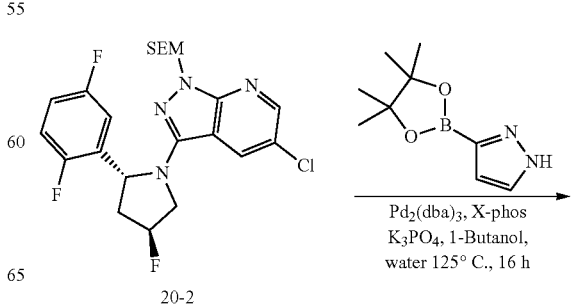

-continued

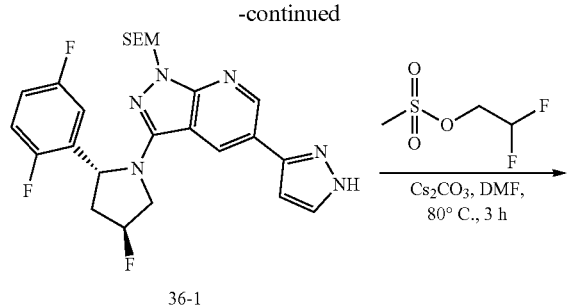

36-1

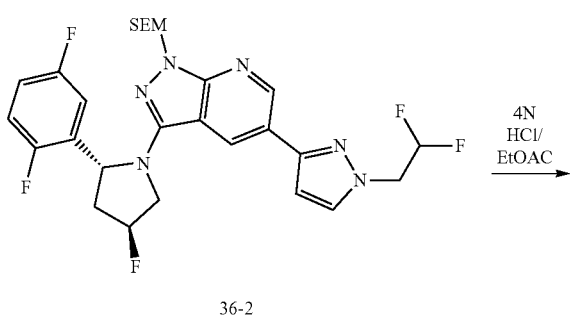

36-2

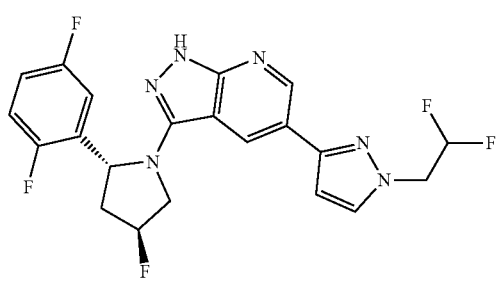

36

3-((2R,4S)-2-(2,5-Difluorophenyl)-4-fluoropyrrolidin-1-yl)-5-(1H-pyrazol-3-yl)-1-((2-(trimethylsilyl)ethoxy)methyl)-1H-pyrazolo[3,4-b]pyridine

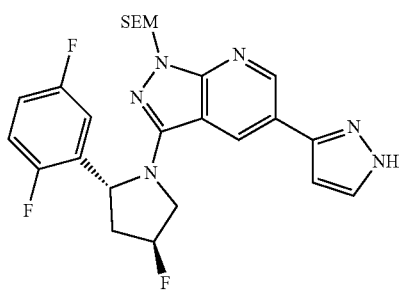 [SMILES: C[Si](C)(C)CCOCn1nc(N2C[C@@H](F)C[C@@H]2c2cc(F)ccc2F)c2cc(-c3cc[nH]n3)cnc21]

3-((2R,4S)-2-(2,5-Difluorophenyl)-4-fluoropyrrolidin-1-yl)-5-(1H-pyrazol-3-yl)-1-((2-(trimethylsilyl)ethoxy)methyl)-1H-pyrazolo[3,4-b]pyridine was prepared using a method similar to that example 20 by replacing the corresponding starting material.

5-(1-(2,2-Difluoroethyl)-1H-pyrazol-3-yl)-3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine

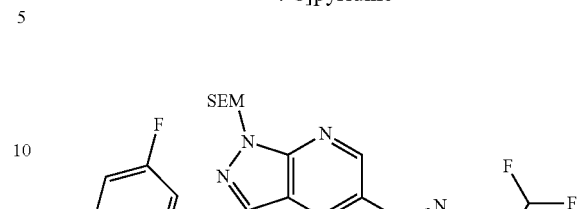

The mixture of 3-((2R,4S)-2-(2,5-difluorophenyl)-4-fluoropyrrolidin-1-yl)-5-(1H-pyrazol-3-yl)-1-((2-(trimethylsilyl)ethoxy)methyl)-1H-pyrazolo[3,4-b]pyridine (30 mg, 0.078 mmol), 2,2-Difluoroethyl mesylate (37 mg, 0.233 mmol), $Cs_2CO_3$ (63 mg, 0.194 mmol) in DMF (1 mL) was stirred at 80° C. for 3 h. The mixture was diluted with water (50 mL), extracteded with EtOAc (50 mL*1), dried over $Na_2SO_4$ and filtered. The filtrate was concentrated and purified by column chromatography (petroluenm ether/EtOAc=1/1) to give 5-(1-(2,2-difluoroethyl)-1H-pyrazol-3-yl)-3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine (40 mg, 88.60%) as yellow oil.

MS (ESI): m/z=601 [M+H]$^+$.

5-(1-(2,2-Difluoroethyl)-1H-pyrazol-3-yl)-3-((2R,4S)-2-(2,5-difluorophenyl)-4-fluoropyrrolidin-1-yl)-1H-pyrazolo[3,4-b]pyridine

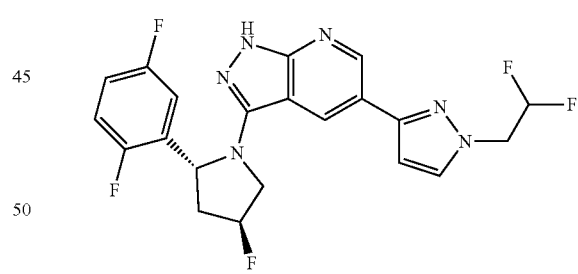

5-(1-(2,2-Difluoroethyl)-1H-pyrazol-3-yl)-3-((2R,4S)-2-(2,5-difluorophenyl)-4-fluoropyrrolidin-1-yl)-1H-pyrazolo[3,4-b]pyridine was prepared using a method similar to that example 20 by replacing the corresponding starting material.

MS (ESI): m/z=450 [M+H]$^+$.

$^1$H NMR (400 MHz, DMSO-d$_6$) δ 12.38 (s, 1H), 8.84 (d, J=1.9 Hz, 1H), 8.38 (d, J=1.8 Hz, 1H), 7.84 (d, J=2.3 Hz, 1H), 7.28-7.11 (m, 2H), 7.11-7.00 (m, 1H), 6.84 (d, J=2.3 Hz, 1H), 6.53-6.27 (m, 1H), 5.57-5.43 (m, 1H), 5.36-5.31 (m, 1H), 4.66 (td, J=15.0, 3.8 Hz, 2H), 4.50-4.35 (m, 1H), 4.04-3.94 (m, 1H), 2.79-2.65 (m, 1H), 2.17-1.98 (m, 1H).

Example 37

2-(3-((2R,4S)-2-(2,5-difluorophenyl)-4-fluoropyrrolidin-1-yl)-1H-pyrazolo[3,4-b]pyridin-5-yl)-5-(methoxymethyl)-1,3,4-oxadiazole

Example 38

2-(3-((2R,4S)-2-(2,5-difluorophenyl)-4-fluoropyrrolidin-1-yl)-1-(methoxymethyl)-1H-pyrazolo[3,4-b]pyridin-5-yl)-5-(methoxymethyl)-1,3,4-oxadiazole

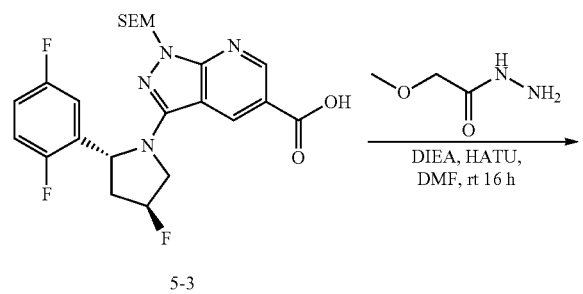

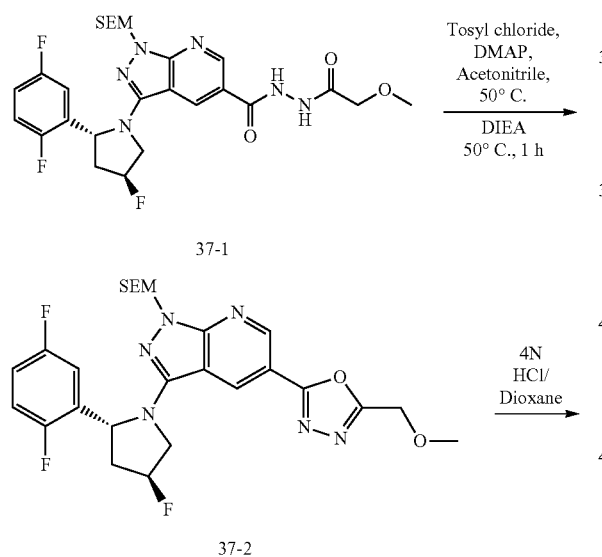

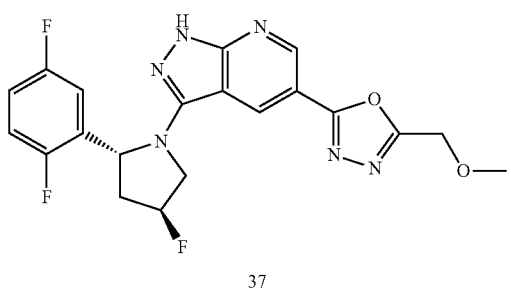

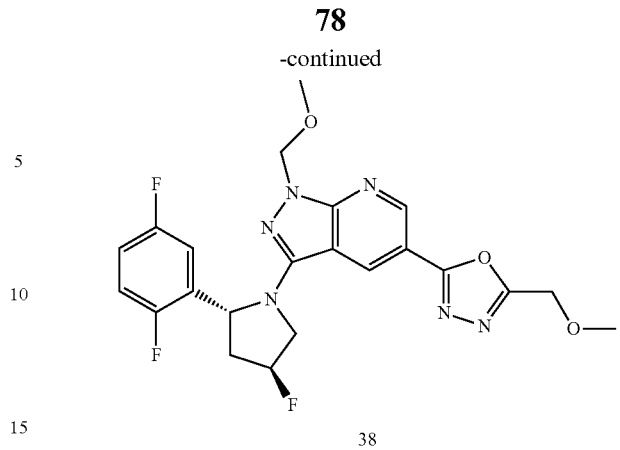

3-((2R,4S)-2-(2,5-Difluorophenyl)-4-fluoropyrrolidin-1-yl)-N'-(2-methoxyacetyl)-1-((2-(trimethylsilyl)ethoxy)methyl)-1H-pyrazolo[3,4-b]pyridine-5-carbohydrazide To the mixture of 3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine-5-carboxylic acid (200 mg, 0.406 mmol), 2-methoxyacetohydrazide (126 mg, 1.218 mmol), DIEA (262 mg, 2.06 mmol) in DMF (8 mL) was added HATU (308 mg, 0.812 mmol) and then stirred at r.t. for 16 h. The mixture was diluted with water (50 mL), extracted with DCM (50 mL), dried over $Na_2SO_4$ and filtered. The filtrate was concentrated and purified by column chromatography (DCM/methanol=20/1) to give 3-((2R,4S)-2-(2,5-difluorophenyl)-4-fluoropyrrolidin-1-yl)-N'-(2-methoxyacetyl)-1-((2-(trimethylsilyl)ethoxy)methyl)-1H-pyrazolo[3,4-b]pyridin e-5-carbohydrazide (230 mg, 97.9%) as a yellow solid.

MS (ESI): m/z=601 [M+Na]$^+$.

2-(3-((2R,4S)-2-(2,5-Difluorophenyl)-4-fluoropyrrolidin-1-yl)-1-((2-(trimethylsilyl)ethoxy)methyl)-1H-pyrazolo[3,4-b]pyridin-5-yl)-5-(methoxymethyl)-1,3,4-oxadiazole 2-(3-((2R,4S)-2-(2,5-Difluorophenyl)-4-fluoropyrrolidin-1-yl)-1-(methoxymethyl)-1H-pyrazolo[3,4-b]pyridin-5-yl)-5-(methoxymethyl)-1,3,4-oxadiazole

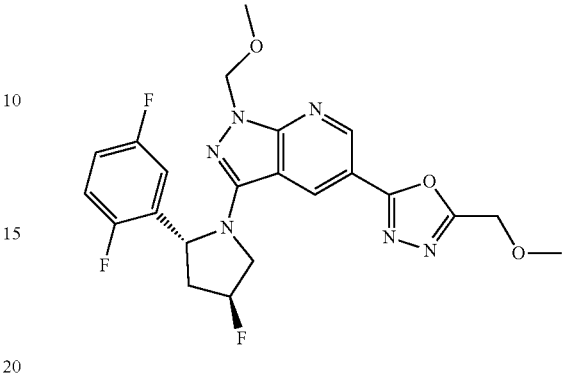

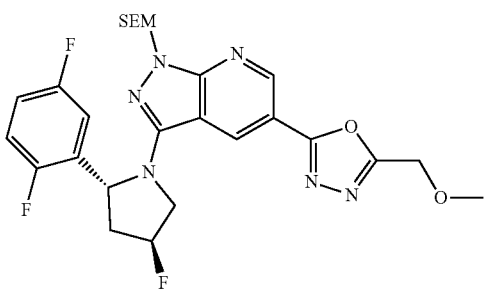 [SMILES: COCc1nnc(-c2cnc3c(c2)c(N2C[C@@H](F)C[C@@H]2c2cc(F)ccc2F)nn3COCC[Si](C)(C)C)o1]

The mixture of 2-(3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridin-5-yl)-5-(methoxymethyl)-1,3,4-oxadiazole (100 mg, 0.178 mmol) in EtOAc (4 mL) was added 4N HCl in dioxane (4 mL) drop wised at 0° C. and stirred for 2 h. The mixture was concentrated at 0° C., diluted with methanol (5 mL), basified by 7N NH₃ in methanol, concentrated and purified by prep-HPLC to give 2-(3-((2R,4S)-2-(2,5-difluorophenyl)-4-fluoropyrrolidin-1-yl)-1H-pyrazolo[3,4-b]pyridin-5-yl)-5-(methoxymethyl)-1,3,4-oxadiazole (14 mg, 18.3%) as a yellow solid MS (ESI): m/z=432 [M+H]$^+$.

$^1$H NMR (400 MHz, DMSO-d₆) δ 8.95 (d, J=2.0 Hz, 1H), 8.61 (d, J=2.0 Hz, 1H), 7.28-7.15 (m, 2H), 7.09-7.03 (m, 1H), 6.03 (s, 1H), 5.51 (d, J=53.2 Hz, 1H), 5.36-5.32 (m, 1H), 4.72 (s, 2H), 4.54-4.39 (m, 1H), 4.09-4.00 (m, 1H), 3.38 (m, 3H), 2.78-2.68 (m, 1H), 2.18-2.01 (m, 1H).

To the mixture of 3-((2R,4S)-2-(2,5-difluorophenyl)-4-fluoropyrrolidin-1-yl)-N'-(2-methoxyacetyl)-1-((2-(trimethylsilyl)ethoxy)methyl)-1H-pyrazolo[3,4-b]pyridine-5-carbohydrazide (230 mg, 0.397 mmol), DMAP (7 mg, 0.060 mmol) in acetonitrile (6 mL) was added tosyl chloride (227 mg, 1.19 mmol) at r.t. The mixture was raised to 50° C. and DIEA (308 mg, 2.382 mmol) was added drop wised and stirred at 50° C. for 1 h. the mixture was diluted with DCM (50 mL), washed with water (50 mL), dried over Na₂SO₄ and filtered. The filtrate was concentrated and purified by column chromatography (petroleumn ether/EtOAc=1/1) to give 2-(3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridin-5-yl)-5-(methoxymethyl)-1,3,4-oxadiazole (150 mg, 67.4%) as a yellow solid.

MS (ESI): m/z=561 [M+H]$^+$.

2-(3-((2R,4S)-2-(2,5-Difluorophenyl)-4-fluoropyrrolidin-1-yl)-1H-pyrazolo[3,4-b]pyridin-5-yl)-5-(methoxymethyl)-1,3,4-oxadiazole 2-(3-((2R,4S)-2-(2,5-Difluorophenyl)-4-fluoropyrrolidin-1-yl)-1-(methoxymethyl)-1H-pyrazolo[3,4-b]pyridin-5-yl)-5-(methoxymethyl)-1,3,4-oxadiazole (17 mg, 20.1%) as a yellow solid.

MS (ESI): m/z=476 [M+H]$^+$.

$^1$H NMR (400 MHz, DMSO-d₆) δ 9.02 (d, J=1.9 Hz, 1H), 8.63 (d, J=2.0 Hz, 1H), 7.25-7.18 (m, 2H), 7.09-7.03 (m, 1H), 5.59-5.46 (m, 2H), 5.41-5.35 (m, 2H), 4.73 (s, 2H), 4.53-4.39 (m, 1H), 4.15-4.06 (m, 1H), 3.38 (s, 3H), 3.06 (s, 3H), 2.83-2.70 (m, 1H), 2.22-2.04 (m, 1H).

Example 39

3-((2R,4S)-2-(2,5-difluorophenyl)-4-fluoropyrrolidin-1-yl)-1H-pyrazolo[3,4-b]pyridine-5-carbohydrazide

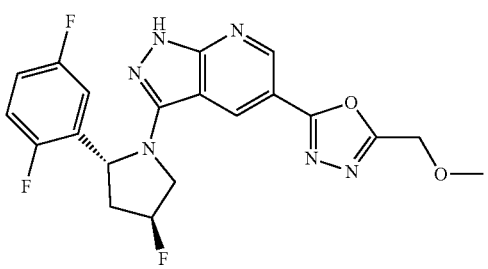 [SMILES: COCc1nnc(-c2cnc3[nH]nc(N4C[C@@H](F)C[C@@H]4c4cc(F)ccc4F)c3c2)o1]

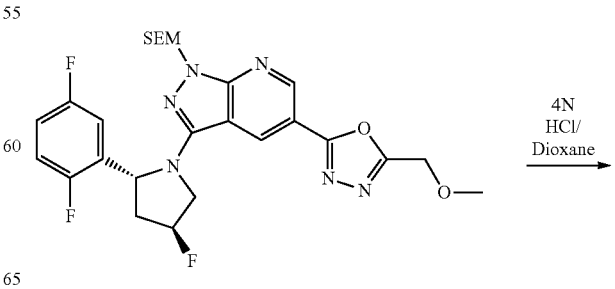

37-2

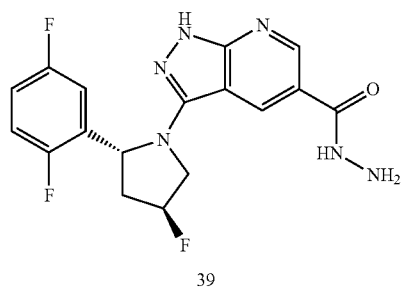

39

3-((2R,4S)-2-(2,5-Difluorophenyl)-4-fluoropyrrolidin-1-yl)-1H-pyrazolo[3,4-b]pyridine-5-carbohydrazide was prepared using a method similar to that example 20 by replacing the corresponding starting material.

MS (ESI): m/z=377 [M+H]$^+$.

$^1$H NMR (400 MHz, DMSO-d$_6$) δ 12.56 (s, 1H), 9.90 (s, 1H), 8.79 (d, J=2.0 Hz, 1H), 8.60 (d, J=1.8 Hz, 1H), 7.23-7.17 (m, 1H), 7.16-7.11 (m, 1H), 7.09 (s, 1H), 7.08-7.04 (m, 1H), 6.96 (s, 1H), 5.52 (d, J=52.5 Hz, 1H), 5.32-5.27 (m, 1H), 4.92 (s, 2H), 4.47-4.35 (m, 1H), 4.07-3.98 (m, 1H), 2.78-2.65 (m, 1H), 2.20-2.02 (m, 1H).

Example 40

5-(1-(2,2-difluoroethyl)-4-methyl-1H-pyrazol-3-yl)-3-((2R,4S)-2-(2,5-difluorophenyl)-4-fluoropyrrolidin-1-yl)-1H-pyrazolo[3,4-b]pyridine

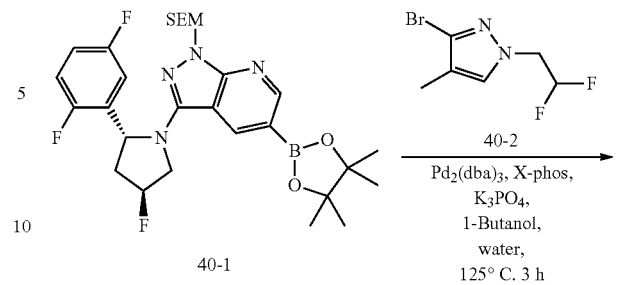

40-1

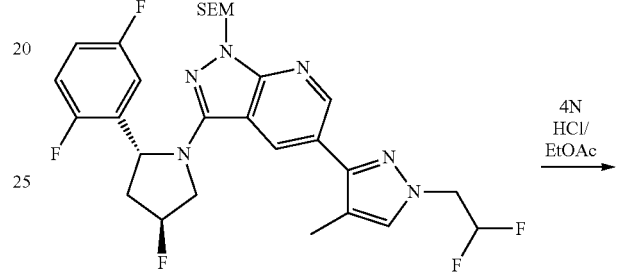

40-3

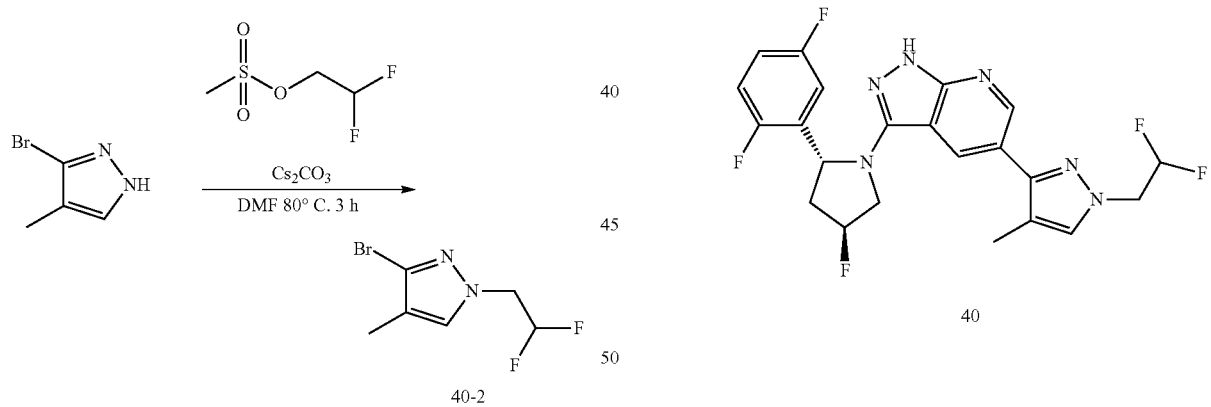

40

3-bromo-1-(2,2-difluoroethyl)-4-methyl-1H-pyrazole

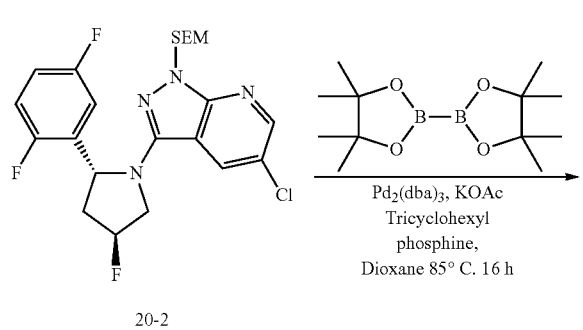

3-Bromo-1-(2,2-difluoroethyl)-4-methyl-1H-pyrazole was prepared using a method similar to that example 36 by replacing the corresponding starting material.

MS (ESI): m/z=227 [M+H]$^+$.

3-((2R,4S)-2-(2,5-Difluorophenyl)-4-fluoropyrrolidin-1-yl)-5-(4,4,5,5-tetramethyl-1,3,2-dioxaborolan-2-yl)-1-((2-(trimethylsilyl)ethoxy)methyl)-1H-pyrazolo[3,4-b]pyridine

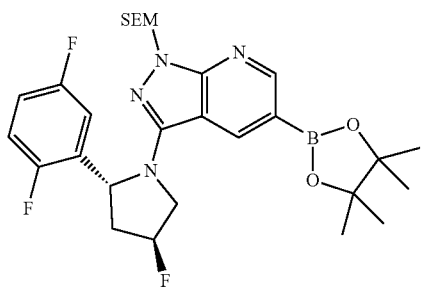 [SMILES: CC1(C)OB(c2cnc3c(c2)c(N2C[C@@H](F)C[C@@H]2c2cc(F)ccc2F)nn3COCC[Si](C)(C)C)OC1(C)C]

A mixture of 5-chloro-3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine (200 mg, 0.414 mmol), 4,4,4',4',5,5,5',5'-octamethyl-2,2'-bi(1,3,2-dioxaborolane) (315 mg, 1.24 mmol), KOAc (122 mg, 1.242 mmol), Pd$_2$(dba)$_3$ (38 mg, 0.0414 mmol) and tricyclohexyl phosphine (23 mg, 0.828 mmol) in dioxane (8 mL) was stirred at 85° C. for 16 h under Ar$_2$ atmosphere. The mixture was used to the next step directly.

MS (ESI): m/z=575 [M+H]$^+$.

5-(1-(2,2-Difluoroethyl)-4-methyl-1H-pyrazol-3-yl)-3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine

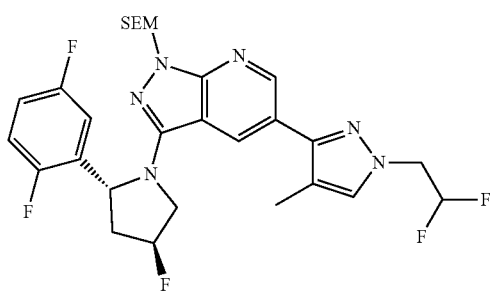 [SMILES: Cc1cn(CC(F)F)nc1-c1cnc2c(c1)c(N1C[C@@H](F)C[C@@H]1c1cc(F)ccc1F)nn2COCC[Si](C)(C)C]

5-(1-(2,2-Difluoroethyl)-4-methyl-1H-pyrazol-3-yl)-3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine was prepared using a method similar to that example 20 by replacing the corresponding starting material.

MS (ESI): m/z=593 [M+H]$^+$.

5-(1-(2,2-Difluoroethyl)-4-methyl-1H-pyrazol-3-yl)-3-((2R,4S)-2-(2,5-difluorophenyl)-4-fluoropyrrolidin-1-yl)-1H-pyrazolo[3,4-b]pyridine

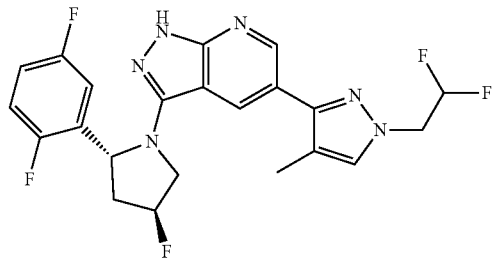 [SMILES: Cc1cn(CC(F)F)nc1-c1cnc2[nH]nc(N3C[C@@H](F)C[C@@H]3c3cc(F)ccc3F)c2c1]

5-(1-(2,2-Difluoroethyl)-4-methyl-1H-pyrazol-3-yl)-3-((2R,4S)-2-(2,5-difluorophenyl)-4-fluoropyrrolidin-1-yl)-1H-pyrazolo[3,4-b]pyridine was prepared using a method similar to that example 20 by replacing the corresponding starting material.

MS (ESI): m/z=464 [M+H]$^+$.

$^1$H NMR (400 MHz, DMSO-d$_6$) δ 12.42 (s, 1H), 8.64 (d, J=2.0 Hz, 1H), 8.17 (d, J=1.9 Hz, 1H), 7.64 (s, 1H), 7.26-7.11 (m, 2H), 7.07-7.03 (m, 1H), 6.50-6.20 (m, 1H), 6.00 (s, 1H), 5.41-5.32 (m, 2H), 4.58 (td, J=15.0, 3.6 Hz, 2H), 4.44-4.32 (m, 1H), 4.06-3.95 (m, 1H), 2.80-2.66 (m, 1H), 2.11 (s, 3H), 2.08-1.95 (m, 1H).

Example 41

2-(3-((2R,4S)-2-(2,5-difluorophenyl)-4-fluoropyrrolidin-1-yl)-1H-pyrazolo[3,4-b]pyridin-5-yl)-5-((trifluoromethoxy)methyl)-1,3,4-oxadiazole

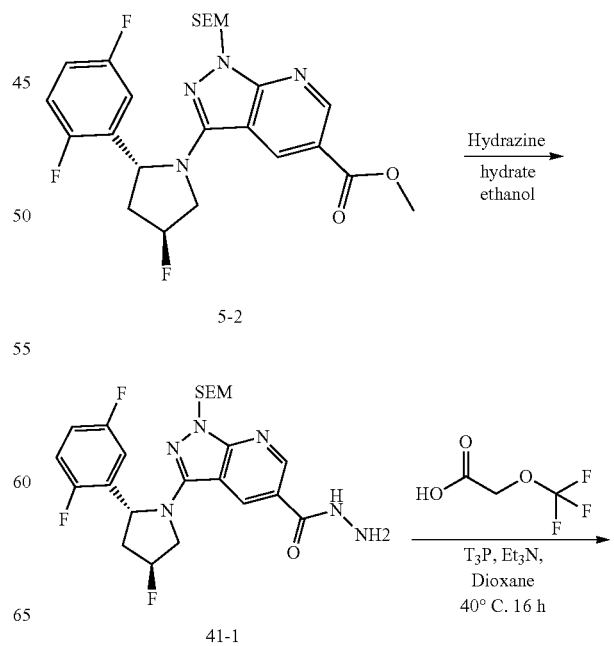

-continued

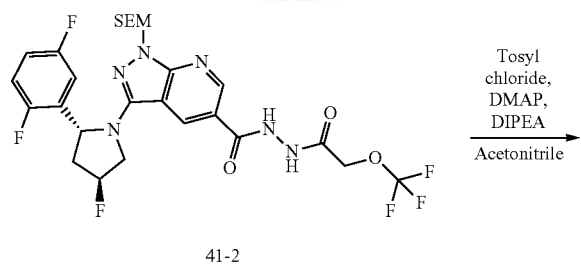

41-2

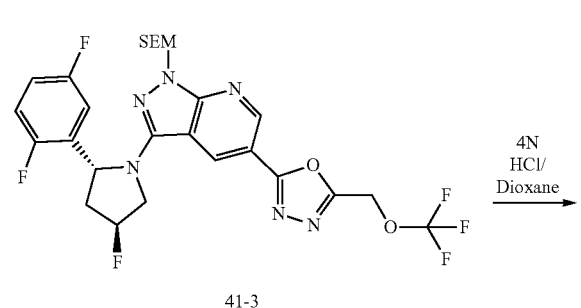

41-3

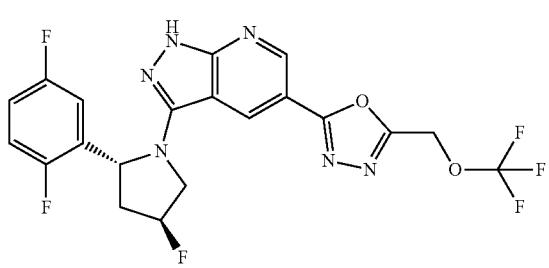

41

3-((2R,4S)-2-(2,5-Difluorophenyl)-4-fluoropyrrolidin-1-yl)-1-((2-(trimethylsilyl)ethoxy)methyl)-1H-pyrazolo[3,4-b]pyridine-5-carbohydrazide

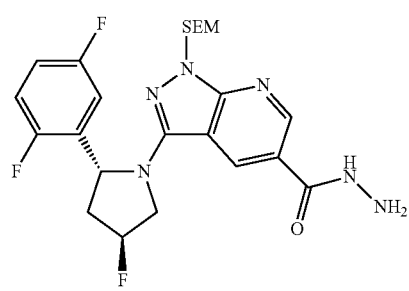 [SMILES: C[Si](C)(C)CCOCn1nc(N2C[C@@H](F)C[C@@H]2c2cc(F)ccc2F)c2cc(C(=O)NN)cnc21]

3-((2R,4S)-2-(2,5-Difluorophenyl)-4-fluoropyrrolidin-1-yl)-1-((2-(trimethylsilyl)ethoxy)methyl)-1H-pyrazolo[3,4-b]pyridine-5-carbohydrazide was prepared using a method similar to that example 4 by replacing the corresponding starting material.

MS (ESI): m/z=507 [M+H]$^+$.

3-((2R,4S)-2-(2,5-Difluorophenyl)-4-fluoropyrrolidin-1-yl)-N'-(2-(trifluoromethoxy)acetyl)-1-((2-(trimethylsilyl)ethoxy)methyl)-1H-pyrazolo[3,4-b]pyridine-5-carbohydrazide To the mixture of 3-((2R,4S)-2-(2,5-difluorophenyl)-4-fluoropyrrolidin-1-yl)-1-((2-(trimethylsilyl)ethoxy)methyl)-1H-pyrazolo[3,4-b]pyridine-5-carbohydrazide (382 mg, 0.75 mmol), 2-(trifluoromethoxy)acetic acid (162 mg, 1.13 mmol), Et$_3$N (380 mg, 3.75 mmol) in dioxane (10 ml) was added 50% T3P in EtOAc (2.3 mL, 1.13 mmol) and stirred at 40° C. for 16 h. It was diluted with DCM (50 mL), washed with water (50 mL*2), dried over Na$_2$SO$_4$ and filtered. The filtrate was concentrated and purified by column chromatography (petroluenm ether/EtOAc=1/1) to give 3-((2R,4S)-2-(2,5-difluorophenyl)-4-fluoropyrrolidin-1-yl)-N'-(2-(trifluoromethoxy)acetyl)-1-((2-(trimethylsilyl)ethoxy)methyl)-1H-pyrazolo[3,4-b]pyridine-5-carbohydrazide (377 mg, yield 79.5%) as a yellow solid.

MS (ESI): m/z=533 [M–SEM+CH$_2$OH]$^+$.

2-(3-((2R,4S)-2-(2,5-difluorophenyl)-4-fluoropyrrolidin-1l-yl)-1-((2-(trimethylsilyl)ethoxy)methyl)-1H-pyrazolo[3,4-b]pyridin-5-yl)-5-((trifluoromethoxy)methyl)-1,3,4-oxadiazole 2-(3-((2R,4S)-2-(2,5-difluorophenyl)-4-fluoropyrrolidin-1l-yl)-1-((2-(trimethylsilyl)ethoxy)methyl)-1H-pyrazolo[3,4-b]pyridin-5-yl)-5-((trifluoromethoxy)methyl)-1,3,4-oxadiazole was prepared using a method similar to that example 37 by replacing the corresponding starting material.

MS (ESI): m/z=615 [M+H]$^+$.

2-(3-((2R,4S)-2-(2,5-Difluorophenyl)-4-fluoropyrrolidin-1l-yl)-1H-pyrazolo[3,4-b]pyridin-5-yl)-5-((trifluoromethoxy)methyl)-1,3,4-oxadiazole

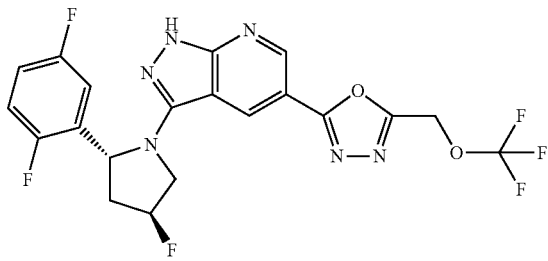 [SMILES: Fc1ccc(F)c([C@H]2C[C@H](F)CN2c2n[nH]c3ncc(-c4nnc(COC(F)(F)F)o4)cc23)c1]

2-(3-((2R,4S)-2-(2,5-difluorophenyl)-4-fluoropyrrolidin-1l-yl)-1H-pyrazolo[3,4-b]pyridin-5-yl)-5-((trifluoromethoxy)methyl)-1,3,4-oxadiazole was prepared using a method similar to that example 37 by replacing the corresponding starting material.

MS (ESI): m/z=486 [M+H]+.

$^1$H NMR (400 MHz, DMSO-d$_6$) δ 12.88 (s, 1H), 8.95 (d, J=2.0 Hz, 1H), 8.61 (d, J=2.0 Hz, 1H), 7.24-7.17 (m, 2H), 7.08-7.04 (m, 1H), 5.58-5.44 (m, 3H), 5.41-5.30 (m, 1H), 4.46 (dd, J=39.4, 11.7 Hz, 1H), 4.05 (dd, J=25.3, 12.2 Hz, 1H), 2.81-2.67 (m, 1H), 2.17-2.02 (m, 1H).

Example 42

2-(3-((2R,4S)-2-(2,5-difluorophenyl)-4-fluoropyrrolidin-1-yl)-1H-pyrazolo[3,4-b]pyridin-5-yl)-5-(isopropoxymethyl)-1,3,4-oxadiazole

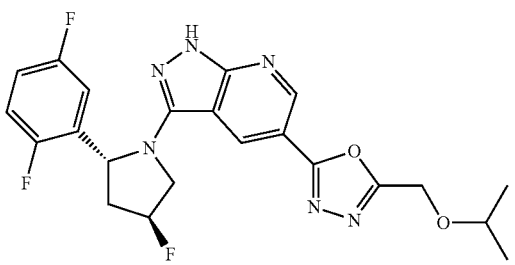 [SMILES: CC(C)OCc1nnc(-c2cnc3[nH]nc(N4C[C@@H](F)C[C@@H]4c4cc(F)ccc4F)c3c2)o1]

2-(3-((2R,4S)-2-(2,5-difluorophenyl)-4-fluoropyrrolidin-1l-yl)-1H-pyrazolo[3,4-b]pyridin-5-yl)-5-(isopropoxymethyl)-1,3,4-oxadiazole was prepared using a method similar to that example 41 by replacing the corresponding starting material.

MS (ESI): m/z=460 [M+H]+.

1H NMR (400 MHz, DMSO-d$_6$) δ 12.83 (s, 1H), 8.93 (d, J=1.9 Hz, 1H), 8.59 (d, J=1.9 Hz, 1H), 7.28-7.14 (m, 2H), 7.12-6.99 (m, 1H), 5.51 (d, J=52.7 Hz, 1H), 5.36-5.32 (m, 1H), 4.74 (s, 2H), 4.53-4.39 (m, 1H), 4.04 (dd, J=24.9, 12.1 Hz, 1H), 3.80-3.74 (m, 1H), 2.80-2.68 (m, 1H), 2.18-2.01 (m, 1H), 1.16 (t, J=11.6 Hz, 6H).

Example 43

((2R,4S)-2-(2,5-difluorophenyl)-4-fluoropyrrolidin-1-yl)(4-(((1R,2R)-2-hydroxycyclopentyl)amino)-1H-pyrazolo[3,4-b]pyridin-3-yl)methanone

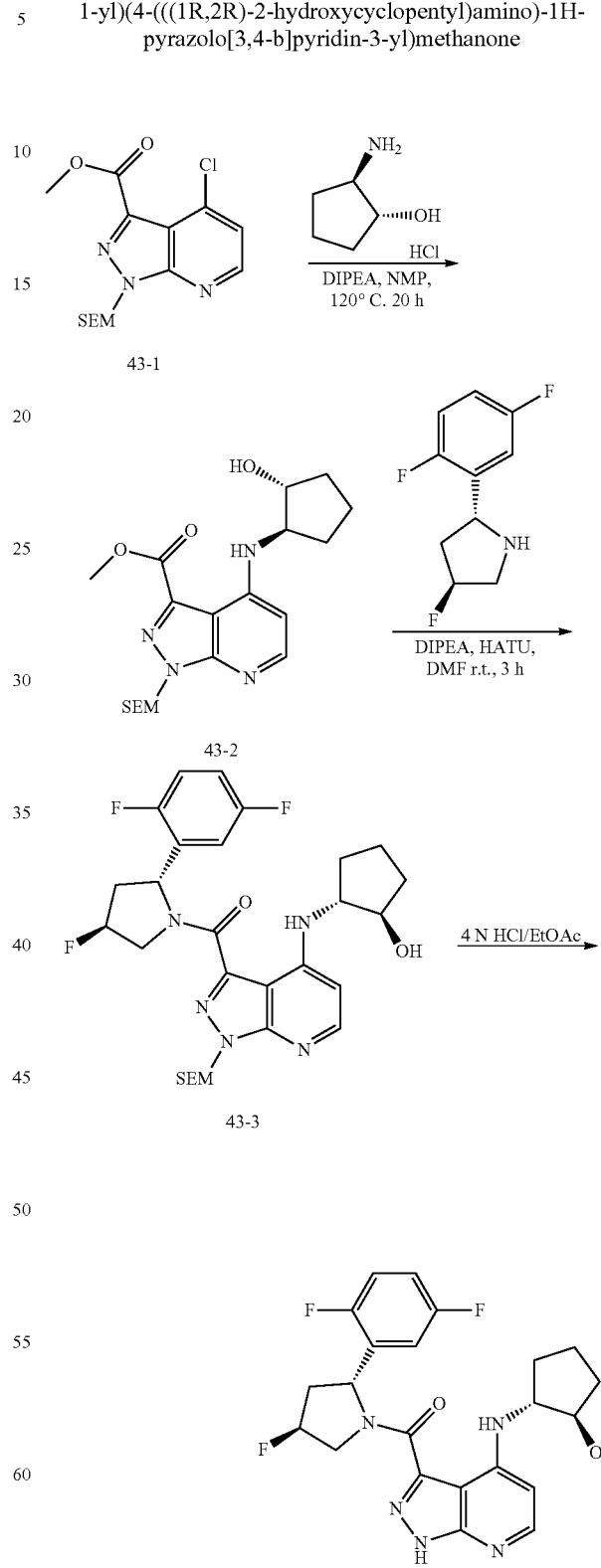

4-(((1R,2R)-2-Hydroxycyclopentyl)amino)-1-((2-(trimethylsilyl)ethoxy)methyl)-1H-pyrazolo[3,4-b]pyridine-3-carboxylic acid

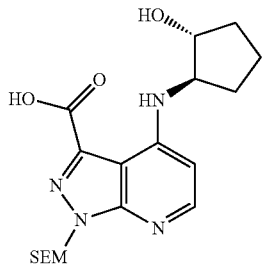 [SMILES: C[Si](C)(C)CCOCn1nc(C(=O)O)c2c(N[C@@H]3CCC[C@H]3O)ccnc21]

The mixture of methyl 4-chloro-1-((2-(trimethylsilyl)ethoxy)methyl)-1H-pyrazolo[3,4-b]pyridine-3-carboxylate (300 mg, 0.88 mmol), (1R,2R)-2-aminocyclopentan-1-ol hydrochloride (121 mg, 0.88 mmol), DIEA (341 mg, 2.64 mmol) in NMP (8 mL) was stirred at 120° C. in sealed tube for 20 h. The mixture was concentrated and purified by reverse phase column chromatography to give 4-(((1R,2R)-2-hydroxycyclopentyl)amino)-1-((2-(trimethylsilyl)ethoxy)methyl)-1H-pyrazolo[3,4-b]pyridine-3-carboxylic acid (240 mg, 69.5%) as a yellow solid.

MS (ESI): m/z=393 [M+H]$^+$.

((2R,4S)-2-(2,5-difluorophenyl)-4-fluoropyrrolidin-1-yl)(4-(((1R,2R)-2-hydroxycyclopentyl)amino)-1-((2-(trimethylsilyl)ethoxy)methyl)-1H-pyrazolo[3,4-b]pyridin-3-yl)methanone

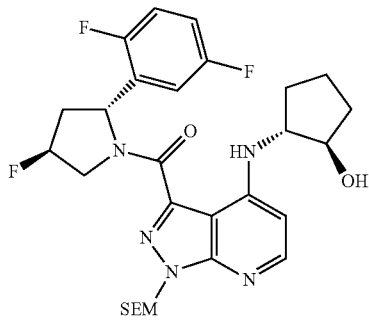 [SMILES: C[Si](C)(C)CCOCn1nc(C(=O)N2C[C@@H](F)C[C@@H]2c2cc(F)ccc2F)c2c(N[C@@H]3CCC[C@H]3O)ccnc21]

A mixture of 4-(((1R,2R)-2-hydroxycyclopentyl)amino)-1-((2-(trimethylsilyl)ethoxy)methyl)-1H-pyrazolo[3,4-b]pyridine-3-carboxylic acid (240 mg, 0.61 mmol), (2R,4S)-2-(2,5-difluorophenyl)-4-fluoropyrrolidine (368 mg, 1.83 mmol), DIEA (394 mg, 3.05 mmol) and HATU (464 mg, 1.22 mmol) in DMF (8 mL) was stirred at r.t. for 3 h. The mixture was diluted with DCM (50 mL), washed with water (50 mL). The organic phase was dried and filtered. The filtrate was concentrated and purified by column chromatography (petroleum ether/EtOAc=1/1) to give ((2R,4S)-2-(2,5-difluorophenyl)-4-fluoropyrrolidin-1-yl)(4-(((1R,2R)-2-hydroxycyclopentyl)amino)-1-((2-(trimethylsilyl)ethoxy)methyl)-1H-pyrazolo[3,4-b]pyridin-3-yl)methanone (332 mg, yield 94.5%) as yellow solid.

MS (ESI): m/z=572 [M+H]$^+$.

((2R,4S)-2-(2,5-Difluorophenyl)-4-fluoropyrrolidin-1-yl)(4-(((1R,2R)-2-hydroxycyclopentyl)-amino)-1H-pyrazolo[3,4-b]pyridin-3-yl)methanone

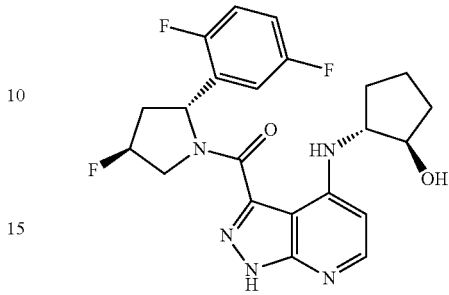

((2R,4S)-2-(2,5-Difluorophenyl)-4-fluoropyrrolidin-1-yl)(4-(((1R,2R)-2-hydroxycyclopentyl)amino)-1H-pyrazolo[3,4-b]pyridin-3-yl)methanone was prepared using a method similar to that example 41 by replacing the corresponding starting material.

MS (ESI): m/z=447 [M+H]$^+$.

$^1$H NMR (400 MHz, CD$_3$OD) δ 8.00-7.89 (m, 1H), 7.15-6.69 (m, 3H), 6.38-6.20 (m, 1H), 5.61-5.28 (m, 2H), 4.83-4.73 (m, 1H), 4.43-4.29 (m, 1H), 4.12-3.94 (m, 1H), 3.75-3.68 (m, 1H), 2.88-2.71 (m, 1H), 2.35-1.44 (m, 7H).

Biological Test Example 1 In Vitro Activity Test on TRKA, TRKB, TRKC Kinase

Experimental Materials

Recombinant human TRKA, TRKB, TRKC proteins were purchased from Carna Biosciences. HTRF kinEASE TK kit was purchased from Cisbio Bioassays. Synergy Neo 2 of Biotek was used to read the plate.

Experimental Method

The tested compounds were subjected to 3-fold serial dilution to reach a final concentration of 1 μM to 0.05 nM (10 concentrations), duplicates for each concentration; and the DMSO concentration in the detection reaction was 1%.

TRKA Enzyme Reaction:

0.2 ng/μL TRKA protein kinase, 1 μM TK Substrate-biotin polypeptide substrate, 14.68 μM ATP, 1×enzymatic buffer, 5 mM MgCl$_2$, and 1 mM DTT. The assay plate was White Proxiplate384-Plus plate (PerkinElmer), and the reaction was incubated at room temperature for 40 min, and the assay volume was 10 μL.

TRKB Enzyme Reaction:

0.037 ng/μL TRKB protein kinase, 1 μM TK Substrate-biotin polypeptide substrate, 4.77 μM ATP, 1× enzymatic buffer, 5 mM MgCl$_2$, 1 mM MnCl$_2$ and 1 mM DTT. The assay plate was White Proxiplate 384-Plus plate (PerkinElmer), the reaction was incubated at room temperature for 50 min, and the assay volume was 10 μL.

TRKC Enzyme Reaction:

0.037 ng/μL TRKC protein kinase, 1 μM TK Substrate-biotin polypeptide substrate, 25.64 μM ATP, 1× enzymatic buffer, 5 mM MgCl$_2$, and 1 mM DTT. The detection plate was White Proxiplate 384-Plus plate (PerkinElmer), the reaction was incubated at room temperature for 40 min, and the assay volume was 10 μL.

Detection Steps:

10 μL of detection reagent (containing 0.125 μM SA-XL665 and 5 μL 1×TK-Antibody) was added to the plate and incubated overnight at room temperature. Synergy Neo 2 was used to read the plate.

Data Analysis

The 665/620 Ratio was converted according to the following formula into inhibition rate (%)=(1−Ratio$_{test}$/Ratio$_{max}$)×100%. Ratio$_{max}$ was the value of positive controls without tested compound, and Ratio$_{test}$ was the value of each concentration of different compounds. IC50 (nM) data was obtained by 4 parameter curve fitting (see Table 1).

TABLE 1

| Compound | TRKA(nM) | TRKB(nM) | TRKC(nM) |
| --- | --- | --- | --- |
| Example 1 | <500 | <500 | <500 |
| Example 2 | <500 | <500 | <500 |
| Example 3 | <50 | <100 | <50 |
| Example 4 | <10 | <10 | <10 |
| Example 5 | <10 | <10 | <10 |
| Example 6 | <50 | <50 | <50 |
| Example 7 | <10 | <10 | <10 |
| Example 8 | <50 | <10 | <10 |
| Example 9 | <50 | <10 | <50 |
| Example 10 | <50 | <10 | <10 |
| Example 11 | <10 | <1 | <10 |
| Example 12 | <10 | <50 | <10 |
| Example 13 | <1 | <1 | <1 |
| Example 14 | <10 | <10 | <10 |
| Example 15 | <10 | <10 | <10 |
| Example 16 | <1 | <10 | <10 |
| Example 17 | <1 | <1 | <1 |
| Example 18 | <500 | <500 | <500 |
| Example 19 | <1 | <1 | <1 |
| Example 20 | <1 | <1 | <1 |
| Example 21 | <1 | <1 | <1 |
| Example 22 | <1 | <1 | <1 |
| Example 23 | <10 | <10 | <10 |
| Example 24 | <10 | <500 | <100 |
| Example 25 | <1 | <1 | <1 |
| Example 26 | <1 | <1 | <1 |
| Example 27 | <1 | <1 | <1 |
| Example 28 | <1 | <1 | <1 |
| Example 29 | <1 | <1 | <1 |
| Example 30 | <1 | <1 | <1 |
| Example 31 | <10 | <1 | <10 |
| Example 32 | <1 | <1 | <1 |
| Example 33 | <1 | <1 | <1 |
| Example 34 | <1 | <1 | <1 |
| Example 35 | <1 | <1 | <1 |
| Example 36 | <1 | <1 | <1 |
| Example 37 | <1 | <1 | <1 |
| Example 38 | <100 | <10 | <100 |
| Example 39 | <1 | <1 | <1 |
| Example 40 | <1 | <1 | <1 |
| Example 41 | <1 | <1 | <1 |
| Example 42 | <1 | <1 | <1 |
| Example 43 | <1 | <1 | <1 |

Biological Test Example 2: Detection of TRK Kinase Activity on Cellular Level by ELISA NIH-3T3 cell line stably expressing TRKA or TRKB or TRKC was constructed by plasmid transfection.

On the first day, cells were seeded into a 96-well cell culture plate, 10000 cells/well in the medium (DMEM+10% FBS). On the second day, changed to 0.5% FBS culture medium for starvation overnight. On the third day, different concentrations of the compounds to be tested were added to treat cells for 1 hour, and then stimulated with 100 ng/μl growth factor for 10 min (NGF used to activate TRKA, BDNF used to activate TRKB, NT-3 used to activate TRKC). The cell culture plate was then placed on ice; and the supernatant was removed and washed with pre-cooled PBS once. Diluted the lysis buffer in the kit (Cell Signaling Technology) with distilled water and added protease and phosphatase inhibitor. Added the cell lysis buffer to the wells and placed on ice for 20 min. Cell lysates were pipetted up and down with multiple-channel pipette for several times, and transferred to an antibody pre-coated plate, and sealed the plate to incubate overnight at 4° C. The remaining steps were proceeded according to the method provided in the ELISA kit (e.g., as described in Cell Signaling Technology #7212C).

Biological Test Example 3: KM12-LUC Cell Proliferation Experiment

Human colon cancer cell line KM12-LUC (LUC, stably expressing Luciferase) expressing TPM3-NTRK1 fusion gene was used to evaluate cellular activity of the compounds. The TRK fusion gene in KM12-LUC cells makes the sustained activation of TRK and the downstream signaling pathways associated with cell proliferation such as MAPK-ERK, PI3K-AKT, etc independent of the stimulation of extracellular growth factor. Therefore, inhibition of TRK activity in KM12-LUC cells can significantly inhibit the proliferation of cells. The method was as follows: On the first day, the cells were seeded into 384-well plates at 2000 cells/well; on the second day, different concentrations of test compounds were added; and on the 5$^{th}$ day, CellTiter-Glo (Promega) was added to detect cell viability, and the cell proliferation inhibition rate at 72 hours was calculated. Statistical analysis was carried out by PRISM5 and the IC$_{50}$ of the test compounds was calculated.

The results show that, the compounds of the invention can effectively inhibit proliferation of KM12-LUC cells, as shown in Table 2.

TABLE 2

| Compound | KM12-LUC IC$_{50}$ (nM) |
| --- | --- |
| Example 5 | <10 |
| Example 20 | <10 |
| Example 22 | <10 |
| Example 24 | <10 |
| Example 25 | <10 |
| Example 29 | <10 |
| Example 30 | <10 |
| Example 32 | <1 |
| Example 33 | <1 |
| Example 35 | <10 |
| Example 36 | <10 |
| Example 37 | <10 |

Biological Test Example 4 In Vitro Activity Test on Mutant TRKA (G595R), TRKA (G667C) and TRKC (G623R)

Experimental Materials

The recombinant human TRKA (G595R), TRKA (G667C) and TRKC (G623R) proteins were purchased from SignalChem. HTRF kinEASE TK kit was purchased from Cisbio Bioassays. Synergy Neo 2 of Biotek was used to read the plate.

Experimental Method

The tested compounds were subjected to 4-fold serial dilution to reach a final concentration of 1 μM to 0.004 nM (10 concentrates), duplicates for each concentration; and the final concentration of DMSO in the reaction was 1%.

TRKA (G595R) Enzyme Reaction:

0.12 ng/μL TRKA (G595R) kinase, 1 μM TK Substrate-biotin polypeptide substrate, 4.5 μM ATP, 1× enzymatic buffer, 5 mM MgCl$_2$, and 1 mM DTT. The assay plate was White Proxiplate384-Plus plate (PerkinElmer), and the reaction was incubated at room temperature for 30 min, and the assay volume was 10 μL.

TRKA (G667C) Enzyme Reaction:

0.026 ng/μL TRKA (G667C) kinase, 1 μM TK Substrate-biotin polypeptide substrate, 5.5 μM ATP, 1× enzymatic buffer, 5 mM MgCl$_2$, and 1 mM DTT. The assay plate was White Proxiplate 384-Plus plate (PerkinElmer), the reaction was incubated at room temperature for 30 min, and the assay volume was 10 μL.

TRKC (G623R) Enzyme Reaction:

1.0 ng/μL TRKC (G623R) kinase, 1 μM TK Substrate-biotin polypeptide substrate, 62.9 μM ATP, 1× enzymatic buffer, 5 mM MgCl$_2$, and 1 mM DTT. The assay plate was White Proxiplate 384-Plus plate (PerkinElmer), the reaction was incubated at room temperature for 50 min, and the assay volume was 10 μL.

Detection Steps:

10 μL of detection reagent (containing 0.125 μM SA-XL665 and 5 μL 1×TK-Antibody) was added to the plate and incubated overnight at room temperature, and Synergy Neo 2 was used to read the plate.

Data Analysis

The value of 665/620 Ratio minus the value of negative control wells without enzyme, then the obtained value was converted according to the following formula into inhibition rate (%)=(1−Ratio$_{test}$/Ratio$_{max}$)×100%. Ratio$_{max}$ was the value of positive controls without tested compound, and Ratio$_{test}$ was the value of each concentration of different compounds. IC50 (nM) data was obtained by 4 parameter curve fitting (see Table 3).

TABLE 3

| 化合物 | TRKA (G595R) IC 50 (nM) |
|---|---|
| Example 5 | <10 |
| Example 11 | <10 |
| Example 13 | <1 |
| Example 17 | <10 |
| Example 19 | <1 |
| Example 20 | <1 |
| Example 21 | <1 |
| Example 22 | <1 |
| Example 24 | <1 |
| Example 25 | <1 |
| Example 26 | <1 |
| Example 27 | <1 |
| Example 28 | <1 |
| Example 29 | <10 |
| Example 30 | <1 |
| Example 31 | <10 |
| Example 32 | <1 |
| Example 33 | <1 |
| Example 34 | <10 |
| Example 35 | <1 |
| Example 36 | <1 |
| Example 37 | <1 |
| Example 40 | <10 |
| Example 41 | <1 |
| Example 42 | <1 |
| Example 43 | <1 |

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound of Formula I:

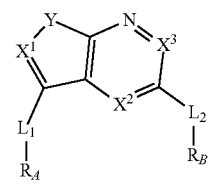

wherein the compound of Formula I has a structure according to Formula Ia:

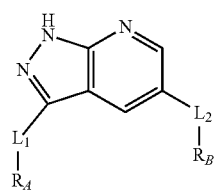

wherein
L$_1$ is

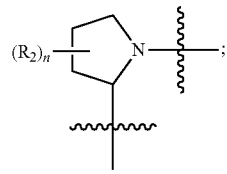

wherein n is 0, 1 or 2; and R$_2$ is each independently H or halogen;

L$_2$ is a substituted or unsubstituted —(X$^4$)$_z$—, wherein each of the X$^4$ is independently selected from the group consisting of a substituted or unsubstituted C$_1$-C$_8$ alkylene, —O—, —C(=O)—, —S—, —S(=O)—, —S(=O)$_2$—, —NH—, —CONH—, —NHCO—, —NHCONH—, —NHS(=O)—, and —NHS(=O)$_2$—; and z is 0, 1 or 2;

R$_A$ is selected from the group consisting of, phenyl, which is substituted or unsubstituted by one or more halogens, and pyridyl, which is substituted or unsubstituted by one or more groups selected from halogen and C$_1$-C$_6$ alkoxyl;

R$_B$ is selected from the group consisting of H, NH$_2$, OH, —COOH, substituted or unsubstituted C$_1$-C$_8$ alkyl, substituted or unsubstituted C$_3$-C$_{10}$ cycloalkyl, substituted or unsubstituted C$_1$-C$_8$ alkoxyl, substituted or unsubstituted C$_6$-C$_{10}$ aryl, substituted or unsubstituted C1-C6 amino, substituted or unsubstituted 5-10 membered heteroaryl comprising 1-3 hetero atoms selected from N, S and O, and substituted or unsubstituted 5-12 membered heterocyclic group comprising 1-3 hetero atoms, each of which is N, S or O;

unless otherwise specified, the "substituted" means that a group is substituted by one or more substituents selected from the group consisting of a halogen, C1-C6 alkoxyl, halogenated C1-C6 alkyl, halogenated C1-C6 alkoxyl, halogenated C3-C8 cycloalkyl, benzyloxy, methyl sulfuryl, —S(=O)$_2$NH$_2$, oxo (=O), —CN, hydroxy, —NH$_2$, carboxyl, C1-C6 amido, C1-C6 alkyl-(C1-C6 amido),

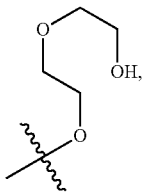 [SMILES: *OCCOCCO]

and a substituted or unsubstituted group selected from the group consisting of C1-C6 alkyl, C3-C8 cycloalkyl, C1-C6 amino, C6-C10 aryl, 5-10 membered heteroaryl comprising 1-3 heteroatoms selected from N, S and O, 3-12 membered heterocyclic group comprising 1-3 heteroatoms selected from N, S and O, —(CH$_2$)-C6-C10 aryl, and —(CH$_2$)-(5-10 membered heteroaryl comprising 1-3 heteroatoms selected from N, S and O), wherein the substituent is selected from the group consisting of a halogen, C1-C6 alkoxyl, halogenated C1-C6 alkyl, halogenated C1-C6 alkoxyl, halogenated C3-C8 cycloalkyl, methyl sulfuryl, —S(=O)$_2$NH$_2$, oxo (=O), —CN, hydroxyl, —NH$_2$, carboxyl, C1-C6 amido,

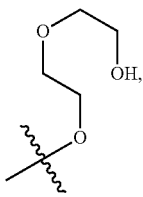 [SMILES: *OCCOCCO]

C1-C6 alkyl, C3-C8 cycloalkyl, C1-C6 amino, C6-C10 aryl, 5-10 membered heteroaryl comprising 1-3 heteroatoms selected from N, S and O, 3-12 membered heterocyclic group comprising 1-3 heteroatoms selected from N, S and O, —(CH$_2$)-C6-C10 aryl, and —(CH$_2$)-(5-10 membered heteroaryl comprising 1-3 heteroatoms selected from N, S, and O);

⸺ is the connection site of the group;

with the proviso that the compound of formula I is a chemical stable structure.

2. The compound of claim 1, wherein, $R_A$ is

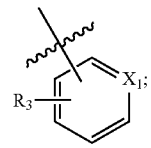

$X_1$ is CR or N; R is H, D or halogen; wherein the ⸺ is the connection site of $R_A$ and $L_1$;

$L_2$ is

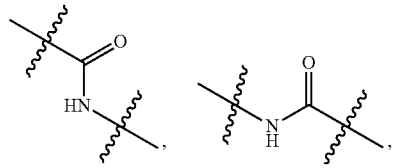

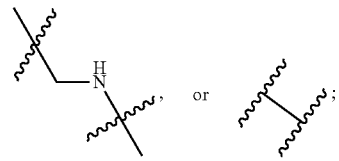

$R_B$ is selected from the group consisting of

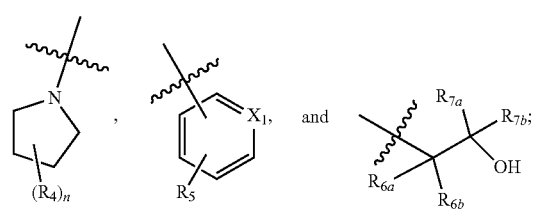

wherein the ⸺ is connection site of $R_B$ and $L_2$; wherein n is 0, 1 or 2;

$R_3$ is selected from the group consisting of H, halogen, and C1-C6 alkoxyl;

$R_4$ and $R_5$ are each independently selected from the group consisting of H, OH, halogen, C1-C6 alkyl-OH, $C_1$-$C_6$ alkoxyl, $C_1$-$C_6$ alkyl amino, $C_1$-$C_6$ alkyl amido, —($C_1$-$C_6$ alkyl)-NH—($C_1$-$C_6$ alkyl), and —($C_1$-$C_6$ alkyl amido)-($C_1$-$C_6$ alkyl);

$R_{6a}$, $R_{6b}$, $R_{7a}$, $R_{7b}$ are each independently selected from the group consisting of H, OH, and halogen; or $R_{6a}$, $R_{6b}$, $R_{7a}$, $R_{7b}$ together with carbon atoms to which they are connected form a 5-12 membered heterocyclic group comprising 1-3 heteroatoms selected from N, S and O.

3. The compound of claim 1, wherein the compound is of the structure of the following formula II:

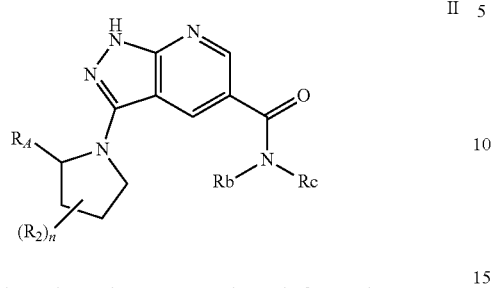

II wherein the Rb and Rc are selected from the group consisting of H, substituted or unsubstituted $C_1$-$C_8$ alkyl, and substituted or unsubstituted $C_3$-$C_8$ cycloalkyl, and wherein Rb and Rc and adjacent N atoms together form a substituted or unsubstituted 5-12 membered heterocyclic group.

4. The compound of claim 1, wherein the compound is of the structure of formula III:

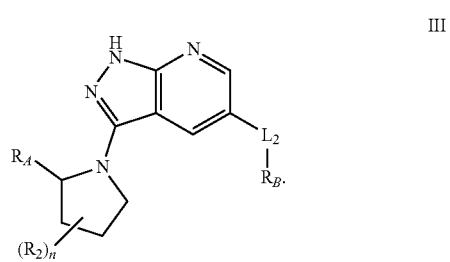

III

5. The compound of claim 1, wherein the compound is selected from the following structures:

| Compound | Structure |
|---|---|
| Example 1 | 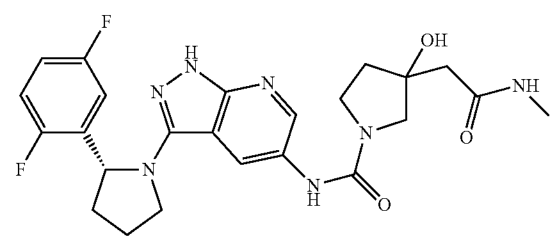 [SMILES: CNC(=O)CC1(O)CCN(C(=O)Nc2cnc3[nH]nc(N4CCC[C@@H]4c4cc(F)ccc4F)c3c2)C1] |
| Example 2 | 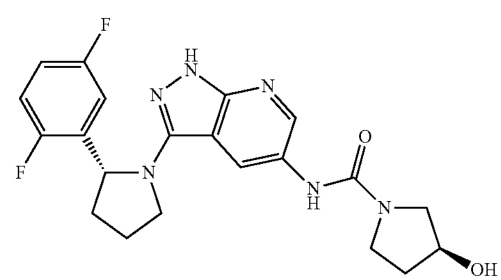 [SMILES: O=C(Nc1cnc2[nH]nc(N3CCC[C@@H]3c3cc(F)ccc3F)c2c1)N1CC[C@H](O)C1] |
| Example 3 | 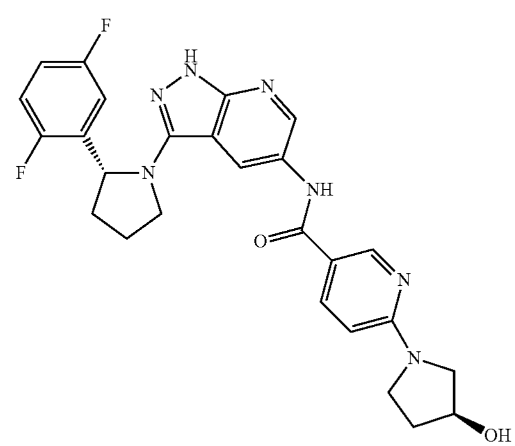 [SMILES: O=C(Nc1cnc2[nH]nc(N3CCC[C@@H]3c3cc(F)ccc3F)c2c1)c1ccc(N2CC[C@H](O)C2)nc1] |

-continued

| Compound | Structure |
|---|---|
| Example 4 | (2,5-difluorophenyl)pyrrolidinyl-1H-pyrazolo[3,4-b]pyridine-5-carboxamide |
| Example 5 | (2,5-difluorophenyl)(4-fluoro)pyrrolidinyl-1H-pyrazolo[3,4-b]pyridine-5-carboxamide |
| Example 6 | (2,5-difluorophenyl)pyrrolidinyl-1H-pyrazolo[3,4-b]pyridine-5-carboxylic acid (2-hydroxyethyl)amide |
| Example 7 | (2,5-difluorophenyl)pyrrolidinyl-1H-pyrazolo[3,4-b]pyridine-5-carboxylic acid methylamide |
| Example 8 | (2,5-difluorophenyl)pyrrolidinyl-1H-pyrazolo[3,4-b]pyridine-5-carboxylic acid (2-methoxyethyl)amide |
| Example 9 | (2,5-difluorophenyl)pyrrolidinyl-1H-pyrazolo[3,4-b]pyridine-5-carboxylic acid (3-hydroxypropyl)amide |

-continued

| Compound | Structure |
|---|---|
| Example 10 | *(structure image)* |
| Example 11 | *(structure image)* |
| Example 12 | *(structure image)* |
| Example 13 | *(structure image)* |
| Example 14 | *(structure image)* |
| Example 15 | *(structure image)* |

-continued
| Compound | Structure |
|---|---|
| Example 16 | 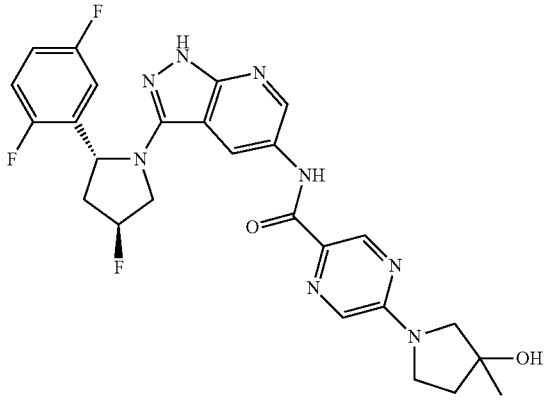 [SMILES: CC1(O)CCN(c2cnc(C(=O)Nc3cnc4[nH]nc(N5C[C@@H](F)C[C@@H]5c5cc(F)ccc5F)c4c3)cn2)C1] |
| Example 17 | 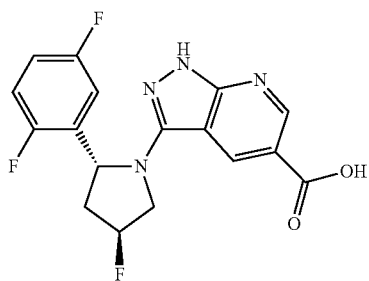 |
| Example 18 | 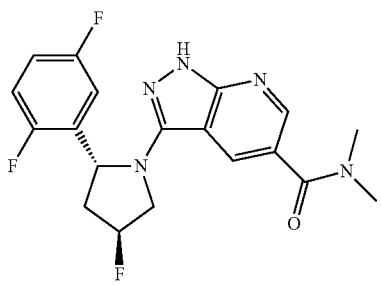 [SMILES: CN(C)C(=O)c1cnc2[nH]nc(N3C[C@@H](F)C[C@@H]3c3cc(F)ccc3F)c2c1] |
| Example 19 | 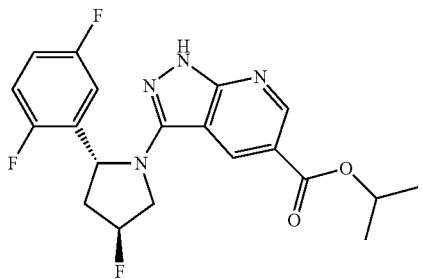 [SMILES: CC(C)OC(=O)c1cnc2[nH]nc(N3C[C@@H](F)C[C@@H]3c3cc(F)ccc3F)c2c1] |
| Example 20 | 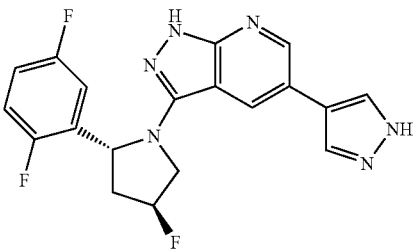 [SMILES: Fc1ccc(F)c([C@H]2C[C@H](F)CN2c2n[nH]c3ncc(-c4cn[nH]c4)cc23)c1] |

-continued
| Compound | Structure |
|---|---|
| Example 21 | 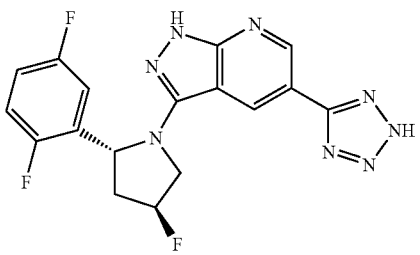 [SMILES: Fc1ccc(F)c([C@H]2C[C@H](F)CN2c2n[nH]c3ncc(-c4nn[nH]n4)cc23)c1] |
| Example 22 | 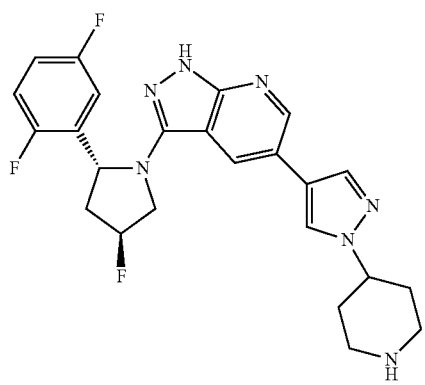 [SMILES: Fc1ccc(F)c([C@H]2C[C@H](F)CN2c2n[nH]c3ncc(-c4cnn(C5CCNCC5)c4)cc23)c1] |
| Example 23 | 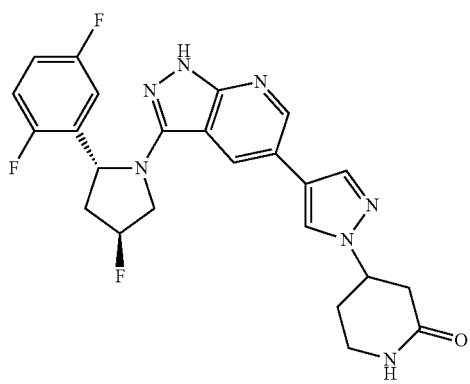 [SMILES: O=C1CC(n2cc(-c3cnc4[nH]nc(N5C[C@@H](F)C[C@@H]5c5cc(F)ccc5F)c4c3)cn2)CCN1] |
| Example 24 | 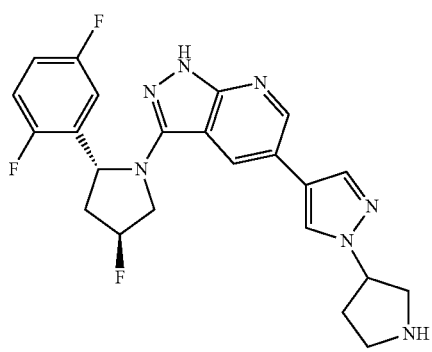 |

-continued
| Compound | Structure |
|---|---|
| Example 25 | 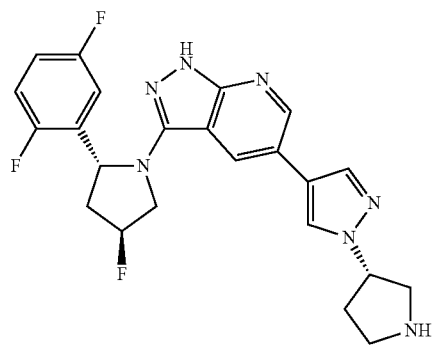 [SMILES: Fc1ccc(F)c([C@H]2C[C@H](F)CN2c2n[nH]c3ncc(-c4cnn([C@H]5CCNC5)c4)cc23)c1] |
| Example 26 | 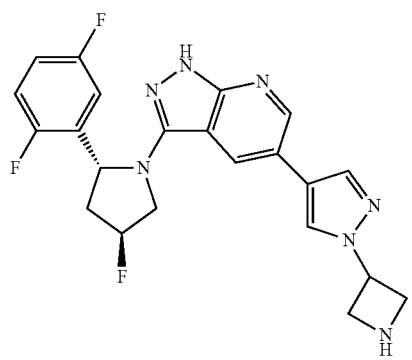 [SMILES: Fc1ccc(F)c([C@H]2C[C@H](F)CN2c2n[nH]c3ncc(-c4cnn(C5CNC5)c4)cc23)c1] |
| Example 27 | 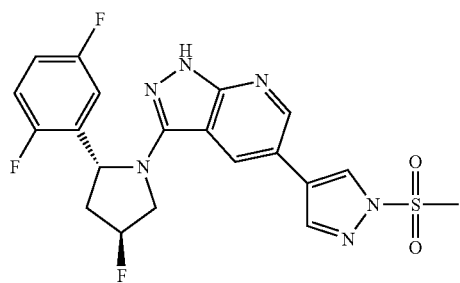 [SMILES: CS(=O)(=O)n1cc(-c2cnc3[nH]nc(N4C[C@@H](F)C[C@@H]4c4cc(F)ccc4F)c3c2)cn1] |
| Example 28 | 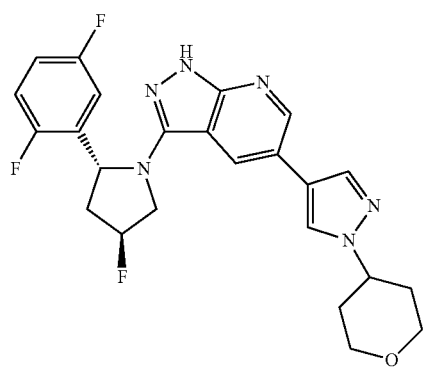 [SMILES: Fc1ccc(F)c([C@H]2C[C@H](F)CN2c2n[nH]c3ncc(-c4cnn(C5CCOCC5)c4)cc23)c1] |

-continued
| Compound | Structure |
|---|---|
| Example 29 | 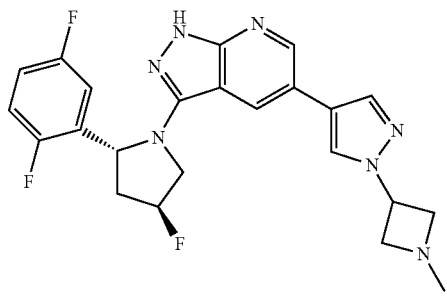 [SMILES: CN1CC(n2cc(-c3cnc4[nH]nc(N5C[C@@H](F)C[C@@H]5c5cc(F)ccc5F)c4c3)cn2)C1] |
| Example 30 | 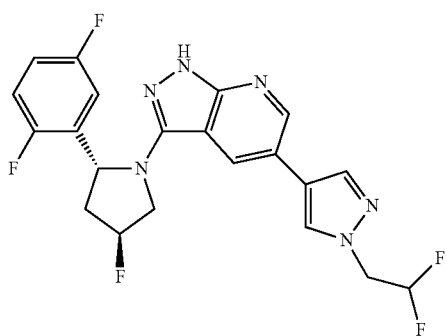 [SMILES: Fc1ccc(F)c([C@H]2C[C@H](F)CN2c2n[nH]c3ncc(-c4cnn(CC(F)F)c4)cc23)c1] |
| Example 31 | 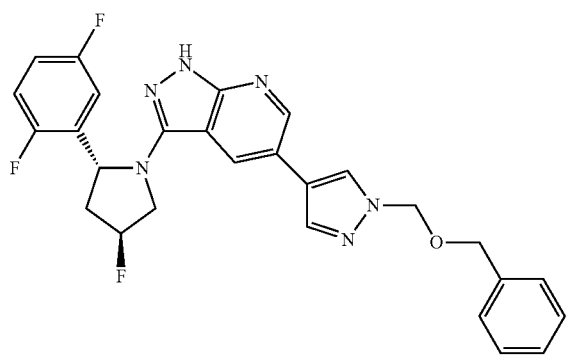 [SMILES: Fc1ccc(F)c([C@H]2C[C@H](F)CN2c2n[nH]c3ncc(-c4cnn(COCc5ccccc5)c4)cc23)c1] |
| Example 32 | 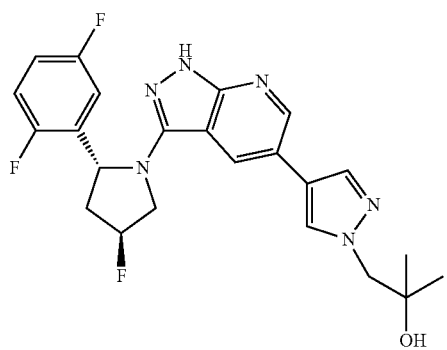 [SMILES: CC(C)(O)Cn1cc(-c2cnc3[nH]nc(N4C[C@@H](F)C[C@@H]4c4cc(F)ccc4F)c3c2)cn1] |

-continued
| Compound | Structure |
|---|---|
| Example 33 | 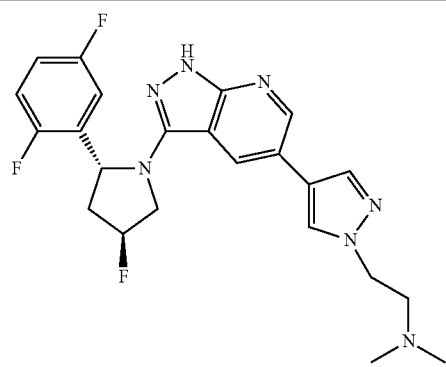 [SMILES: CN(C)CCn1cc(-c2cnc3[nH]nc(N4C[C@@H](F)C[C@@H]4c4cc(F)ccc4F)c3c2)cn1] |
| Example 34 | 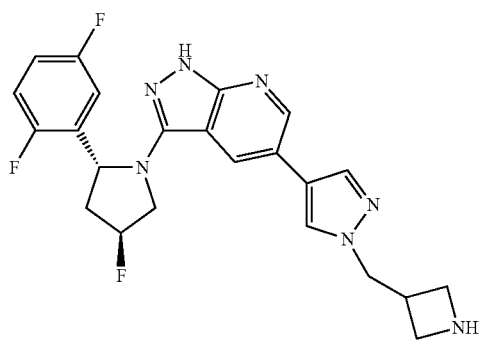 [SMILES: Fc1ccc(F)c([C@H]2C[C@H](F)CN2c2n[nH]c3ncc(-c4cnn(CC5CNC5)c4)cc23)c1] |
| Example 35 | 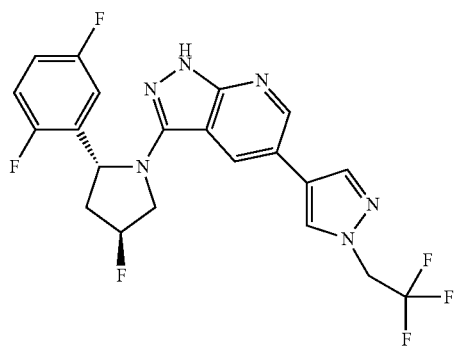 [SMILES: Fc1ccc(F)c([C@H]2C[C@H](F)CN2c2n[nH]c3ncc(-c4cnn(CC(F)(F)F)c4)cc23)c1] |
| Example 36 | 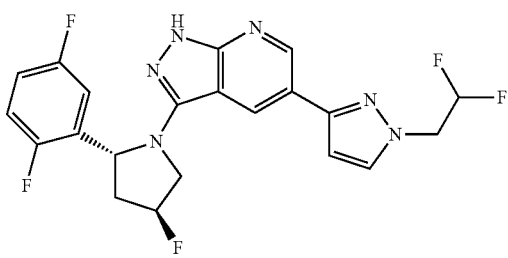 [SMILES: Fc1ccc(F)c([C@H]2C[C@H](F)CN2c2n[nH]c3ncc(-c4ccn(CC(F)F)n4)cc23)c1] |
| Example 37 | 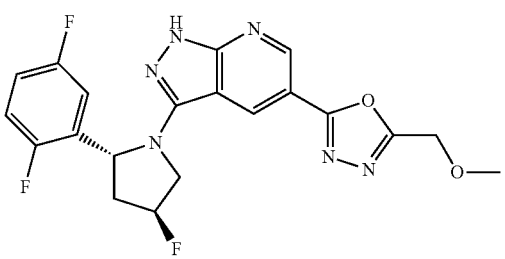 [SMILES: COCc1nnc(-c2cnc3[nH]nc(N4C[C@@H](F)C[C@@H]4c4cc(F)ccc4F)c3c2)o1] |

-continued
| Compound | Structure |
|---|---|
| Example 38 | 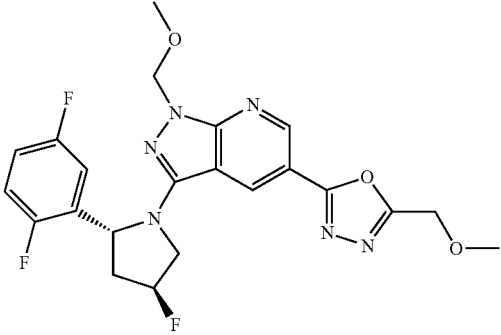 [SMILES: COCc1nnc(-c2cnc3c(c2)c(N2C[C@@H](F)C[C@@H]2c2cc(F)ccc2F)nn3COC)o1] |
| Example 39 | 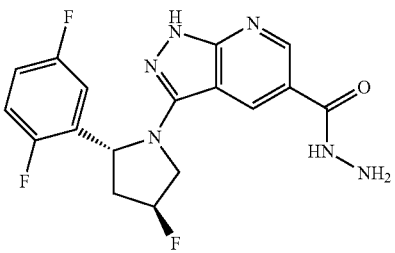 [SMILES: NNC(=O)c1cnc2[nH]nc(N3C[C@@H](F)C[C@@H]3c3cc(F)ccc3F)c2c1] |
| Example 40 | 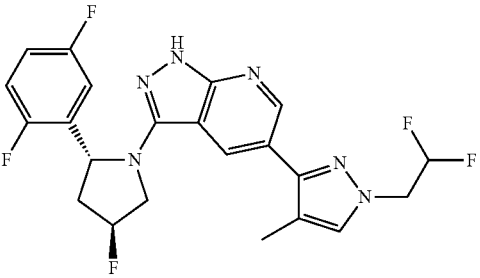 [SMILES: Cc1cn(CC(F)F)nc1-c1cnc2[nH]nc(N3C[C@@H](F)C[C@@H]3c3cc(F)ccc3F)c2c1] |
| Example 41 | 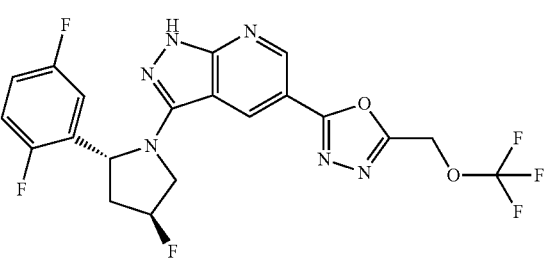 [SMILES: Fc1ccc(F)c([C@H]2C[C@H](F)CN2c2n[nH]c3ncc(-c4nnc(COC(F)(F)F)o4)cc23)c1] |
| Example 42 | 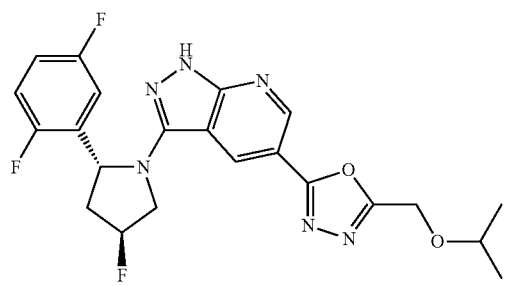 |

6. A pharmaceutical composition, wherein the pharmaceutical composition comprises (1) the compound of claim 1, or a stereoisomer thereof, tautomer thereof, or a pharmaceutically acceptable salt, hydrate or solvate thereof, and (2) pharmaceutically acceptable carriers.

7. A method of treating a disease comprising administering a therapeutically effective amount of the pharmaceutical composition of claim 6 to a subject in need thereof, wherein the disease is selected from the group consisting of cancers, proliferative diseases, pain, skin diseases or conditions, metabolic diseases, muscle diseases, neurological diseases, autoimmune diseases, itching caused by dermatitis, inflammation related diseases, and bone related diseases.

8. A method for treating a disease which relates to TRK function abnormalities, the method comprising the step: administrating the compound of claim 1 or a stereoisomer or a tautomer thereof, or a pharmaceutically acceptable salt, hydrate or solvate thereof to a subject in need thereof; and the disease is selected from the group consisting of cancers, proliferative diseases, pains, skin diseases or conditions, metabolic diseases, muscle diseases, neurological diseases, autoimmune diseases, itching caused by dermatitis, inflammation related diseases, and bone related diseases.

* * * * *